United States Patent
Virgili-Bernado et al.

(10) Patent No.: US 10,246,465 B2
(45) Date of Patent: Apr. 2, 2019

(54) ALKYL DERIVATIVES OF 1-OXA-4,9-DIAZASPIRO UNDECANE COMPOUNDS HAVING MULTIMODAL ACTIVITY AGAINST PAIN

(71) Applicant: LABORATORIOS DEL DR. ESTEVE S.A., Barcelona (ES)

(72) Inventors: Marina Virgili-Bernado, Barcelona (ES); Monica Alonso-Xalma, Barcelona (ES); Carlos Alegret-Molina, Barcelona (ES); Carmen Almansa-Rosales, Barcelona (ES); Monica Garcia Lopez, Barcelona (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 15/315,486

(22) PCT Filed: Jun. 2, 2015

(86) PCT No.: PCT/EP2015/001115
§ 371 (c)(1),
(2) Date: Dec. 1, 2016

(87) PCT Pub. No.: WO2015/185209
PCT Pub. Date: Dec. 10, 2015

(65) Prior Publication Data
US 2017/0313723 A1  Nov. 2, 2017

(30) Foreign Application Priority Data
Jun. 2, 2014 (EP) .................................... 14382209

(51) Int. Cl.
*C07D 498/10* (2006.01)
(52) U.S. Cl.
CPC ................. *C07D 498/10* (2013.01)
(58) Field of Classification Search
None
See application file for complete search history.

(56) References Cited

U.S. PATENT DOCUMENTS

| | | |
|---|---|---|
| 4,353,900 A | 10/1982 | Clark |
| 6,114,541 A | 9/2000 | Abrecht |
| 8,168,783 B2 | 5/2012 | Kokubo et al. |
| 2009/0105290 A1 | 4/2009 | Sundermann et al. |
| 2010/0120841 A1 | 5/2010 | Nakano et al. |
| 2012/0264749 A1 | 10/2012 | Hadida-Ruah |
| 2017/0101420 A1 | 4/2017 | Virgili-Bernado et al. |
| 2017/0197984 A1 | 7/2017 | Virgili-Bernado et al. |

FOREIGN PATENT DOCUMENTS

| | | |
|---|---|---|
| DE | 102005030061 | 12/2006 |
| EP | 0 061 333 | 9/1982 |
| EP | 1982714 | 10/2008 |
| WO | WO 2008/105497 | 9/2008 |
| WO | WO 2008/155132 | 12/2008 |
| WO | WO 2009/032667 | 3/2009 |
| WO | WO 2009/098448 | 8/2009 |
| WO | WO 2012/156693 | 11/2012 |
| WO | WO 2015/017305 | 2/2015 |

OTHER PUBLICATIONS

Clark, Robin D., Journal of Medicinal Chemistry, vol. 26, No. 6, p. 855-861, Jan. 1, 1983.
International Search Report for PCT/EP2015/001115 dated Jun. 23, 2015.
Database Registry, XP-002730855, Chemical Abstracts, May 12, 2010, Accession No. 1222524-76-6.
Kato, et al., Bioorganic & Medicinal Chemistry Letters, 2014, 24, 565-570.
Stocks, et al., Bioorganic & Medicinal Chemistry Letters, 2010, 20, 7458-7461.
Bornot et al., J. Med. Chem, 2013, 56, 1197-1210.
Dickenson, et al., Eur J Pain 9, 113-116 (2005).
Goldberg, et al., BMC Public Health, 11, 770 (2011).
Mao, et al., J. Pain 12, 157-166 (2011).
Turk, et al., Lancet 377, 2226-2235 (2011).
Zamanillo, et al., Eur. J. Pharmacol, 716, 78-93 (2013).
Chien, et al., Neuroscience Letters, 1995, 190, pp. 137-139.
Friedman, et al., Angew. Chem. Int. Ed. 2013, 52, pp. 9755-9758.

*Primary Examiner* — Samantha L Shtetengarts
(74) *Attorney, Agent, or Firm* — Hueschen and Sage

(57) ABSTRACT

The present invention relates to compounds having dual pharmacological activity towards both the sigma (σ) receptor, and the μ-opioid receptor and more particularly to diazaspiro undecane compounds having this pharmacological activity, to processes of preparation of such compounds, to pharmaceutical compositions comprising them, and to their use in therapy, in particular for the treatment of pain.

21 Claims, No Drawings

ALKYL DERIVATIVES OF 1-OXA-4,9-DIAZASPIRO UNDECANE COMPOUNDS HAVING MULTIMODAL ACTIVITY AGAINST PAIN

FIELD OF THE INVENTION

The present invention relates to compounds having dual pharmacological activity towards both the sigma (σ) receptor, and the μ-opioid receptor (MOR or mu-opioid) and more particularly to diazaspiro undecane derivatives compounds having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. Lancet 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. BMC Public Health. 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. Opioids in neuropathic pain: Clues from animal studies. Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. Neurosci. Lett. 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. Eur. J. Pharmacol, 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. J. Pain 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding to two different receptors relevant for the treatment of pain. This was mainly achieved by providing the compounds according to the invention that bind both to the μ-opioid receptor and to the $\sigma_1$ receptor.

SUMMARY OF THE INVENTION

In this invention a family of structurally distinct diazaspiro undecane derivatives which have a dual pharmacological activity towards both the sigma (σ) receptor, and the μ-opioid receptor was identified thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a very preferred embodiment if the compound has a binding expressed as $K_i$ which is preferably <1000 nM for both receptors, more preferably <500 nM, even more preferably <100 nM.

The invention is directed in a main aspect to a compound of general formula (I),

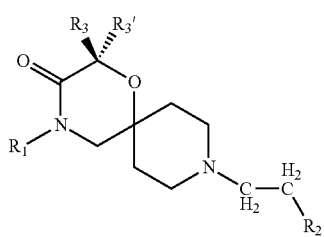

wherein $R_1$, $R_2$, $R_3'$ $R_3'$ are as defined below in the detailed description.

DETAILED DESCRIPTION OF THE INVENTION

The invention is directed to a family of structurally distinct diazaspiro undecane derivatives which have a dual pharmacological activity towards both the sigma (σ) receptor, and the μ-opioid receptor was identified thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a very preferred embodiment if the compound has a binding expressed as Ki which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to MOR and to $\sigma_1$ receptor), thereby enhancing the opioid analgesia through the $\sigma_1$ activation without increasing the undesirable side effects. This supports the therapeutic value of a dual MOR/$\sigma_1$ receptor compound whereby the $\sigma_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ opioid receptor agonists.

A dual compound that possess binding to both the μ-opioid receptor and to the $\sigma_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: $\sigma_1$ receptor antagonism and MOR agonism. It has to be noted, though, that both functionalities "antagonism" and "agonism" are also sub-divided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while $\sigma_1$ receptor antagonists show outstanding effects in preclinical neuropathic pain models. Thus, the $\sigma_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. J. Med. Chem, 56, 1197-1210 (2013)].

It has also surprisingly been found that the affinity for the μ-opioid receptor of the 1-oxa-4,9-diazaspiro[5.5]undecane derivatives described herein depends heavily on the precise nature of the substituents in $R_3$ position of Formula (I) and on their particular spatial configuration.

The binding affinity for the µ-opioid receptor was surprisingly found to reside predominantly in the $R_3$ substituent (different from hydrogen) occupying the spatial configuration as shown in Formula (I), independently of $R_3$ and $R_{3'}$ being the same substituents, different substituents (leading to a chiral center) or forming a cycloalkyl group. While when $R_3$ is hydrogen, the binding to the µ-opioid receptor is much weaker.

The affinity for the $\sigma_1$ receptor was basically maintained, being influenced in a lesser extent by the spatial configuration of the radicals in position $R_3$ or $R_{3'}$.

The optical isomers have been obtained by convenient enantioselective methods or via chiral HPLC separation or fractional crystallization of diastereomeric salts of the corresponding racemic mixtures.

In a particular aspect, the present invention is directed to compounds of general formula (I):

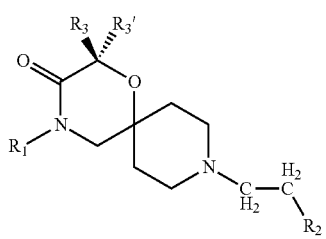

(I)

wherein $R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl;

$R_2$ is substituted or unsubstituted monocyclic aryl or substituted or unsubstituted monocyclic heterocyclyl $R_3$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, substituted or unsubstituted $C_{4-7}$ alkylaryl, substituted or unsubstituted $C_{3-6}$ aryl, substituted or unsubstituted $C_{3-6}$ heterocyclyl or substituted or unsubstituted $C_{4-7}$ alkylheterocyclyl;

$R_{3'}$ is hydrogen or unsubstituted $C_{1-6}$ alkyl, unsubstituted $C_{2-6}$ alkenyl or unsubstituted $C_{2-6}$ alkynyl, alternatively $R_3$ and $R_{3'}$ taken together (with the connecting C-atom) may form an substituted or unsubstituted $C_{3-6}$ cycloalkyl;

$R_4$, $R_{4'}$ and $R_{4''}$ are independently selected from hydrogen or substituted or unsubstituted $C_{1-6}$ alkyl, substituted or unsubstituted $C_{2-6}$ alkenyl or substituted or unsubstituted $C_{2-6}$ alkynyl, substituted or unsubstituted $C_{3-6}$ cycloalkyl;

$R_{4'''}$ is hydrogen or unsubstituted $C_{1-6}$ alkyl, unsubstituted $C_{2-6}$ alkenyl, unsubstituted $C_{2-6}$ alkynyl or -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Please note that "or a corresponding salt thereof" does also mean "or a corresponding pharmaceutically acceptable salt thereof". This does apply to all below described embodiments and uses of "salt" being thus equivalent to "pharmaceutically acceptable salt".

In a particular embodiment one or more of the following compounds are excluded:

2,4-dimethyl-9-phenethyl-1-oxa-4,9-diazaspiro[5.5]undecan-3-one, and/or 2-ethyl-4-methyl-9-phenethyl-1-oxa-4,9-diazaspiro[5.5]undecan-3-one, and/or 2-isopropyl-4-methyl-9-phenethyl-1-oxa-4,9-diazaspiro[5.5]undecan-3-one, and/or 2-butyl-4-ethyl-9-phenethyl-1-oxa-4,9-diazaspiro[5.5]undecan-3-one

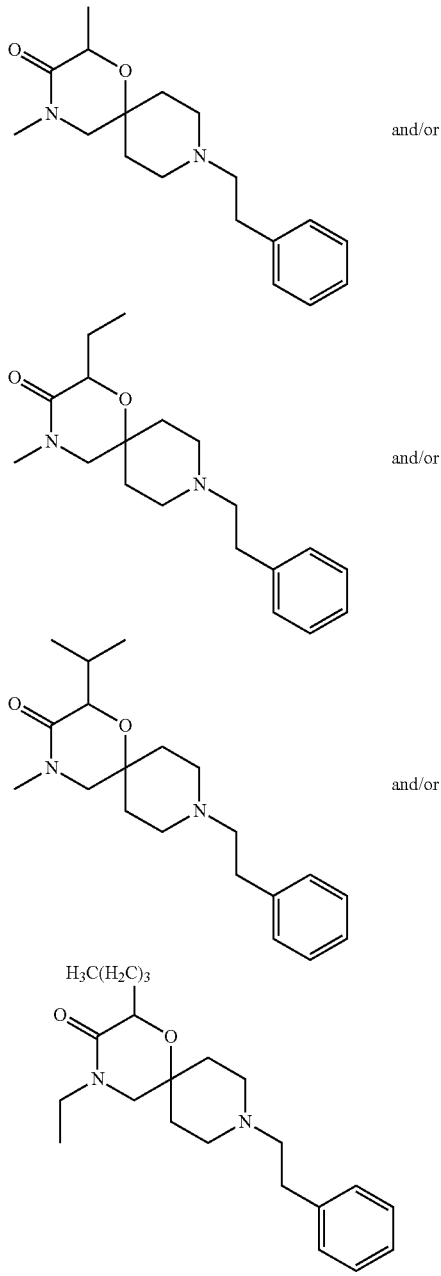

In a particular embodiment this exclusion only refers to the respective racemic form of this or these compound/s above.

In a particular embodiment all these 4 compounds above are excluded.

In a particular embodiment this exclusion also includes all the HCl salts of these compounds above or their pharmaceutically acceptable acid addition salts.

Some compounds from the state of the art (U.S. Pat. No. 4,353,900A) have been identified which are not part of the present invention since, as racemic compounds, they lack information on the spatial conformation of the group corresponding to R₃ in Formula (I). These compounds respond to the following names and formulae:

2,4-dimethyl-9-phenethyl-1-oxa-4,9-diazaspiro[5.5]undecan-3-one 2-ethyl-4-methyl-9-phenethyl-1-oxa-4,9-diazaspiro[5.5]undecan-3-one 2-isopropyl-4-methyl-9-phenethyl-1-oxa-4,9-diazaspiro[5.5]undecan-3-one 2-butyl-4-ethyl-9-phenethyl-1-oxa-4,9-diazaspiro[5.5]undecan-3-one

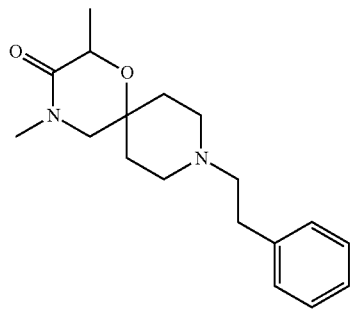

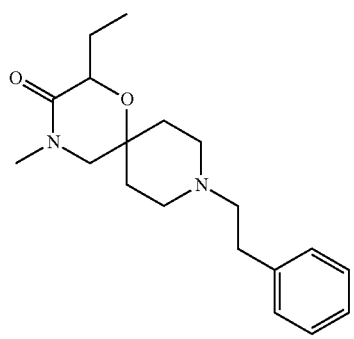

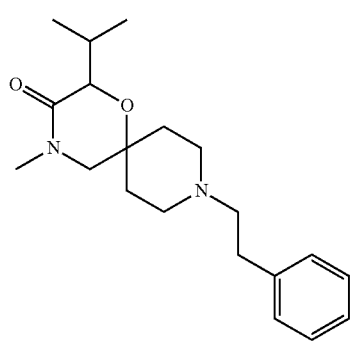

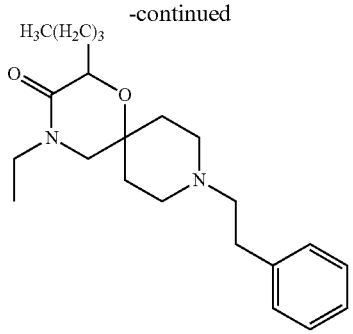

-continued

In another particular embodiment the condition/proviso applies especially for a compound according to Formula I that if $R_2$ is unsubstituted phenyl, $R_3$, is hydrogen and $R_3$ is $C_{1-4}$-alkyl, then $R_1$ may not be $C_{1-2}$-alkyl.

In the context of this invention, alkyl is understood as meaning saturated, linear or branched hydrocarbons, which may be unsubstituted or substituted once or several times. It encompasses e.g. —CH₃ and —CH₂—CH₃. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also CHF₂, CF₃ or CH₂OH etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—CH₃. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—CH₃ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In connection with alkyl, alkenyl, alkynyl and O-alkyl—unless defined otherwise—the term substituted in the context of this invention is understood as meaning replacement of at least one hydrogen radical on a carbon atom by halogen (F, Cl, I, Br), $NR_4R_{4'''}$, $SR_4$, $-S(O)R_4$, $-S(O)_2R_4$, $-OR_4$, $-C(O)OR_4$, $-CN$, haloalkyl, haloalkoxy or $-OC_{1-4}$alkyl being unsubstituted or substituted by one or more of OH or halogen (F, Cl, I, Br), being $R_4$, $R_{4'}$, $R_{4''}$ and $R_{4'''}$ as defined above, and wherein when different radicals $R_1$ to $R_{4''''}$ are present simultaneously in Formulas I to I'' they may be identical or different. More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. $-CH(OH)-CH=CH-CHCl_2$. when different radicals $R_1$ to $R_{4''''}$ are present simultaneously in Formulas I to I'' they may be identical or different.

Preferably in connection with alkyl, alkenyl, alkynyl or O-alkyl, substituted is understood in the context of this invention that any alky, alkenyl, alkynyl or O-alkyl which is substituted is substituted by one or more of halogen (F, Cl, I, Br), $-OR_4$, $-CN$, haloalkyl, or $-OC_{1-4}$alkyl being unsubstituted or substituted by one or more of OH or halogen (F, Cl, I, Br), being $R_4$, $R_{4'}$, $R_{4''}$ and $R_{4'''}$ as defined above, and wherein when different radicals $R_1$ to $R_{4''''}$ are present simultaneously in Formulas I to I'' they may be identical or different.

Preferably in connection with alkyl, alkenyl, alkynyl or O-alkyl, substituted is understood in the context of this invention that any alky, alkenyl, alkynyl or O-alkyl which is substituted is substituted by one or more of halogen (F, Cl, I, Br), $-OR_4$, $-CN$, or haloalkyl, being $R_4$, $R_{4'}$, $R_{4''}$ and $R_{4'''}$ as defined above, and wherein when different radicals $R_1$ to $R_{4''''}$ are present simultaneously in Formulas I to I'' they may be identical or different.

Most preferably in connection with alkyl, alkenyl, alkynyl or O-alkyl, substituted is understood in the context of this invention that any alky, alkenyl, alkynyl or O-alkyl which is substituted is substituted by one or more of halogen (F, Cl, I, Br), $-CN$, or haloalkyl.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. $-CH(OH)-CH=CH-CHCl_2$.

In the context of this invention haloalkyl is understood as meaning an alkyl being substituted once or several times by a halogen (selected from F, Cl, Br, I). It encompasses e.g. $-CH_2Cl$, $-CH_2F$, $-CHCl_2$, $-CHF_2$, $-CCl_3$, $-CF_3$ and $-CH_2-CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include $-CH_2Cl$, $-CH_2F$, $-CHCl_2$, $-CHF_2$, and $-CF_3$.

In the context of this invention haloalkoxy is understood as meaning an $-O$-alkyl being substituted once or several times by a halogen (selected from F, Cl, Br, I). It encompasses e.g. $-OCH_2Cl$, $-OCH_2F$, $-OCHCl_2$, $-OCHF_2$, $-OCCl_3$, $-OCF_3$ and $-OCH_2-CHCl_2$. Preferably haloalkyl is understood in the context of this invention as halogen-substituted $-OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include $-OCH_2Cl$, $-OCH_2F$, $-OCHCl_2$, $-OCHF_2$, and $-OCF_3$.

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphtyl or anthracenyl, preferably is phenyl.

In the context of this invention alkyl-aryl is understood as meaning an aryl group (see above) being connected to another atom through 1 to 4 ($-CH_2-$) groups. Most preferably alkyl-aryl is benzyl. Thus, e.g. $C_{4-7}$ alkylaryl means that the combined number of C-atoms in the aryl group and in the 1 to 4 ($-CH_2-$) groups with which the aryl is being connected to another atom is between 4 and 7.

In the context of this invention alkylheterocyclyl is understood as meaning an heterocyclyl group (see underneath) being connected to another atom through 1 to 4 ($-CH_2-$) groups. Most preferably alkylheterocyclyl is $-CH_2$-pyridine. Thus, e.g. $C_{4-7}$ alkylheterocyclyl means that the combined number of C-atoms in the heterocyclyl group and in the 1 to 4 ($-CH_2-$) groups with which the heterocyclyl is being connected to another atom is between 4 and 7.

In the context of this invention alkylcycloalkyl is understood as meaning an cycloalkyl group (see above) being connected to another atom through 1 to 4 ($-CH_2-$) groups. Most preferably alkylcycloalkyl is $-CH_2$-cyclopropyl. Thus, e.g. $C_{4-7}$ alkylcycloalkyl means that the combined number of C-atoms in the cycloalkyl group and in the 1 to 4 ($-CH_2-$) groups with which the cycloalkyl is being connected to another atom is between 4 and 7.

In a more general sense, a heterocyclyl radical or group is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times. Examples include heteroaryls such as furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole and quinazoline. Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring. Preferred examples include imidazole, oxadiazole, tetrazole, pyridine, pyrimidine, piperidine, piperazine, indene, 2,3-dihydroindene, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, pyrazole, thiophene, indole, benzimidazole, pyrrolo[2,3b] pyridine, benzoxazole, oxopyrrolidine, pyrimidine.

In a more specific sense, a heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a heterocyclic ring system of one or more rings of which at least one ring— with this (or these) ring(s) then not being aromatic— contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b] pyridine, benzoxazole, oxopyrrolidine, pyrimidine, oxazepane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

Preferably, the aryl is a monocyclic aryl.
Preferably, the heteroaryl is a monocyclic heteroaryl.
Preferably, the non-aromatic heterocyclyl is a monocyclic non-aromatic heterocyclyl.
Preferably, the cycloalkyl is a monocyclic cycloalkyl.

In connection with aryl (including alkyl-aryl), cycloalkyl (including alkyl-cycloalkyl) or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl by —$R_4$, —$OR_4$, halogen, =O, —$OCH_2CH_2OH$, —$SR_4$, —$S(O)R_4$, —$S(O)_2R_4$, —CN, haloalkyl, -haloalkoxy, —$NR_4R_{4'}$, —$NO_2$, —$NR_4C(O)R_{4'}$, —$NR_4SO_2R_{4'}$, —$C(O)OR_4$, —$C(O)NR_4R_{4'}$, —$NR_4C(O)NR_{4'}R_{4''}$, —$S(O)_2NR_4R_{4'}$, —$NR_4S(O)_2NR_{4'}R_{4''}$; $NR_xR_y$, with $R_x$ and $R_y$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_4$, $R_{4'}$, $R_{4''}$ and $R_{4'''}$ as defined above, and wherein when different radicals $R_1$ to $R_{4''''}$ are present simultaneously in Formulas I to I" they may be identical or different.

Preferably in connection with aryl (including alkyl-aryl), cycloalkyl (including alkyl-cycloalkyl) or heterocyclyl (including alkyl-heterocyclyl), substituted is understood in the context of this invention that any aryl, cycloalkyl and heterocyclyl which is substituted is substituted by one or more of —$OR_4$, halogen, —CN, haloalkyl-haloalkoxy, —$NR_4R_{4'''}$, —$NO_2$, —$NR_4C(O)R_{4'}$, —$C(O)OR_4$, —$C(O)NR_4R_{4'}$, —$NR_4C(O)NR_4R_{4'''}$, —$S(O)_2NR_4R_{4'}$, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br), being $R_4$, $R_{4'}$, $R_{4''}$ and $R_{4'''}$ as defined above, and wherein when different radicals $R_1$ to $R_{4''''}$ are present simultaneously in Formulas I to I" they may be identical or different.

Most preferably in connection with aryl (including alkyl-aryl), cycloalkyl (including alkyl-cycloalkyl) or heterocyclyl (including alkyl-heterocyclyl), substituted is understood in the context of this invention that any aryl, cycloalkyl and heterocyclyl which is substituted is substituted by one or more of —$OR_4$, halogen, —CN, haloalkyl-haloalkoxy, —$NR_4R_{4'''}$, —$NO_2$, —$NR_4C(O)R_{4'}$, —$C(O)NR_4R_{4'}$, —$NR_4C(O)NR_4R_{4'''}$, —$S(O)_2NR_4R_{4'}$, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br), being $R_4$, $R_{4'}$, $R_{4''}$ and $R_{4'''}$ as defined above, and wherein when different radicals $R_1$ to $R_{4''''}$ are present simultaneously in Formulas I to I" they may be identical or different.

Most preferably in connection with aryl (including alkyl-aryl), cycloalkyl (including alkyl-cycloalkyl) or heterocyclyl (including alkyl-heterocyclyl), substituted is understood in the context of this invention that any aryl, cycloalkyl and heterocyclyl which is substituted is substituted by one or more of —$R_{4''''}$, —$OR_{4''''}$, halogen, =O, —$OCH_2CH_2OH$, —$SR_{4''''}$, —$S(O)R_{4''''}$, —$S(O)_2R_{4''''}$, —CN, haloalkyl-haloalkoxy, —$NR_{4'''}R_{4''''}$, —$NO_2$, —$NR_{4'''}C(O)R_{4''''}$, —$NR_{4'''}SO_2R_{4''''}$, —$C(O)OR_{4''''}$, —$C(O)NR_{4'''}R_{4''''}$, —$NR_{4'''}C(O)NR_{4'''}R_{4''''}$, —$S(O)_2NR_{4'''}R_{4''''}$, —$NR_{4'''}S(O)_2NR_{4'''}R_{4''''}$, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br), being $R_4$, $R_{4'}$, $R_{4''}$ and $R_{4'''}$ as defined above, and wherein when different radicals $R_1$ to $R_{4''''}$ are present simultaneously in Formulas I to I" they may be identical or different.

Most preferably in connection with aryl (including alkyl-aryl), cycloalkyl (including alkyl-cycloalkyl) or heterocyclyl (including alkyl-heterocyclyl), substituted is understood in the context of this invention that any aryl, cycloalkyl and heterocyclyl which is substituted is substituted by one or more of —$R_{4'''}$, halogen, —$SR_{4'''}$, —CN, haloalkyl, —$NR_{4'''}R_{4'''}$, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br), being $R_4$, $R_{4'}$, $R_{4''}$ and $R_{4'''}$ as defined above, and wherein when different radicals $R_1$ to $R_{4''''}$ are present simultaneously in Formulas I to I" they may be identical or different.

Most preferably in connection with aryl (including alkyl-aryl), cycloalkyl (including alkyl-cycloalkyl) or heterocyclyl (including alkyl-heterocyclyl), substituted is understood in the context of this invention that any aryl, cycloalkyl and heterocyclyl which is substituted is substituted by one or more —$OR_{4'''}$, halogen, —CN, haloalkyl, -haloalkoxy, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br), being $R_4$, $R_{4'}$, $R_{4''}$ and $R_{4'''}$ as defined above, and wherein when different radicals $R_1$ to $R_{4''''}$ are present simultaneously in Formulas I to I" they may be identical or different.

Additionally to the above-mentioned substitutions, in connection with cycloalkyl, or heterocyl namely non-aromatic heterocyclyl, substituted is also understood—unless defined otherwise—as meaning substitution of the ring-system of the cycloalkyl or; non-aromatic heterocyclyl with

or =O.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those Derivatives that are converted in vivo to the compounds of the invention. Such Derivatives would readily occur to those skilled in the art, and include, depending on the functional groups present in the molecule and without limitation, the following Derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of an hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts. This applies also to its solvates or prodrugs.

In a preferred embodiment the compound according to the invention according to general formula I is a compound of formula I'

(I')

wherein q is 1, 2, 3 or 4, $R_1$ and $R_2$ are as defined above for the compound of formula (I);

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment the compound according to the invention of general formula I is a compound of formula I"

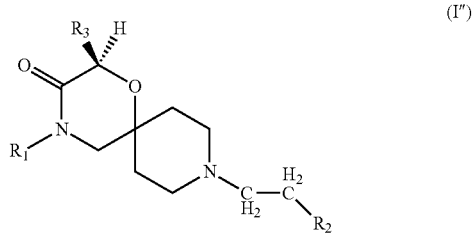

(I")

wherein $R_1$, $R_2$ and $R_3$ are as defined above for the compound of formula (I);

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a particular embodiment one or more of the following compounds are excluded:

2,4-dimethyl-9-phenethyl-1-oxa-4,9-diazaspiro[5.5]undecan-3-one, and/or 2-ethyl-4-methyl-9-phenethyl-1-oxa-4,9-diazaspiro[5.5]undecan-3-one, and/or 2-isopropyl-4-methyl-9-phenethyl-1-oxa-4,9-diazaspiro[5.5]undecan-3-one, and/or 2-butyl-4-ethyl-9-phenethyl-1-oxa-4,9-diazaspiro[5.5]undecan-3-one.

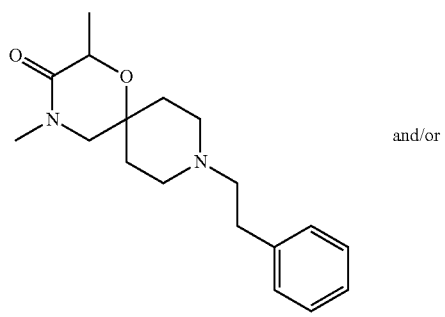

and/or

-continued

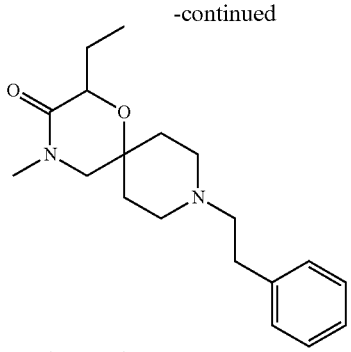

and/or

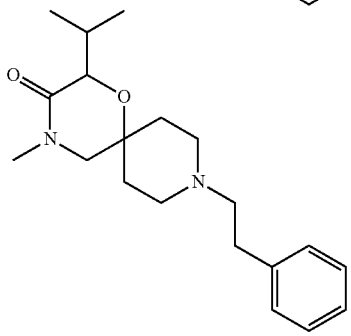

and/or

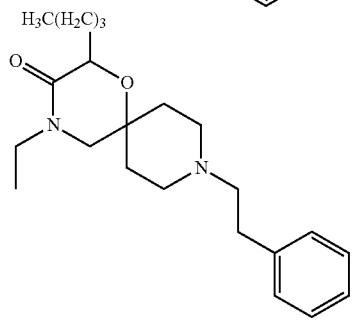

In a particular embodiment this exclusion only refers to the respective racemic form of this or these compound/s above.

In a particular embodiment all these 4 compounds above are excluded.

In another particular embodiment, the condition/proviso applies for a compound according to Formula I" that if $R_2$ is unsubstituted phenyl and $R_3$ is $C_{1-4}$-alkyl, then $R_1$ may not be $C_{1-2}$-alkyl.

In a preferred embodiment of the compound according to the invention according to general formulas I, I' or I" is a compound wherein $R_1$ is unsubstituted $C_{1-6}$ alkyl, unsubstituted $C_{2-6}$ alkenyl, unsubstituted $C_{2-6}$ alkynyl, unsubstituted $C_{3-6}$ cycloalkyl, unsubstituted $C_{4-7}$ alkylcycloalkyl;

$R_2$ is substituted or unsubstituted monocyclic aryl or substituted or unsubstituted monocyclic heterocyclyl;

$R_3$—for Formula I or I"—is unsubstituted $C_{1-6}$ alkyl, unsubstituted $C_{2-6}$ alkenyl, unsubstituted $C_{2-6}$ alkynyl, unsubstituted $C_{3-6}$ cycloalkyl, unsubstituted $C_{4-7}$ alkylcycloalkyl, unsubstituted $C_{4-7}$ alkylaryl, unsubstituted $C_{3-6}$ aryl, unsubstituted $C_{3-6}$ heterocyclyl or unsubstituted $C_{4-7}$ alkylheterocyclyl;

$R_{3'}$—for Formula I—is hydrogen or unsubstituted $C_{1-6}$ alkyl, unsubstituted $C_{2-6}$ alkenyl or unsubstituted $C_{2-6}$ alkynyl;

alternatively $R_3$ and $R_{3'}$ taken together (with the connecting C-atom) may form an unsubstituted $C_{3-6}$ cycloalkyl;

$R_4$, $R_{4'}$ and $R_{4''}$ are independently selected from hydrogen or unsubstituted $C_{1-6}$ alkyl, unsubstituted $C_{2-6}$ alkenyl or unsubstituted $C_{2-6}$ alkynyl, unsubstituted $C_{3-6}$ cycloalkyl; and $R_{4'''}$ is hydrogen or unsubstituted $C_{1-6}$ alkyl, unsubstituted $C_{2-6}$ alkenyl, unsubstituted $C_{2-6}$ alkynyl or -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment the compound according to the invention according to general formula I is a compound of formula I',
wherein q is 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein $R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein $R_2$ is substituted or unsubstituted monocyclic aryl or substituted or unsubstituted monocyclic heterocyclyl,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, or I" the compound is a compound, wherein $R_3$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, substituted or unsubstituted $C_{4-7}$ alkylaryl, substituted or unsubstituted $C_{3-6}$ aryl, substituted or unsubstituted $C_{3-6}$ heterocyclyl or substituted or unsubstituted $C_{4-7}$ alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I the compound is a compound, wherein $R_{3'}$ is hydrogen or unsubstituted $C_{1-6}$ alkyl, unsubstituted $C_{2-6}$ alkenyl or unsubstituted $C_{2-6}$ alkynyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I the compound is a compound, wherein $R_3$ and $R_{3'}$ taken together (with the connecting C-atom) may form an substituted or unsubstituted $C_{3-6}$ cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein $R_4$, $R_{4'}$ and $R_{4''}$ are independently selected from hydrogen or substituted or unsubstituted $C_{1-6}$ alkyl, substituted or unsubstituted $C_{2-6}$ alkenyl or substituted or unsubstituted $C_{2-6}$ alkynyl, substituted or unsubstituted $C_{3-6}$ cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein $R_{4'''}$ is hydrogen or unsubstituted $C_{1-6}$ alkyl, unsubstituted $C_{2-6}$ alkenyl, unsubstituted $C_{2-6}$ alkynyl or -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein $R_1$ is unsubstituted $C_{1-6}$ alkyl, unsubstituted $C_{2-6}$ alkenyl, unsubstituted $C_{2-6}$ alkynyl, unsubstituted C36 cycloalkyl, unsubstituted $C_{4-7}$ alkylcycloalkyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein $R_2$ is substituted or unsubstituted monocyclic aryl or substituted or unsubstituted monocyclic heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I or I" the compound is a compound, wherein $R_3$ is unsubstituted $C_{1-6}$ alkyl, unsubstituted $C_{2-6}$ alkenyl, unsubstituted $C_{2-6}$ alkynyl, unsubstituted $C_{3-6}$ cycloalkyl, unsubstituted $C_{4-7}$ alkylcycloalkyl, unsubstituted $C_{4-7}$ alkylaryl, unsubstituted $C_{3-6}$ aryl, unsubstituted $C_{3-6}$ heterocyclyl or unsubstituted $C_{4-7}$ alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I the compound is a compound, wherein $R_{3'}$ is hydrogen or unsubstituted $C_{1-6}$ alkyl, unsubstituted $C_{2-6}$ alkenyl or unsubstituted $C_{2-6}$ alkynyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I the compound is a compound, wherein $R_3$ and $R_{3'}$ taken together (with the connecting C-atom) may form an unsubstituted $C_{3-6}$ cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein $R_4$, $R_{4'}$ and $R_{4''}$ are independently selected from hydrogen or unsubstituted $C_{1-6}$ alkyl, unsubstituted $C_{2-6}$ alkenyl or unsubstituted $C_{2-6}$ alkynyl, unsubstituted $C_{3-6}$ cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein $R_{4'''}$ is hydrogen or unsubstituted $C_{1-6}$ alkyl, unsubstituted $C_{2-6}$ alkenyl, unsubstituted $C_{2-6}$ alkynyl or -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I' the compound is a compound, wherein q is 1, 2, 3 or 4 optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein in $R_1$ as defined in any of the above embodiments, the alkyl is $C_{1-4}$ alkyl like methyl, ethyl, propyl or butyl; the $C_{1-6}$ alkyl is preferably selected from methyl, ethyl, propyl, butyl, pentyl, hexyl, isopropyl, or 2-methylpropyl, preferably the $C_{1-6}$ alkyl is methyl, ethyl, isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the $C_{3-6}$ cycloalkyl is preferably selected from cyclopropyl, cyclobutyl, cyclopentyl or cyclohexyl; preferably the $C_{3-6}$ cycloalkyl is cyclopropyl;

and/or in $R_2$ as defined in any of the above embodiments, the aryl is phenyl;

and/or the heterocyclyl is a heterocyclic ring system of one saturated or unsaturated ring which contains one or more heteroatoms from the group consisting of nitrogen, oxygen and/or sulfur in the ring; more preferably is selected from imidazole, oxadiazole, tetrazole, pyridine, pyrimidine, piperidine, piperazine, thiazole, tetrahydropyrane, morpholine, furan, triazole, isoxazole, pyrazole, thiophene, pyrrole, pyrazine, oxopyrrolidine, pyrimidine, preferably the heterocyclyl is pyridine or thiazole;

and/or in $R_3$—for Formula I or I"—as defined in any of the above embodiments, the alkyl is $C_{1-4}$ alkyl like methyl, ethyl, propyl or butyl; the $C_{1-6}$ alkyl is preferably selected from methyl, ethyl, propyl, butyl, pentyl, hexyl, isopropyl, or 2-methylpropyl, preferably the $C_{1-6}$ alkyl is methyl, ethyl, isopropyl, and/or the $C_{2-6}$-alkenyl, is preferably selected from ethylene, propylene, butylene, pentylene or hexylene;

and/or the $C_{2-6}$-alkynyl like ethyne, propyne, butyne, pentyne or hexyne, preferably propyne;

and/or the aryl is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the $C_{3-6}$ cycloalkyl is preferably selected from cyclopropyl, cyclobutyl, cyclopentyl or cyclohexyl;

and/or in $R_3$—for Formula I—as defined in any of the above embodiments, the $C_{1-6}$ alkyl is preferably selected from methyl, ethyl, propyl, butyl, pentyl, hexyl, isopropyl, or 2-methylpropyl, preferably, the $C_{1-6}$ alkyl is methyl or ethyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or in $R_3$ and $R_{3'}$—for Formula I—taken together (with the connecting C-atom) and forming a cycloalkyl as defined in any of the above embodiments, the $C_{3-6}$ cycloalkyl is preferably selected from cyclopropyl, cyclobutyl, cyclopentyl or cyclohexyl, preferably the $C_{3-6}$ cycloalkyl is cyclopropyl or cyclopentyl;

and/or in $R_4$, $R_{4'}$ and $R_{4''}$ as defined in any of the above embodiments, the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the $C_{3-6}$ cycloalkyl is preferably selected from cyclopropyl, cyclobutyl, cyclopentyl or cyclohexyl;

and/or in $R_{4'''}$ as defined in any of the above embodiments, the $C_{1-6}$ alkyl is preferably selected from methyl, ethyl, propyl, butyl, pentyl, hexyl, isopropyl, or 2-methylpropyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein in $R_1$ as defined in any of the above embodiments, the alkyl is $C_{1-4}$ alkyl like methyl, ethyl, propyl or butyl; the $C_{1-6}$ alkyl is preferably selected from methyl, ethyl, propyl, butyl, pentyl, hexyl, isopropyl, or 2-methylpropyl, preferably the $C_{1-6}$ alkyl is methyl, ethyl, isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the $C_{3-6}$ cycloalkyl is preferably selected from cyclopropyl, cyclobutyl, cyclopentyl or cyclohexyl; preferably the $C_{3-6}$ cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein in $R_2$ as defined in any of the above embodiments, the aryl is phenyl;

and/or the heterocyclyl is a heterocyclic ring system of one saturated or unsaturated ring which contains one or more heteroatoms from the group consisting of nitrogen, oxygen and/or sulfur in the ring; more preferably is selected from imidazole, oxadiazole, tetrazole, pyridine, pyrimidine, piperidine, piperazine, thiazole, tetrahydropyrane, morpholine, furan, triazole, isoxazole, pyrazole, thiophene, pyrrole, pyrazine, oxopyrrolidine, pyrimidine, preferably the heterocyclyl is pyridine or thiazole;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I or I" the compound is a compound, wherein in $R_3$ as defined in any of the above embodiments, the alkyl is $C_{1-4}$ alkyl like methyl, ethyl, propyl or butyl;

the $C_{1-6}$ alkyl is preferably selected from methyl, ethyl, propyl, butyl, pentyl, hexyl, isopropyl, or 2-methylpropyl, preferably the $C_{1-6}$ alkyl is methyl, ethyl, isopropyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne, preferably propyne;

and/or the aryl is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, and/or the $C_{3-6}$ cycloalkyl is preferably selected from cyclopropyl, cyclobutyl, cyclopentyl or cyclohexyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I the compound is a compound, wherein in $R_3$, as defined in any of the above embodiments, the $C_{1-6}$ alkyl is preferably selected from methyl, ethyl, propyl, butyl, pentyl, hexyl, isopropyl, or 2-methylpropyl, preferably, the $C_{1-6}$ alkyl is methyl or ethyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formula I the compound is a compound, wherein in $R_3$ and $R_{3'}$ taken together (with the connecting C-atom) and forming a cycloalkyl as defined in any of the above embodiments, the $C_{3-6}$ cycloalkyl is preferably selected from cyclopropyl, cyclobutyl, cyclopentyl or cyclohexyl, preferably the $C_{3-6}$ cycloalkyl is cyclopropyl or cyclopentyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein in $R_4$, $R_{4'}$ and $R_{4''}$ as defined in any of the above embodiments, the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the $C_{3-6}$ cycloalkyl is preferably selected from cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', or I" the compound is a compound, wherein in $R_{4'''}$ as defined in any of the above embodiments, the $C_{1-6}$ alkyl is preferably selected from methyl, ethyl, propyl, butyl, pentyl, hexyl, isopropyl, or 2-methylpropyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment $R_1$ is substituted or unsubstituted methyl, substituted or unsubstituted ethyl, substituted or unsubstituted isopropyl or substituted or unsubstituted cyclopropyl, preferably $R_1$ is unsubstituted methyl, unsubstituted ethyl, unsubstituted isopropyl or unsubstituted cyclopropyl;

In another preferred embodiment $R_2$ is substituted or unsubstituted phenyl, substituted or unsubstituted pyridine or substituted or unsubstituted thiazole.

In a most preferred embodiment $R_3$ is substituted or unsubstituted methyl, substituted or unsubstituted ethyl, substituted or unsubstituted isopropyl, substituted or unsubstituted propyne, substituted or unsubstituted benzyl or —$CH_2CH_2OH$, preferably $R_3$ is unsubstituted methyl, unsubstituted ethyl, unsubstituted isopropyl, unsubstituted propyne, unsubstituted benzyl or —$CH_2CH_2OH$.

In a preferred embodiment $R_{3'}$ is hydrogen, substituted or unsubstituted methyl or substituted or unsubstituted ethyl, preferably $R_{3'}$ is hydrogen, unsubstituted methyl or unsubstituted ethyl.

In another preferred embodiment $R_3$ is substituted or unsubstituted methyl, substituted or unsubstituted ethyl, substituted or unsubstituted isopropyl, substituted or unsubstituted propyne, substituted or unsubstituted benzyl or —$CH_2CH_2OH$, while $R_{3'}$ is hydrogen, substituted or unsubstituted methyl or substituted or unsubstituted ethyl, In another preferred embodiment $R_3$ is unsubstituted methyl, unsubstituted ethyl, unsubstituted isopropyl, unsubstituted propyne, unsubstituted benzyl or —$CH_2CH_2OH$, while $R_{3'}$ is hydrogen, unsubstituted methyl or unsubstituted ethyl, In a preferred embodiment $R_3$ is unsubstituted methyl, unsubstituted ethyl, unsubstituted isopropyl, unsubstituted benzyl, unsubstituted propyne or —$CH_2CH_2OH$ while $R_{3'}$ is hydrogen.

In another preferred embodiment $R_3$ is substituted or unsubstituted methyl while $R_{3'}$ is substituted or unsubstituted methyl, preferably, $R_3$ is unsubstituted methyl while $R_{3'}$ is unsubstituted methyl.

In another preferred embodiment $R_3$ is substituted or unsubstituted ethyl while $R_{3'}$ is substituted or unsubstituted ethyl, preferably $R_3$ is unsubstituted ethyl while $R_{3'}$ is unsubstituted ethyl.

In another preferred embodiment $R_3$ is substituted or unsubstituted propyne while $R_{3'}$ is hydrogen, preferably $R_3$ is unsubstituted propyne while $R_{3'}$ is hydrogen, In another preferred embodiment $R_3$ is substituted or unsubstituted benzyl while $R_{3'}$ is hydrogen, preferably $R_3$ is unsubstituted benzyl while $R_{3'}$ is hydrogen.

In another preferred embodiment $R_3$ is —$CH_2CH_2OH$ while $R_{3'}$ is hydrogen.

In another preferred embodiment $R_3$ and $R_{3'}$ taken together (with the connecting C-atom) is substituted or unsubstituted cyclopropyl or substituted or unsubstituted cyclopentyl, preferably, $R_3$ and $R_{3'}$ taken together (with the connecting C-atom) is unsubstituted cyclopropyl or unsubstituted cyclopentyl In a preferred embodiment $R_4$, $R_{4'}$ and $R_{4''}$ are hydrogen or substituted or unsubstituted methyl.

In a preferred embodiment $R_4$, $R_{4'}$ and $R_{4''}$ are hydrogen or unsubstituted methyl.

In another preferred embodiment $R_{4'''}$ is hydrogen or -Boc.

In another preferred embodiment $R_{4'''}$ is unsubstituted methyl.

In particular preferred embodiment $R_4$, $R_{4'}$ and $R_{4''}$ are hydrogen or substituted or unsubstituted methyl, while $R_{4'''}$ is hydrogen or -Boc.

In particular preferred embodiment $R_4$, $R_{4'}$ and $R_{4''}$ are hydrogen or unsubstituted methyl, while $R_{4'''}$ is hydrogen or -Boc.

In another particular preferred embodiment q is 1.

In an embodiment of the invention in the compound of general formulas I, I', and I"

the halogen is fluorine, chlorine, iodine or bromine.

In a most preferred embodiment of the invention in the compound according to general formulas I, I', and I"

the halogen is fluorine or chlorine.

In an embodiment of the invention in the compound of general formulas I, I', and I"

the haloalkyl is —$CF_3$.

In another embodiment of the invention in the compound of general formulas I, I', and I"

the haloalkoxy is —$OCF_3$.

In another preferred embodiment of the compound according to the invention according to general formulas I, I', or I" the compound is a compound, wherein $R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, wherein the cycloalkyl in $R_1$ if substituted (also in alkylcycloalkyl) is substituted with substituents selected from —$R_{4'''}$, halogen, —$SR_{4'''}$, —CN, haloalkyl, —$NR_{4''}R_{4'''}$, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', or I" the compound is a compound, wherein $R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, wherein the alkyl, alkenyl and alkynyl in $R_1$ if substituted are substituted with substituents selected from halogen, —CN, haloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', or I" the compound is a compound, wherein $R_2$ is substituted or unsubstituted monocyclic aryl or substituted or unsubstituted monocyclic heterocyclyl, wherein the aryl, or heterocyclyl in $R_2$ if substituted is substituted with substituents selected from —$R_4$, —$OR_4$, halogen, =O, —$OCH_2CH_2OH$, —$SR_4$, —$S(O)R_4$, —$S(O)_2R_4$, —CN, haloalkyl-haloalkoxy, —$NR_4R_{4'''}$, —$NO_2$, —$NR_4C(O)R_{4'}$, —$NR_4SO_2R_{4'}$, —$C(O)OR_4$, —$C(O)NR_4R_{4'}$, —$NR_4C(O)NR_4R_{4''}$, —$S(O)_2NR_4R_{4'}$, —$NR_4S(O)_2NR_4R_{4'''}$, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', or I" the compound is a compound, wherein $R_2$ is substituted or unsubstituted monocyclic aryl or substituted or unsubstituted monocyclic heterocyclyl, wherein the aryl or heterocyclyl in $R_2$ if substituted is substituted with substituents selected from —$R_{4''''}$, —$OR_{4''''}$, halogen, =O, —$OCH_2CH_2OH$, —$SR_{4''''}$, —$S(O)R_{4''''}$, —$S(O)_2R_{4''''}$, —CN, haloalkyl-haloalkoxy, —$NR_{4'''}R_{4''''}$, —$NO_2$, —$NR_{4'''}C(O)R_{4''''}$, —$NR_{4'''}S(O)_2R_{4''''}$, —$C(O)OR_{4''''}$, —$C(O)NR_{4'''}R_{4''''}$, —$NR_{4'''}C(O)NR_{4'''}R_{4''''}$, —$S(O)_2NR_{4'''}R_{4''''}$, —$NR_{4'''}S(O)_2NR_{4'''}R_{4''''}$ optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I or I" the compound is a compound, wherein $R_3$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, substituted or unsubstituted $C_{4-7}$ alkylaryl, substituted or unsubstituted $C_{3-6}$ aryl, substituted or unsubstituted $C_{3-6}$ heterocyclyl or substituted or unsubstituted $C_{4-7}$ alkylheterocyclyl;

wherein the aryl, heterocyclyl or cycloalkyl in $R_3$ if substituted (also in alkylaryl, alkylcycloalkyl or alkylheterocyclyl) is substituted with substituents selected from —$R_4$, —$OR_4$, halogen, =O, —$OCH_2CH_2OH$, —$SR_4$, —$S(O)R_4$, —$S(O)_2R_4$, —CN, haloalkyl, -haloalkoxy, —$NR_4R_{4'''}$, —$NO_2$, —$NR_4C(O)R_{4'}$, —$NR_4S(O)_2R_{4'}$, —$C(O)OR_4$, —$C(O)NR_4R_{4'}$, —$NR_4C(O)NR_4R_{4''}$, —$S(O)_2NR_4R_{4'}$, —$NR_4S(O)_2NR_4R_{4''}$ optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I or I" the compound is a compound, wherein $R_3$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, substituted or unsubstituted $C_{4-7}$ alkylaryl, substituted or unsubstituted $C_{3-6}$ aryl, substituted or unsubstituted $C_{3-6}$ heterocyclyl or substituted or unsubstituted $C_{4-7}$ alkylheterocyclyl;

wherein the aryl, heterocyclyl or cycloalkyl in $R_3$ if substituted (also in alkylaryl, alkylcycloalkyl or alkylheterocyclyl) is substituted with substituents selected from —$R_{4''''}$, —$OR_{4''''}$, halogen, =O, —$OCH_2CH_2OH$, —$SR_{4''''}$, —$S(O)R_{4''''}$, —$S(O)_2R_{4''''}$, —CN, haloalkyl, -haloalkoxy, —$NR_{4'''}R_{4''''}$, —$NO_2$, —$NR_{4'''}C(O)R4'''$, —$NR_{4'''}S(O)_2R_{4''''}$, —$C(O)OR_{4''''}$, —$C(O)NR_{4'''}R_{4''''}$, —$NR_{4'''}C(O)NR_{4'''}R_{4''''}$, —$S(O)_2NR_{4'''}R_{4''''}$, —$NR_{4'''}S(O)_2NR_{4'''}R_{4''''}$ optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I or I" the compound is a compound, wherein $R_3$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, substituted or unsubstituted $C_{4-7}$ alkylaryl, substituted or unsubstituted $C_{3-6}$ aryl, substituted or unsubstituted $C_{3-6}$ heterocyclyl or substituted or unsubstituted $C_{4-7}$ alkylheterocyclyl;

and wherein the alkyl, alkenyl and alkynyl in $R_3$ if substituted are substituted with substituents selected from —$OR_4$, halogen, —CN, haloalkyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I or I" the compound is a compound, wherein $R_3$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, substituted or unsubstituted $C_{4-7}$ alkylaryl, substituted or unsubstituted $C_{3-6}$ aryl, substituted or unsubstituted $C_{3-6}$ heterocyclyl or substituted or unsubstituted $C_{4-7}$ alkylheterocyclyl;

and wherein the alkyl, alkenyl and alkynyl in $R_3$ if substituted are substituted with substituents selected from —$OR_{4''''}$, halogen, —CN, haloalkyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formula I the compound is a compound, wherein $R_3$ and $R_{3'}$ taken together (with the connecting C-atom) may form an substituted or unsubstituted $C_{3-6}$ cycloalkyl;

wherein the cycloalkyl for $R_3$ and $R_{3'}$ taken together if substituted is substituted with substituents selected from —$R_4$, —$OR_4$, halogen, =O, —$OCH_2CH_2OH$, —$SR_4$, —$S(O)R_4$, —$S(O)_2R_4$, —CN, haloalkyl, -haloalkoxy, —$NR_4R_{4'''}$, —$NO_2$, —$NR_4C(O)R_{4'}$, —$NR_4S(O)_2R_{4'}$, —$C(O)OR_4$, —$C(O)NR_4R_{4'}$, —$NR_4C(O)NR_4R_{4''}$, —$S(O)_2NR_4R_{4'}$, —$NR_4S(O)_2NR_4R_{4''}$ optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I the compound is a compound, wherein $R_3$ and $R_{3'}$ taken together (with the connecting C-atom) may form an substituted or unsubstituted $C_{3-6}$ cycloalkyl;

wherein the cycloalkyl for $R_3$ and $R_{3'}$ taken together if substituted is substituted with substituents selected from —$R_{4''''}$, —$OR_{4''''}$, halogen, =O, —$OCH_2CH_2OH$, —$SR_{4''''}$, —$S(O)R_{4''''}$, —$S(O)_2R_{4''''}$, —CN, haloalkyl, -haloalkoxy, —$NR_{4'''}R_{4''''}$, —$NO_2$, —$NR_{4'''}C(O)R4'''$, —$NR_{4'''}S(O)_2R_{4''''}$, —$C(O)OR_{4''''}$, —$C(O)NR_{4'''}R_{4''''}$, —$NR_{4'''}C(O)NR_4R_{4''''}$, —$S(O)_2NR_{4'''}R_{4''''}$, —$NR_{4'''}S(O)_2NR_{4'''}R_{4''''}$ optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', or I'' the compound is a compound, wherein $R_4$, $R_{4'}$ and $R_{4''}$ are independently selected from hydrogen or substituted or unsubstituted $C_{1-6}$ alkyl, substituted or unsubstituted $C_{2-6}$ alkenyl or substituted or unsubstituted $C_{2-6}$ alkynyl, substituted or unsubstituted $C_{3-6}$ cycloalkyl;

wherein the cycloalkyl in $R_4$ $R_{4'}$ or $R_{4''}$ if substituted is substituted with substituents selected from —$R_{4''''}$, halogen, —$SR_{4''''}$, —CN, haloalkyl, —$NR_{4'''}R_{4''''}$, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formulas I, I', or I'' the compound is a compound, wherein $R_4$, $R_{4'}$ and $R_{4''}$ are independently selected from hydrogen or substituted or unsubstituted $C_{1-6}$ alkyl, substituted or unsubstituted $C_{2-6}$ alkenyl or substituted or unsubstituted $C_{2-6}$ alkynyl, substituted or unsubstituted $C_{3-6}$ cycloalkyl;

wherein the alkyl, alkenyl and alkynyl in $R_4$ $R_{4'}$ or $R_{4''}$ if substituted are substituted with substituents selected from halogen, —CN, haloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In one preferred further embodiment, the compounds of the general formula I are selected from

| Ex | Chemical name |
|---|---|
| 1 | 12-ethyl-8-{2-[3-(trifluoromethyl)pyridin-2-yl]ethyl}-4-oxa-8,12-diazadispiro[2.1.5.3]tridecan-13-one |
| 2 | 12-ethyl-8-{2-[6-(trifluoromethyl)pyridin-2-yl]ethyl}-4-oxa-8,12-diazadispiro[2.1.5.3]tridecan-13-one |
| 3 | 12-ethyl-8-[2-(3-fluoropyridin-2-yl)ethyl]-4-oxa-8,12-diazadispiro[2.1.5.3]tridecan-13-one |
| 4 | 12-ethyl-8-{2-[4-(trifluoromethyl)pyridin-2-yl]ethyl}-4-oxa-8,12-diazadispiro[2.1.5.3]tridecan-13-one |
| 5 | 8-[2-(3-chloropyridin-2-yl)ethyl]-12-ethyl-4-oxa-8,12-diazadispiro[2.1.5.3]tridecan-13-one |
| 6 | 8-[2-(6-aminopyridin-2-yl)ethyl]-12-ethyl-4-oxa-8,12-diazadispiro[2.1.5.3]tridecan-13-one |
| 7 | 12-ethyl-8-phenethyl-4-oxa-8,12-diazadispiro[2.1.5.3]tridecan-13-one |
| 8 | 12-isopropyl-8-phenethyl-4-oxa-8,12-diazadispiro[2.1.5.3]tridecan-13-one |
| 9 | 12-isopropyl-8-[2-(pyridin-2-yl)ethyl]-4-oxa-8,12-diazadispiro[2.1.5.3]tridecan-13-one dihydrochloride |
| 10 | 12-ethyl-8-[2-(pyridin-2-yl)ethyl]-4-oxa-8,12-diazadispiro[2.1.5.3]tridecan-13-one |
| 11 | (R)-2,4-dimethyl-9-phenethyl-1-oxa-4,9-diazaspiro[5.5]undecan-3-one |
| 12 | 12-ethyl-8-{2-[6-(trifluoromethyl)pyridin-3-yl]ethyl}-4-oxa-8,12-diazadispiro[2.1.5.3]tridecan-13-one |
| 13 | 12-ethyl-8-[2-(6-methoxypyridin-2-yl)ethyl]-4-oxa-8,12-diazadispiro[2.1.5.3]tridecan-13-one |
| 14 | 12-ethyl-8-[2-(6-hydroxypyridin-2-yl)ethyl]-4-oxa-8,12-diazadispiro[2.1.5.3]tridecan-13-one |
| 15 | 4-(2-{12-ethyl-13-oxo-4-oxa-8,12-diazadispiro[2.1.5.3]tridecan-8-yl}ethyl)benzene-1-sulfonamide |
| 16 | 4-(2-{12-ethyl-13-oxo-4-oxa-8,12-diazadispiro[2.1.5.3]tridecan-8-yl}ethyl)-N-methylbenzene-1-sulfonamide |
| 17 | 12-ethyl-8-{2-[3-(trifluoromethoxy)phenyl]ethyl}-4-oxa-8,12-diazadispiro[2.1.5.3]tridecan-13-one |
| 18 | (R)-4-ethyl-2-methyl-9-phenethyl-1-oxa-4,9-diazaspiro[5.5]undecan-3-one |
| 19 | 12-ethyl-8-(3-nitrophenethyl)-4-oxa-8,12-diazadispiro[2.1.5.3]tridecan-13-one |
| 20 | 12-ethyl-8-(3-methoxyphenethyl)-4-oxa-8,12-diazadispiro[2.1.5.3]tridecan-13-one |
| 21 | tert-butyl (4-(2-(12-ethyl-13-oxo-4-oxa-8,12-diazadispiro[2.1.5.3]tridecan-8-yl)ethyl)thiazol-2-yl)carbamate |
| 22 | methyl 4-(2-{12-ethyl-13-oxo-4-oxa-8,12-diazadispiro[2.1.5.3]tridecan-8-yl}ethyl)benzoate |
| 23 | 12-ethyl-8-[2-(pyridin-4-yl)ethyl]-4-oxa-8,12-diazadispiro[2.1.5.3]tridecan-13-one |
| 24 | 12-ethyl-8-[2-(pyridin-3-yl)ethyl]-4-oxa-8,12-diazadispiro[2.1.5.3]tridecan-13-one |
| 25 | 12-ethyl-8-(4-methoxyphenethyl)-4-oxa-8,12-diazadispiro[2.1.5.3]tridecan-13-one |
| 26 | 12-ethyl-8-(2-methoxyphenethyl)-4-oxa-8,12-diazadispiro[2.1.5.3]tridecan-13-one |
| 27 | 3-(2-{12-ethyl-13-oxo-4-oxa-8,12-diazadispiro[2.1.5.3]tridecan-8-yl}ethyl)benzonitrile |
| 28 | 4-(2-{12-ethyl-13-oxo-4-oxa-8,12-diazadispiro[2.1.5.3]tridecan-8-yl}ethyl)-N,N-dimethylbenzamide |
| 29 | 8-[2-fluorophenethyl]-12-methyl-4-oxa-8,12-diazadispiro[2.1.5.3]tridecan-13-one |

| Ex | Chemical name |
|---|---|
| 30 | 8-[2-fluorophenethyl]-12-isopropyl-4-oxa-8,12-diazadispiro[2.1.5.3]tridecan-13-one |
| 31 | (R)-2-isopropyl-4-methyl-9-phenethyl-1-oxa-4,9-diazaspiro[5.5]undecan-3-one |
| 32 | (R)-4-ethyl-9-(2-fluorophenethyl)-2-methyl-1-oxa-4,9-diazaspiro[5.5]undecan-3-one |
| 33 | (R)-2-ethyl-4-methyl-9-phenethyl-1-oxa-4,9-diazaspiro[5.5]undecan-3-one |
| 34 | (R)-9-(3-fluorophenethyl)-4-isopropyl-2-methyl-1-oxa-4,9-diazaspiro[5.5]undecan-3-one |
| 35 | (R)-4-cyclopropyl-9-(2-fluorophenethyl)-2-methyl-1-oxa-4,9-diazaspiro[5.5]undecan-3-one |
| 36 | (R)-4-isopropyl-2-methyl-9-phenethyl-1-oxa-4,9-diazaspiro[5.5]undecan-3-one |
| 37 | (R)-9-(2-fluorophenethyl)-2,4-dimethyl-1-oxa-4,9-diazaspiro[5.5]undecan-3-one |
| 38 | (R)-9-(3-fluorophenethyl)-2,4-dimethyl-1-oxa-4,9-diazaspiro[5.5]undecan-3-one |
| 39 | (R)-9-(2-fluorophenethyl)-4-isopropyl-2-methyl-1-oxa-4,9-diazaspiro[5.5]undecan-3-one |
| 40 | (R)-4-cyclopropyl-2-methyl-9-phenethyl-1-oxa-4,9-diazaspiro[5.5]undecan-3-one |
| 41 | (R)-4-cyclopropyl-9-(3-fluorophenethyl)-2-methyl-1-oxa-4,9-diazaspiro[5.5]undecan-3-one |
| 42 | (R)-4-ethyl-9-(3-fluorophenethyl)-2-methyl-1-oxa-4,9-diazaspiro[5.5]undecan-3-one |
| 43 | 8-(3-fluorophenethyl)-12-isopropyl-4-oxa-8,12-diazadispiro[2.1.5.3]tridecan-13-one hydrochloride |
| 44 | (R)-2,4-dimethyl-9-(3-(trifluoromethyl)phenethyl)-1-oxa-4,9-diazaspiro[5.5]undecan-3-one |
| 45 | (R)-2,4-dimethyl-9-(2-(trifluoromethoxy)phenethyl)-1-oxa-4,9-diazaspiro[5.5]undecan-3-one |
| 46 | (R)-9-(2-fluorophenethyl)-2-isopropyl-4-methyl-1-oxa-4,9-diazaspiro[5.5]undecan-3-one |
| 47 | (R)-9-(3-fluorophenethyl)-2-isopropyl-4-methyl-1-oxa-4,9-diazaspiro[5.5]undecan-3-one |
| 48 | (R)-2,4-dimethyl-9-(2-(trifluoromethyl)phenethyl)-1-oxa-4,9-diazaspiro[5.5]undecan-3-one |
| 49 | (R)-9-(2,6-difluorophenethyl)-4-isopropyl-2-methyl-1-oxa-4,9-diazaspiro[5.5]undecan-3-one |
| 50 | (R)-9-(2,5-difluorophenethyl)-4-isopropyl-2-methyl-1-oxa-4,9-diazaspiro[5.5]undecan-3-one |
| 51 | (R)-9-(2,3-difluorophenethyl)-4-isopropyl-2-methyl-1-oxa-4,9-diazaspiro[5.5]undecan-3-one |
| 52 | (R)-2-ethyl-9-(2-fluorophenethyl)-4-methyl-1-oxa-4,9-diazaspiro[5.5]undecan-3-one |
| 53 | (R)-2-ethyl-9-(3-fluorophenethyl)-4-methyl-1-oxa-4,9-diazaspiro[5.5]undecan-3-one |
| 54 | 2,2,4-trimethyl-9-phenethyl-1-oxa-4,9-diazaspiro[5.5]undecan-3-one |
| 55 | 12-methyl-8-phenethyl-4-oxa-8,12-diazadispiro[2.1.5.3]tridecan-13-one |
| 56 | 8-(3-aminophenethyl)-12-ethyl-4-oxa-8,12-diazadispiro[2.1.5.3]tridecan-13-one |
| 57 | N-[3-(2-{12-ethyl-13-oxo-4-oxa-8,12-diazadispiro[2.1.5.3]tridecan-8-yl}ethyl)phenyl]acetamide |
| 58 | [3-(2-{12-ethyl-13-oxo-4-oxa-8,12-diazadispiro[2.1.5.3]tridecan-8-yl}ethyl)phenyl]urea |
| 59 | 4-(2-{12-ethyl-13-oxo-4-oxa-8,12-diazadispiro[2.1.5.3]tridecan-8-yl}ethyl)-N-methylbenzamide |
| 60 | 12-ethyl-8-(2-hydroxyphenethyl)-4-oxa-8,12-diazadispiro[2.1.5.3]tridecan-13-one |
| 61 | 12-ethyl-8-(3-hydroxyphenethyl)-4-oxa-8,12-diazadispiro[2.1.5.3]tridecan-13-one |
| 62 | 12-ethyl-8-(4-hydroxyphenethyl)-4-oxa-8,12-diazadispiro[2.1.5.3]tridecan-13-one hydrochloride, or |
| 63 | 8-[2-(2-aminothiazol-4-yl)ethyl]-12-ethyl-4-oxa-8,12-diazadispiro[2.1.5.3]tridecan-13-one; | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred further embodiment, the compounds of the general formula I are selected from

| Ex | Chemical name |
|---|---|
| 1 | 12-ethyl-8-{2-[3-(trifluoromethyl)pyridin-2-yl]ethyl}-4-oxa-8,12-diazadispiro[2.1.5.3]tridecan-13-one |
| 2 | 12-ethyl-8-{2-[6-(trifluoromethyl)pyridin-2-yl]ethyl}-4-oxa-8,12-diazadispiro[2.1.5.3]tridecan-13-one |

| Ex | Chemical name |
|---|---|
| 3 | 12-ethyl-8-[2-(3-fluoropyridin-2-yl)ethyl]-4-oxa-8,12-diazadispiro[2.1.5.3]tridecan-13-one |
| 4 | 12-ethyl-8-{2-[4-(trifluoromethyl)pyridin-2-yl]ethyl}-4-oxa-8,12-diazadispiro[2.1.5.3]tridecan-13-one |
| 5 | 8-[2-(3-chloropyridin-2-yl)ethyl]-12-ethyl-4-oxa-8,12-diazadispiro[2.1.5.3]tridecan-13-one |
| 6 | 8-[2-(6-aminopyridin-2-yl)ethyl]-12-ethyl-4-oxa-8,12-diazadispiro[2.1.5.3]tridecan-13-one |
| 7 | 12-ethyl-8-phenethyl-4-oxa-8,12-diazadispiro[2.1.5.3]tridecan-13-one |
| 8 | 12-isopropyl-8-phenethyl-4-oxa-8,12-diazadispiro[2.1.5.3]tridecan-13-one |
| 9 | 12-isopropyl-8-[2-(pyridin-2-yl)ethyl]-4-oxa-8,12-diazadispiro[2.1.5.3]tridecan-13-one dihydrochloride |
| 10 | 12-ethyl-8-[2-(pyridin-2-yl)ethyl]-4-oxa-8,12-diazadispiro[2.1.5.3]tridecan-13-one |
| 11 | (R)-2,4-dimethyl-9-phenethyl-1-oxa-4,9-diazaspiro[5.5]undecan-3-one |
| 12 | 12-ethyl-8-{2-[6-(trifluoromethyl)pyridin-3-yl]ethyl}-4-oxa-8,12-diazadispiro[2.1.5.3]tridecan-13-one |
| 13 | 12-ethyl-8-[2-(6-methoxypyridin-2-yl)ethyl]-4-oxa-8,12-diazadispiro[2.1.5.3]tridecan-13-one |
| 14 | 12-ethyl-8-[2-(6-hydroxypyridin-2-yl)ethyl]-4-oxa-8,12-diazadispiro[2.1.5.3]tridecan-13-one |
| 15 | 4-(2-{12-ethyl-13-oxo-4-oxa-8,12-diazadispiro[2.1.5.3]tridecan-8-yl}ethyl)benzene-1-sulfonamide |
| 16 | 4-(2-{12-ethyl-13-oxo-4-oxa-8,12-diazadispiro[2.1.5.3]tridecan-8-yl}ethyl)-N-methylbenzene-1-sulfonamide |
| 17 | 12-ethyl-8-{2-[3-(trifluoromethoxy)phenyl]ethyl}-4-oxa-8,12-diazadispiro[2.1.5.3]tridecan-13-one |
| 18 | (R)-4-ethyl-2-methyl-9-phenethyl-1-oxa-4,9-diazaspiro[5.5]undecan-3-one |
| 19 | 12-ethyl-8-(3-nitrophenethyl)-4-oxa-8,12-diazadispiro[2.1.5.3]tridecan-13-one |
| 20 | 12-ethyl-8-(3-methoxyphenethyl)-4-oxa-8,12-diazadispiro[2.1.5.3]tridecan-13-one |
| 21 | tert-butyl (4-(2-(12-ethyl-13-oxo-4-oxa-8,12-diazadispiro[2.1.5.3]tridecan-8-yl)ethyl)thiazol-2-yl)carbamate |
| 22 | methyl 4-(2-{12-ethyl-13-oxo-4-oxa-8,12-diazadispiro[2.1.5.3]tridecan-8-yl}ethyl)benzoate |
| 23 | 12-ethyl-8-[2-(pyridin-4-yl)ethyl]-4-oxa-8,12-diazadispiro[2.1.5.3]tridecan-13-one |
| 24 | 12-ethyl-8-[2-(pyridin-3-yl)ethyl]-4-oxa-8,12-diazadispiro[2.1.5.3]tridecan-13-one |
| 25 | 12-ethyl-8-(4-methoxyphenethyl)-4-oxa-8,12-diazadispiro[2.1.5.3]tridecan-13-one |
| 26 | 12-ethyl-8-(2-methoxyphenethyl)-4-oxa-8,12-diazadispiro[2.1.5.3]tridecan-13-one |
| 27 | 3-(2-{12-ethyl-13-oxo-4-oxa-8,12-diazadispiro[2.1.5.3]tridecan-8-yl}ethyl)benzonitrile |
| 28 | 4-(2-{12-ethyl-13-oxo-4-oxa-8,12-diazadispiro[2.1.5.3]tridecan-8-yl}ethyl)-N,N-dimethylbenzamide |
| 29 | 8-[2-fluorophenethyl]-12-methyl-4-oxa-8,12-diazadispiro[2.1.5.3]tridecan-13-one |
| 30 | 8-[2-fluorophenethyl]-12-isopropyl-4-oxa-8,12-diazadispiro[2.1.5.3]tridecan-13-one |
| 31 | (R)-2-isopropyl-4-methyl-9-phenethyl-1-oxa-4,9-diazaspiro[5.5]undecan-3-one |
| 32 | (R)-4-ethyl-9-(2-fluorophenethyl)-2-methyl-1-oxa-4,9-diazaspiro[5.5]undecan-3-one |
| 33 | (R)-2-ethyl-4-methyl-9-phenethyl-1-oxa-4,9-diazaspiro[5.5]undecan-3-one |
| 34 | (R)-9-(3-fluorophenethyl)-4-isopropyl-2-methyl-1-oxa-4,9-diazaspiro[5.5]undecan-3-one |
| 35 | (R)-4-cyclopropyl-9-(2-fluorophenethyl)-2-methyl-1-oxa-4,9-diazaspiro[5.5]undecan-3-one |
| 36 | (R)-4-isopropyl-2-methyl-9-phenethyl-1-oxa-4,9-diazaspiro[5.5]undecan-3-one |
| 37 | (R)-9-(2-fluorophenethyl)-2,4-dimethyl-1-oxa-4,9-diazaspiro[5.5]undecan-3-one |
| 38 | (R)-9-(3-fluorophenethyl)-2,4-dimethyl-1-oxa-4,9-diazaspiro[5.5]undecan-3-one |
| 39 | (R)-9-(2-fluorophenethyl)-4-isopropyl-2-methyl-1-oxa-4,9-diazaspiro[5.5]undecan-3-one |
| 40 | (R)-4-cyclopropyl-2-methyl-9-phenethyl-1-oxa-4,9-diazaspiro[5.5]undecan-3-one |
| 41 | (R)-4-cyclopropyl-9-(3-fluorophenethyl)-2-methyl-1-oxa-4,9-diazaspiro[5.5]undecan-3-one |
| 42 | (R)-4-ethyl-9-(3-fluorophenethyl)-2-methyl-1-oxa-4,9-diazaspiro[5.5]undecan-3-one |
| 43 | 8-(3-fluorophenethyl)-12-isopropyl-4-oxa-8,12-diazadispiro[2.1.5.3]tridecan-13-one hydrochloride |
| 44 | (R)-2,4-dimethyl-9-(3-(trifluoromethyl)phenethyl)-1-oxa-4,9-diazaspiro[5.5]undecan-3-one |
| 45 | (R)-2,4-dimethyl-9-(2-(trifluoromethoxy)phenethyl)-1-oxa-4,9-diazaspiro[5.5]undecan-3-one |
| 46 | (R)-9-(2-fluorophenethyl)-2-isopropyl-4-methyl-1-oxa-4,9-diazaspiro[5.5]undecan-3-one |
| 47 | (R)-9-(3-fluorophenethyl)-2-isopropyl-4-methyl-1-oxa-4,9-diazaspiro[5.5]undecan-3-one |
| 48 | (R)-2,4-dimethyl-9-(2-(trifluoromethyl)phenethyl)-1-oxa-4,9-diazaspiro[5.5]undecan-3-one |

-continued

| Ex | Chemical name |
|---|---|
| 49 | (R)-9-(2,6-difluorophenethyl)-4-isopropyl-2-methyl-1-oxa-4,9-diazaspiro[5.5]undecan-3-one |
| 50 | (R)-9-(2,5-difluorophenethyl)-4-isopropyl-2-methyl-1-oxa-4,9-diazaspiro[5.5]undecan-3-one |
| 51 | (R)-9-(2,3-difluorophenethyl)-4-isopropyl-2-methyl-1-oxa-4,9-diazaspiro[5.5]undecan-3-one |
| 52 | (R)-2-ethyl-9-(2-fluorophenethyl)-4-methyl-1-oxa-4,9-diazaspiro[5.5]undecan-3-one |
| 53 | (R)-2-ethyl-9-(3-fluorophenethyl)-4-methyl-1-oxa-4,9-diazaspiro[5.5]undecan-3-one |
| 54 | 2,2,4-trimethyl-9-phenethyl-1-oxa-4,9-diazaspiro[5.5]undecan-3-one |
| 55 | 12-methyl-8-phenethyl-4-oxa-8,12-diazadispiro[2.1.5.3]tridecan-13-one |
| 56 | 8-(3-aminophenethyl)-12-ethyl-4-oxa-8,12-diazadispiro[2.1.5.3]tridecan-13-one |
| 57 | N-[3-(2-{12-ethyl-13-oxo-4-oxa-8,12-diazadispiro[2.1.5.3]tridecan-8-yl}ethyl)phenyl]acetamide |
| 58 | [3-(2-{12-ethyl-13-oxo-4-oxa-8,12-diazadispiro[2.1.5.3]tridecan-8-yl}ethyl)phenyl]urea |
| 59 | 4-(2-{12-ethyl-13-oxo-4-oxa-8,12-diazadispiro[2.1.5.3]tridecan-8-yl}ethyl)-N-methylbenzamide |
| 60 | 12-ethyl-8-(2-hydroxyphenethyl)-4-oxa-8,12-diazadispiro[2.1.5.3]tridecan-13-one |
| 61 | 12-ethyl-8-(3-hydroxyphenethyl)-4-oxa-8,12-diazadispiro[2.1.5.3]tridecan-13-one |
| 62 | 12-ethyl-8-(4-hydroxyphenethyl)-4-oxa-8,12-diazadispiro[2.1.5.3] tridecan-13-one hydrochloride |
| 63 | 8-[2-(2-aminothiazol-4-yl)ethyl]-12-ethyl-4-oxa-8,12-diazadispiro[2.1.5.3]tridecan-13-one |
| 64 | 2,2-diethyl-4-methyl-9-phenethyl-1-oxa-4,9-diazaspiro[5.5]undecan-3-one |
| 65 | 4-cyclopropyl-9-(2-fluorophenethyl)-2,2-dimethyl-1-oxa-4,9-diazaspiro[5.5]undecan-3-one |
| 66 | 8-(2,5-difluorophenethyl)-12-isopropyl-4-oxa-8,12-diazadispiro[2.1.5.3]tridecan-13-one |
| 67 | 8-(2,3-difluorophenethyl)-12-isopropyl-4-oxa-8,12-diazadispiro[2.1.5.3]tridecan-13-one |
| 68 | 10-(2-fluorophenethyl)-14-methyl-6-oxa-10,14-diazadispiro[4.1.5.3]pentadecan-15-one |
| 69 | 10-(3-fluorophenethyl)-14-methyl-6-oxa-10,14-diazadispiro[4.1.5.3]pentadecan-15-one |
| 70 | (R)-9-(2,5-difluorophenethyl)-4-ethyl-2-methyl-1-oxa-4,9-diazaspiro[5.5]undecan-3-one |
| 71 | 8-(2,5-difluorophenethyl)-12-ethyl-4-oxa-8,12-diazadispiro[2.1.5.3]tridecan-13-one |
| 72 | 12-ethyl-8-(3-fluorophenethyl)-4-oxa-8,12-diazadispiro[2.1.5.3]tridecan-13-one |
| 73 | 12-ethyl-8-(2-fluorophenethyl)-4-oxa-8,12-diazadispiro[2.1.5.3]tridecan-13-one |
| 74 | (R)-9-(2,3-difluorophenethyl)-2,4-dimethyl-1-oxa-4,9-diazaspiro[5.5]undecan-3-one |
| 75 | (R)-2,4-diethyl-9-(2-fluorophenethyl)-1-oxa-4,9-diazaspiro[5.5]undecan-3-one |
| 76 | (R)-2,4-diethyl-9-(3-fluorophenethyl)-1-oxa-4,9-diazaspiro[5.5]undecan-3-one |
| 77 | (R)-2-ethyl-9-(3-fluorophenethyl)-4-isopropyl-1-oxa-4,9-diazaspiro[5.5]undecan-3-one |
| 78 | 4-ethyl-9-(3-fluorophenethyl)-2,2-dimethyl-1-oxa-4,9-diazaspiro[5.5]undecan-3-one |
| 79 | 4-ethyl-9-(2-fluorophenethyl)-2,2-dimethyl-1-oxa-4,9-diazaspiro[5.5]undecan-3-one |
| 80 | (R)-2-ethyl-9-(2-fluorophenethyl)-4-isopropyl-1-oxa-4,9-diazaspiro[5.5]undecan-3-one |
| 81 | (R)-9-(2,5-difluorophenethyl)-2,4-dimethyl-1-oxa-4,9-diazaspiro[5.5]undecan-3-one |
| 82 | 9-(3-fluorophenethyl)-4-isopropyl-2,2-dimethyl-1-oxa-4,9-diazaspiro[5.5]undecan-3-one |
| 83 | 9-(2-fluorophenethyl)-4-isopropyl-2,2-dimethyl-1-oxa-4,9-diazaspiro[5.5]undecan-3-one |
| 84 | 9-(2,3-difluorophenethyl)-4-isopropyl-2,2-dimethyl-1-oxa-4,9-diazaspiro[5.5]undecan-3-one |
| 85 | 4-cyclopropyl-9-(2,3-difluorophenethyl)-2,2-dimethyl-1-oxa-4,9-diazaspiro[5.5]undecan-3-one |
| 86 | 4-cyclopropyl-9-(2,5-difluorophenethyl)-2,2-dimethyl-1-oxa-4,9-diazaspiro[5.5]undecan-3-one |
| 87 | (R)-9-(2,3-difluorophenethyl)-4-ethyl-2-methyl-1-oxa-4,9-diazaspiro[5.5]undecan-3-one |
| 88 | 9-(2,5-difluorophenethyl)-4-ethyl-2,2-dimethyl-1-oxa-4,9-diazaspiro[5.5]undecan-3-one |
| 89 | 9-(2,3-difluorophenethyl)-4-ethyl-2,2-dimethyl-1-oxa-4,9-diazaspiro[5.5]undecan-3-one |
| 90 | 9-(2,5-difluorophenethyl)-4-isopropyl-2,2-dimethyl-1-oxa-4,9-diazaspiro[5.5]undecan-3-one |
| 91 | (R)-4-cyclopropyl-9-(2,3-difluorophenethyl)-2-methyl-1-oxa-4,9-diazaspiro[5.5]undecan-3-one |

| Ex | Chemical name |
|---|---|
| 92 | (R)-4-cyclopropyl-9-(2,5-difluorophenethyl)-2-methyl-1-oxa-4,9-diazaspiro[5.5]undecan-3-one |
| 93 | (R)-4-methyl-9-phenethyl-2-(prop-2-yn-1-yl)-1-oxa-4,9-diazaspiro[5.5]undecan-3-one |
| 94 | (R)-2-(2-hydroxyethyl)-4-methyl-9-phenethyl-1-oxa-4,9-diazaspiro[5.5]undecan-3-one, or |
| 95 | (R)-2-benzyl-4-methyl-9-phenethyl-1-oxa-4,9-diazaspiro[5.5]undecan-3-one: | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another very preferred embodiment of the compound according to the invention according to general formula I' the compound is selected from examples 1 to 10, 12 to 17, 19 to 30, 43, and 55 to 63, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another very preferred embodiment of the compound according to the invention according to general formula I' the compound is selected from examples 1 to 10, 12 to 17, 19 to 30, 43, 55 to 63, 66, 67, and 71 to 73; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formula I" the compound is selected from examples 11, 18, 31 to 42, and 44 to 53, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt.

In another preferred embodiment of the compound according to the invention according to general formula I" the compound is selected from examples 11, 18, 31 to 42, 44 to 53, 70, 74 to 77, 80, 81, 87, 91-94; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt.

As this invention is aimed at providing a compound or a chemically related series of compounds which act as dual ligands of the $\sigma_1$ receptor and the µ-opioid receptor a very preferred embodiment in which the compounds are selected which act as dual ligands of the $\sigma_1$ receptor and the µ-opioid receptor and especially compounds which have a binding expressed as $K_i$ which is preferably <1000 nM for both receptors, more preferably <500 nM, even more preferably <100 nM.

In the following the phrase "compound of the invention" is used. This is to be understood as any compound according to the invention as described above according to general formulas I, I' or I".

The compounds of the invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

As a further general remark, the use of "comprising" and "comprises" as used herein, especially when defining the steps of a process is to be understood as also disclosing "consisting of" and "consists of" respectively etc. Thus, this also includes that the steps of the respective process are then to be also understood to be limited to the steps preceded by this "comprising" or "comprises" etc.

A preferred aspect of the invention is also a process for the production of a compound according to formula I,

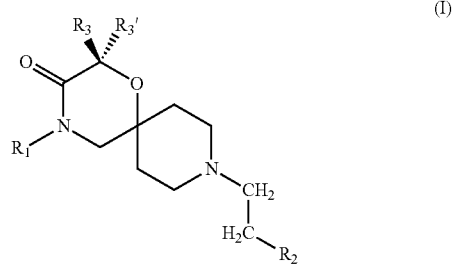

wherein $R_1$, $R_2$, $R_3$ and $R_{3'}$ are as already defined in the description wherein a compound of formula VIIIH or its suitable salt like the hydrochloride

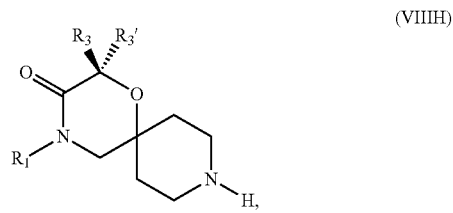

wherein $R_1$, $R_3$ and $R_{3'}$ are already defined above in the description, is reacted with a compound according to formula IX, X or XI.

-continued (X)

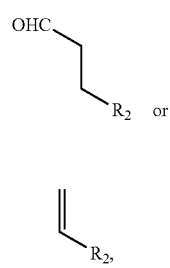

or (XI)

wherein $R_2$ is as already defined above in the description, and wherein LG is a leaving group, leading to a compound according to formula (I)

A particular embodiment is a process for the preparation of a compound of general formula I (I)

wherein $R_1$, $R_2$, $R_3$ and $R_{3'}$ are as already defined in the description;

which comprises the steps of (a) Reacting a compound of formula V (V)

with a compound of formula VI (VI)

wherein W and LG are leaving groups, $R_3$ and $R_{3'}$ are as already defined in the description;

to obtain a compound of formula VII

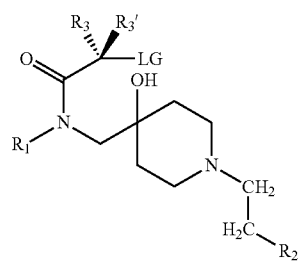

(VII)

wherein LG is a leaving group, $R_3$ and $R_{3'}$ are as already defined in the description;

and (b) Carrying out a cyclisation of the resulting compound in a suitable solvent, in the presence of a strong base and at a temperature comprised between −78° C. and the reflux temperature;

Another particular embodiment of the invention is a process for the preparation of a compound of general formula I'

(I')

wherein q is 1, 2, 3 or 4 and $R_1$ and $R_2$ are as defined in the description;

which comprises the steps of (a) reacting a compound of formula V (V)

wherein $R_1$ and $R_2$ are as defined in the description;
with a compound of formula XX (XX)

wherein W and LG are leaving groups, q is as defined in the description;
to obtain a compound of formula XXI

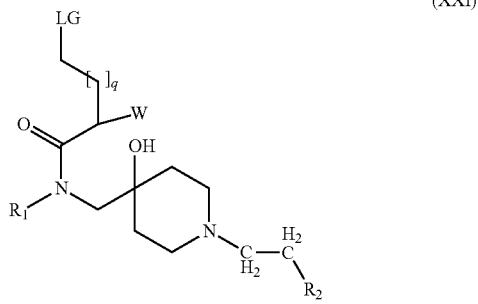

(XXI)

wherein W and LG are leaving groups, $R_2$ and q are as defined in the description (b) Carrying out a cyclisation of the resulting compound in a suitable solvent, in the presence of a strong base and at a temperature comprised between −78° C. and the reflux temperature; leading to a compound of formula XXII,

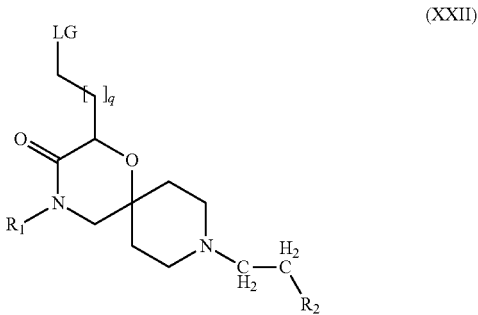

(XXII)

(c) and treating with a strong base such as lithium diisopropylamide or potassium tert-butoxide, in an aprotic solvent such as tetrahydrofuran, at a suitable temperature, preferably cooling.

Preparation of the HCl salt: To a solution of the free base obtained, in a suitable solvent, preferably in anhydrous diethyl ether, HCl was added, and the mixture was stirred, preferably at room temperature, preferably for 1 h. The solvent was evaporated, preferably under vacuum, to give the corresponding HCl salt.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formulas I, I', or I" or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

As a general remark, the use of "comprising" and "comprises" as used herein, especially when defining the contents of a medicament or a pharmaceutical formulation is to be understood as also disclosing "consisting of" and "consists of" respectively etc. Thus, this also includes that the contents of the respective medicament or pharmaceutical formulation are then to be also understood to be limited to the exact contents preceded by this "comprising" or "comprises" etc.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy.

The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formulas I, I', or I" or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis)

Scheme 1:

A 4-step process is described for the preparation of compounds of general formula (I) starting from a ketone of formula II, as shown in the following scheme:

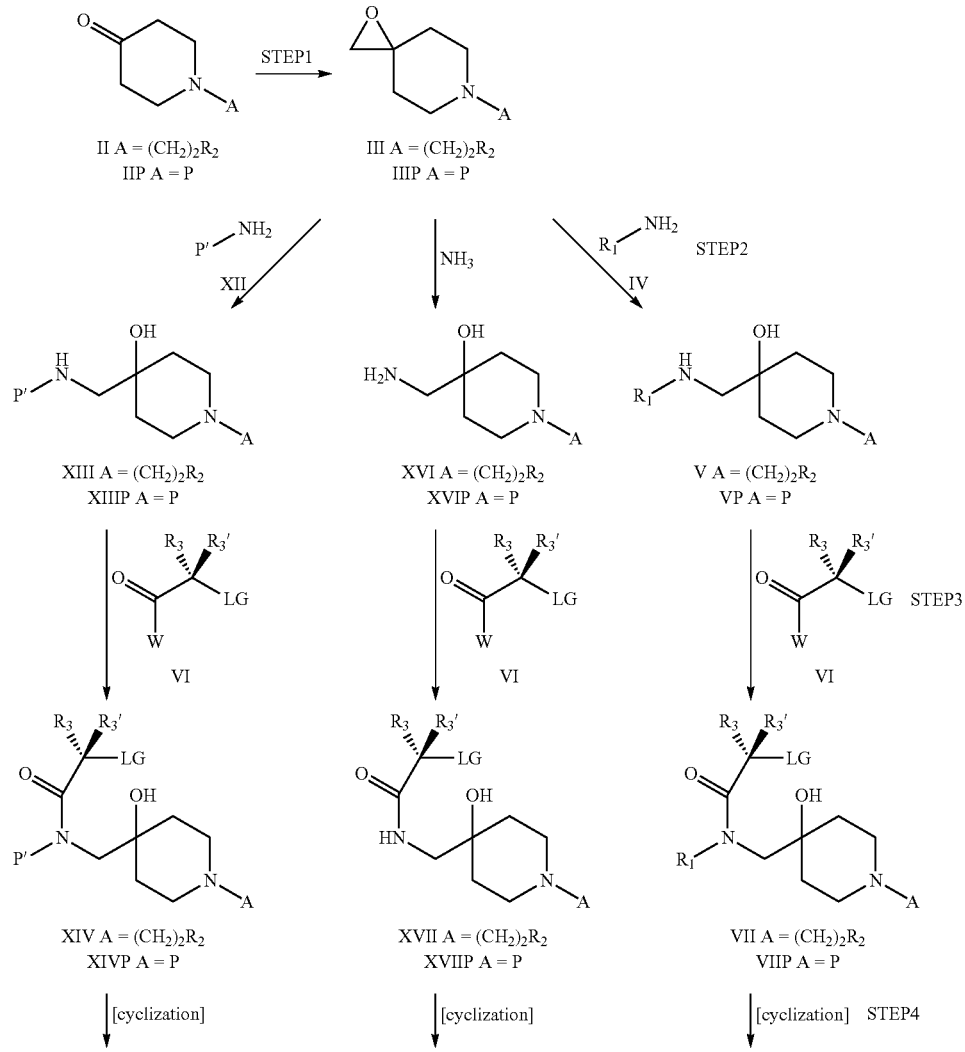

Scheme 1

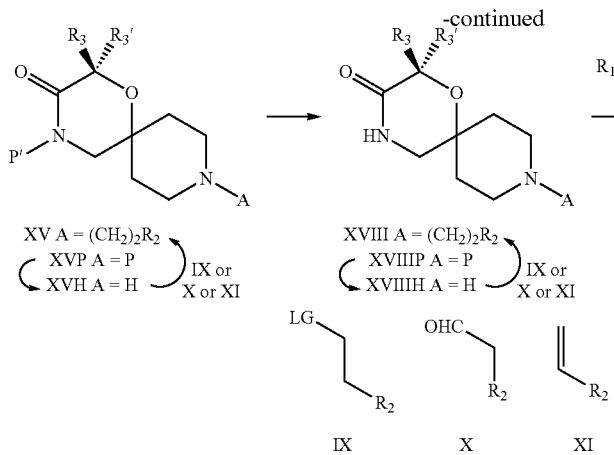
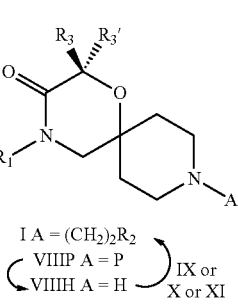

wherein $R_1$, $R_2$, $R_3$ and $R_{3'}$ have the meanings as defined above for a compound of formula (I), W represents a leaving group such as chloro or bromo, LG represents another leaving group such as halogen, mesylate, tosylate or triflate, P represents a suitable protecting group (preferably Boc) and P' represents another suitable protecting group (preferably 4-methoxybenzyl).

The 4 step-process is carried out as described below:

Step1:

A compound of formula III is prepared by treating a compound of formula II with a suitable methyl-transfer reagent such as trimethylsulfoxonium iodide or trimethylsulfonium iodide, in a suitable aprotic solvent such as dimethylsulfoxide, and in the presence of a strong base such as sodium hydride or potassium tert-butoxide, at a suitable temperature, preferably comprised between room temperature and 60° C.

Step2:

A compound of formula V is prepared by reacting a compound of formula III with an amine of formula IV, in a suitable solvent such as an alcohol, preferably ethanol-water mixtures, at a suitable temperature comprised between room temperature and the reflux temperature, preferably at room temperature.

Step3:

A compound of formula VII is prepared by reacting a compound of formula V with an acylating agent of formula VI. The acylation reaction is carried out in a suitable solvent, such as dichloromethane or ethyl acetate-water mixtures; in the presence of an organic base such as triethylamine or diisopropylethylamine or an inorganic base such as $K_2CO_3$; and at a suitable temperature, preferably comprised between −78° C. and room temperature.

Step4:

The intramolecular cyclization of a compound of formula VII renders a compound of formula (I). The cyclization reaction is carried out in a suitable solvent, such as tetrahydrofuran; in the presence of a strong base such as potassium tert-butoxide or sodium hydride; and at a suitable temperature, comprised between −78° C. and room temperature, preferably cooling.

Alternatively, the group $CH_2CH_2R_2$ can be incorporated in the last step of the synthesis by reaction of a compound of formula VIIIH with a compound of formula IX, X or XI, as shown in Scheme 1. A compound of formula VIIIH is obtained by deprotection of a compound of formula VIIIP, wherein P represents a suitable protecting group, preferably Boc (tert-butoxycarbonyl). When the protecting group is Boc, the deprotection can be conducted by adding a solution of a strong acid such as HCl, in a suitable solvent such as diethyl ether, 1,4-dioxane or methanol, or with trifluoroacetic acid in dichloromethane. A compound of formula VIIIP is prepared from a compound of formula IIP following the same sequence described for the synthesis of compounds of formula (I).

The alkylation reaction between a compound of formula VIIIH (or a suitable salt such as trifluoroacetate or hydrochloride) and a compound of formula IX is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$; at a suitable temperature comprised between room temperature and the reflux temperature, preferably heating, or alternatively, the reactions can be carried out in a microwave reactor. Additionally, an activating agent such as NaI can be used.

The reductive amination reaction between a compound of formula VIIIH and a compound of formula X is carried out in the presence of a reductive reagent, preferably sodium triacetoxyborohydride, in an aprotic solvent, preferably tetrahydrofuran or dichloroethane, optionally in the presence of an acid, preferably acetic acid.

The condensation reaction between a compound of general formula VIIIH and a compound of formula XI is preferably carried out in a suitable solvent, such as isopropanol, n-butanol or 2-methoxyethanol, optionally in the presence of an organic base such as triethylamine or diisopropylethylamine, at a suitable temperature comprised between room temperature and the reflux temperature, preferably heating, or alternatively, the reactions can be carried out in a microwave reactor.

In another alternative approach, the $R_1$ substituent can be incorporated later in the sequence by the reaction of a compound of formula XVIII with a compound of formula XIX. The alkylation reaction is carried out in an aprotic solvent, preferably dimethylformamide, in the presence of an inorganic base such as NaH, at a suitable temperature, preferably between room temperature and 60° C.

A compound of formula XVIII is synthesized following an analogous sequence as described for the synthesis of compounds of formula I, but effecting step 2 using ammonia instead of an amine. Alternatively, a compound of formula XVIII can be prepared by reaction of a compound of formula XVIIIH (prepared from a compound of formula XVIIIP, wherein P represents a suitable protecting group) with a compound of formula IX, X or XI, as described above.

Additionally, a compound of formula XVIII can be prepared from a compound of formula XV, wherein P' represents a suitable protecting group, preferably a 4-methoxybenzyl group. The deprotection reaction is carried out with cerium ammonium nitrate in a suitable solvent such as mixtures of acetonitrile-water or by heating in trifluoroacetic acid or hydrochloric acid.

A compound of formula XV is synthesized from a compound of formula III and an amine of formula XII following an analogous sequence as described for the synthesis of compounds of formula (I). Alternatively, a compound of formula XV can be prepared by reaction of a compound of formula XVH (prepared from a compound of formula XVP, wherein P represents a suitable protecting group) with a compound of formula IX, X or XI, as described above.

Alternatively, a compound of formula I can be obtained by resolution of a racemic mixture either by chiral preparative HPLC or by crystallization of a diastereomeric salt or co-crystal. The racemic compound can be prepared following the same synthetic sequences described for the preparation of a compound of formula I. In addition, the resolution step can be carried out at a previous stage, using any suitable intermediate.

The compounds of general formula II, IIP, IV, VI, IX, X, XI, XII and XIX wherein $R_1$, $R_2$, $R_3$, $R_{3'}$, LG, V, W, P and P' have the meanings as defined above, are commercially available or can be prepared by conventional methods described in the bibliography.

Scheme 2

The compounds of general formula (I) wherein $R_3$ and $R_{3'}$ taken together form (with the connecting C-atom) a $C_{3-6}$ cycloalkyl group (compounds of formula Ia) or $R_3$ and $R_{3'}$ are equal (compounds of formula Ib) can alternatively be prepared as described in the following scheme:

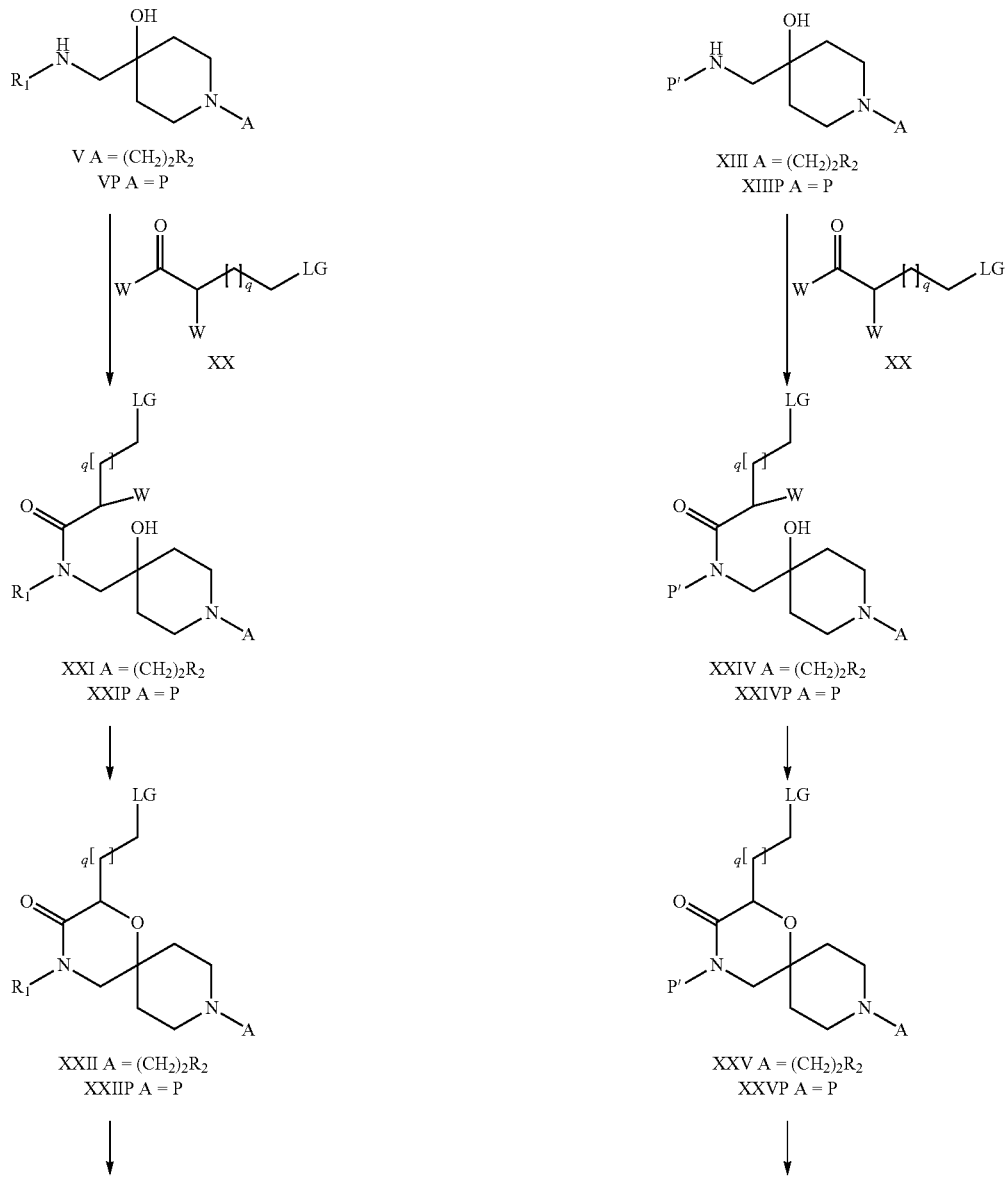

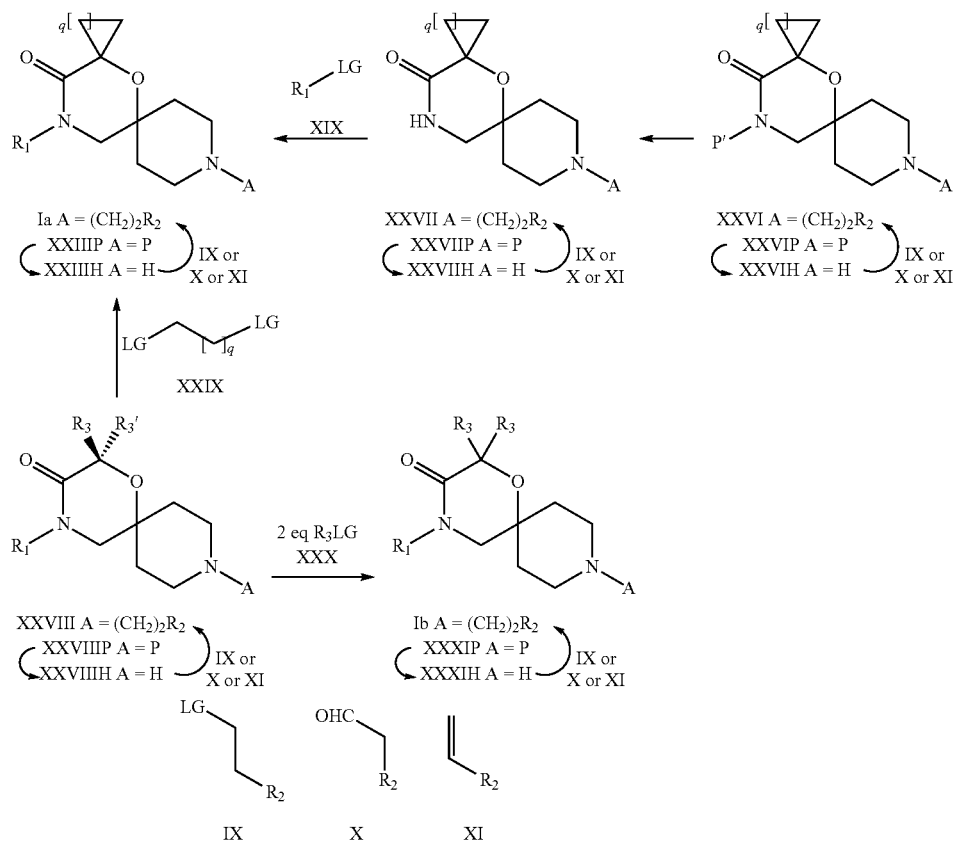

wherein $R_1$, $R_2$ and $R_3$ have the meanings as defined above for a compound of formula (I), q represents 1, 2, 3 or 4, LG represents a leaving group such as halogen, mesylate, tosylate or triflate, W represents another leaving group such as chloro or bromo, P represents a suitable protecting group (preferably Boc) and P' represents another suitable protecting group (preferably 4-methoxybenzyl).

A compound of formula Ia can be prepared from a compound of formula XXII by treatment with a strong base such as lithium diisopropylamide or potassium tert-butoxide, in an aprotic solvent such as tetrahydrofuran, at a suitable temperature, preferably cooling. A compound of formula XXII can be synthesized from a compound of formula V and a compound of formula XX following the reaction conditions described in Scheme 1.

Alternatively, a compound of formula Ia can be prepared from a compound of formula XXVII and a compound of formula XIX following the reaction conditions described in Scheme 1. A compound of formula XXVII can be synthesized from a compound of formula XIII and a compound of formula XX following the reaction conditions described in Scheme 1.

A compound of formula Ib can be prepared from a compound of formula XXVIII by reacting a compound of formula XXVIII with 2 equivalents of an alkylating agent of formula XXX. An analogous double-alkylation process can be used for the alternative preparation of compounds of formula Ia, by reacting a compound of formula XXVIII with an alkylating agent of formula XXIX. The alkylation reactions are carried out in the presence of a strong base such as lithium diisopropylamide or potassium tert-butoxide, in an aprotic solvent such as tetrahydrofuran, at a suitable temperature, preferably comprised between −78° C. and room temperature. Compounds of formula XXVIII can be prepared from compounds of formula V and chloroacetyl chloride (or a suitable analogue) as the acylating agent, following the reaction conditions described in Scheme 1.

In addition, the group $CH_2CH_2R_2$ may be incorporated at different stages of the synthesis to prepare compounds of formula Ia and Ib from suitable precursors and compounds of formula IX, X and XI, following similar reaction conditions as described in Scheme 1 for the preparation of compounds of formula (I)

The compounds of general formula IX, X, XI, XIX, XX, XXIX and XXX wherein $R_1$, $R_2$, $R_3$, q, LG, W, P and P' have the meanings as defined above, are commercially available or can be prepared by conventional methods described in the bibliography.

Moreover, certain compounds of the present invention can also be obtained starting from other compounds of formula I by appropriate conversion reactions of functional groups, in one or several steps, using well-known reactions in organic chemistry under standard experimental conditions. As a way of example, some of these conversions include the demethylation of a methoxy group to yield an hydroxy group, the reduction of a nitro group to yield an amino group, the acylation of an amino group to yield an acylamino group, the conversion of an amino group into an ureido group and the conversion of an ester to an amide.

Examples

All solvents used for synthesis were p. a. quality.
The following abbreviations are used in the examples:
ACN: acetonitrile
Boc: tert-butoxycarbonyl
CAN: cerium ammonium nitrate
DCM: dichloromethane
DEA: diethylamine
DMF: dimethylformamide
DMSO: dimethylsulfoxide
EtOH: ethanol
EX: example
h: hour/s
HPLC: high performance liquid chromatography
INT: intermediate
IPA: isopropanol
LDA: lithium diisopropylamide
MeOH: methanol
MS: mass spectrometry
Min.: minutes
Quant: quantitative
Ret.: retention
r.t.: room temperature
Sat: saturated
s.m.: starting material
TFA: trifluoroacetic acid
THF: tetrahydrofuran
Wt: weight The following method was used to determine the HPLC-MS spectrums:
Column: Xbridge $C_{18}$ XP 30×4.6 mm, 2.5 km;
Temperature: 40° C.;
Flow: 2.0 mL/min;
Gradient: $NH_4HCO_3$ pH 8: ACN (95:5) - - - 0.5 min - - - (95:5) - - - 6.5 min - - - (0:100) - - - 1 min - - - (0:100);
Sample dissolved aprox. 1 mg/mL in $NH_4HCO_3$ pH 8/ACN Alternatively, method B was used in some cases:
Method B:
Column: Gemini-NX 30×4.6 mm, 3 um
Temperature: 40° C.
Flow: 2.0 mL/min
Gradient: $NH_4HCO_3$ pH 8: ACN (95:5) - - - 0.5 min - - - (95:5) - - - 6.5 min - - - (0:100) - - - 1 min - - - (0:100)
Sample dissolved aprox. 1 mg/mL in $NH_4HCO_3$ pH 8/ACN

Synthesis of Intermediates

Intermediate 1A: tert-butyl 1-oxa-6-azaspiro[2.5]octane-6-carboxylate

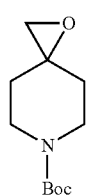 [SMILES: CC(C)(C)OC(=O)N1CCC2(CC1)CO2]

To a suspension of trimethylsulfoxonium iodide (24.3 g, 110 mmol) and NaH (4.4 g, 60 wt % in mineral oil, 110 mmol) in DMSO (140 mL), a solution of tert-butyl 4-oxopiperidine-1-carboxylate (20.0 g, 100 mmol) in DMSO (140 mL) was added dropwise. The reaction mixture was stirred at r.t. for 30 min, then heated at 50° C. for 1 h. After cooling to r.t., ice was slowly added, and the reaction mixture was extracted three times with ethyl acetate. The organic phases were combined, washed with water, dried over $MgSO_4$ and concentrated under vacuum to give the title compound (17.6 g, 82% yield) as a white solid. HPLC retention time: 3.31 min; MS: 158 (M+H−56).

This method was used for the preparation of intermediate 1B using suitable starting materials:

| INT | Structure | Chemical Name | Ret time (min) | MS (M + H) |
|---|---|---|---|---|
| 1B | 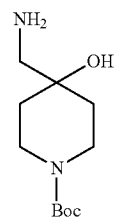 | 6-phenethyl-1-oxa-6-azaspiro[2.5]octane | 3.36 | 218 |

Intermediate 2A: tert-butyl 4-(aminomethyl)-4-hydroxypiperidine-1-carboxylate

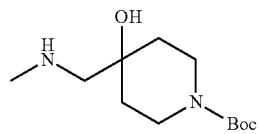 [SMILES: CNCC1(O)CCN(C(=O)OC(C)(C)C)CC1]

A mixture of intermediate 1A (10.0 g, 46.9 mmol) and ammonia solution (201 mL, 7 M solution in methanol, 1.4 mol) was stirred at r.t. overnight. The solvent was removed under vacuum and the residue was purified by flash chromatography, silica gel, gradient dichloromethane to methanol:dichloromethane (1:4) to give the title compound (7.4 g, 69% yield) as a white solid. HPLC retention time: 2.15 min; MS: 131 (M+H−100).

Intermediate 2B: tert-butyl 4-hydroxy-4-((methylamino)methyl)piperidine-1-carboxylate To a solution of intermediate 1A (0.50 g, 2.34 mmol) in a mixture of ethanol-water 5.5:1 (14 mL), methylamine (4.1 mL, 40% solution in water, 47 mmol) was added. The reaction mixture was stirred at r.t. overnight in a sealed tube. The solvent was removed under vacuum to give the title compound (0.534 g, 93% yield) as a white solid. HPLC retention time: 2.28 min; MS: 189 (M+H−56).

This method was used for the preparation of intermediates 2C-2G using suitable starting materials:

| INT | Structure | Chemical name | s.m. | Ret time (min) | MS (M + H) |
|---|---|---|---|---|---|
| 2C | 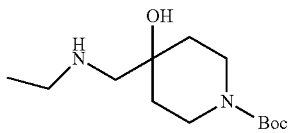 [SMILES: CCNCC1(O)CCN(C(=O)OC(C)(C)C)CC1] | tert-butyl 4-((ethylamino)methyl)-4-hydroxypiperidine-1-carboxylate | 1A | 2.35 | 259 |
| 2D | 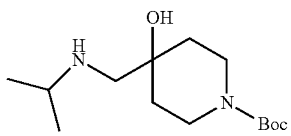 [SMILES: CC(C)NCC1(O)CCN(C(=O)OC(C)(C)C)CC1] | tert-butyl 4-hydroxy-4-((isopropylamino)methyl)piperidine-1-carboxylate | 1A | 2.61 | 273 |
| 2E | 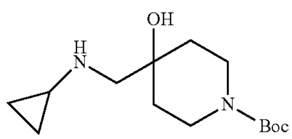 [SMILES: CC(C)(C)OC(=O)N1CCC(O)(CNC2CC2)CC1] | tert-butyl 4-((cyclopropylamino)methyl)-4-hydroxypiperidine-1-carboxylate | 1A | 3.28 | 271 |
| 2F | 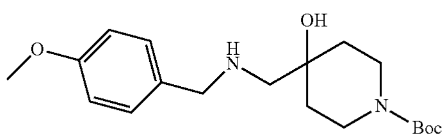 [SMILES: COc1ccc(CNCC2(O)CCN(C(=O)OC(C)(C)C)CC2)cc1] | tert-butyl 4-hydroxy-4-(((4-methoxybenzyl)amino)methyl)piperidine-1-carboxylate | 1A | 3.80 | 351 |
| 2G | 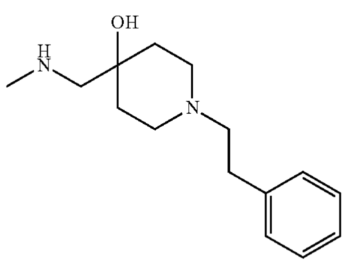 [SMILES: CNCC1(O)CCN(CCc2ccccc2)CC1] | 4-((methylamino)methyl)-1-phenethylpiperidin-4-ol | 1B | 2.26 | 249 |

Intermediate 3A: tert-butyl 2-(2-chloroethyl)-4-isopropyl-3-oxo-1-oxa-4,9-diazaspiro[5.5]undecane-9-carboxylate

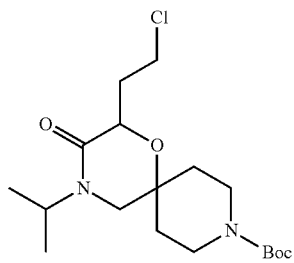 [SMILES: CC(C)N1CC2(CCN(C(=O)OC(C)(C)C)CC2)OC(CCCl)C1=O]

Step 1. tert-butyl 4-((2-bromo-4-chloro-N-isopropylbutanamido)methyl)-4-hydroxypiperidine-1-carboxylate: To a solution of intermediate 2D (0.500 g, 1.84 mmol) and triethylamine (0.613 mL, 4.41 mmol) in dichloromethane (95 mL), a solution of 2-bromo-4-chlorobutanoyl chloride (prepared as described in U.S. Pat. No. 6,114,541A1(2000) Ex1) (0.605 g, 2.75 mmol) in dichloromethane (95 mL) was added dropwise at 0° C. The reaction mixture was stirred at r.t. for 4 h, NaHCO₃ sat solution was added and the aqueous phase was extracted with dichloromethane. The organic phases were combined, dried over MgSO₄, filtered and concentrated to dryness. The residue was purified by flash chromatography, silica gel, gradient dichloromethane to methanol:dichloromethane (1:4) to give the title compound (0.243 g, 29%). HPLC retention time: 4.75 min; MS: 357 (M+H−100).

Step 2. Title compound: To a solution of the crude product obtained in step 1 in THF (5 mL), potassium tert-butoxide solution (1.05 mL, 1M in THF, 1.05 mmol) was added dropwise. The reaction mixture was stirred at r.t. overnight. Water was then added, the phases were separated and the aqueous phase was extracted with ethyl acetate. The organic phases were combined, dried over MgSO₄, filtered and concentrated under vacuum. The residue was purified by flash chromatography, silica gel, gradient dichloromethane to methanol:dichloromethane (1:4) to give the title compound (89 mg, 45% yield). HPLC retention time: 4.48 min; MS: 375 (M+H).

This method was used for the preparation of intermediate 3B using suitable starting materials:

| INT | Structure | Chemical name | s.m. | Ret time (min) | MS (M + H) |
|---|---|---|---|---|---|
| 3B | 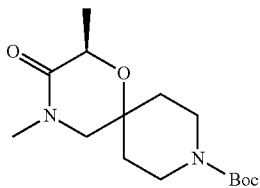 [SMILES: C[C@H]1OC2(CCN(C(=O)OC(C)(C)C)CC2)CN(C)C1=O] | tert-butyl 2-(2-chloroethyl)-4-ethyl-3-oxo-1-oxa-4,9-diazaspiro[5.5]undecane-9-carboxylate | 2C | 4.27 | 361 |

Intermediate 3C: (R)-tert-butyl 2,4-dimethyl-3-oxo-1-oxa-4,9-diazaspiro[5.5]undecane-9-carboxylate Step 1. (S)-tert-butyl 4-((2-chloro-N-methylpropanamido)methyl)-4-hydroxypiperidine-1-carboxylate: To a solution of intermediate 2B (0.521 g, 2.13 mmol) in ethyl acetate (10 mL), a solution of $K_2CO_3$ (0.825 g, 5.97 mmol) in water (7 mL) was added. After cooling to 0° C., a solution of (S)-2-chloropropanoyl chloride (0.368 g, 2.90 mmol) in ethyl acetate (2 mL) was added dropwise. The reaction mixture was stirred at 0° C. for 30 min, the layers were separated and the aqueous phase was extracted with ethyl acetate. The organic phases were combined, washed with 0.5 M HCl aqueous solution and then $NaHCO_3$ sat solution, dried over $MgSO_4$, filtered and concentrated to dryness to give the title compound (0.594 g). HPLC retention time: 3.48 min; MS: 235 (M+H−100).

Step 2. Title compound: A solution of the crude product obtained in step 1 in THF (30 mL) was cooled to −78° C. using a dry ice/acetone bath. After addition of potassium tert-butoxide solution (1.95 mL, 1M in THF, 1.95 mmol), the reaction mixture was stirred at −78° C. for 30 min. $NH_4Cl$ sat solution was then added, and the aqueous phase was extracted with ethyl acetate. The organic phases were combined, dried over $MgSO_4$, filtered and concentrated under vacuum. The residue was crystallized from hot isopropyl acetate to give the title compound (0.320 g, 60% yield). HPLC retention time: 3.32 min; MS: 299 (M+H). Optical purity: 98.9% ee, determined by chiral HPLC: column: Chiralpak ADH 250×4.6 mm, 5μ; temperature: 25° C.; flow: 0.5 mL/min; eluent: heptane/(ethanol+0.2% DEA) 85:15.

This method was used for the preparation of intermediates 3D-3O using suitable starting materials:

| INT | Structure | Chemical name | s.m. | Ret time (min) | MS (M + H) |
|---|---|---|---|---|---|
| 3D | 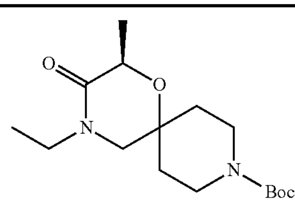 | (R)-tert-butyl 4-ethyl-2-methyl-3-oxo-1-oxa-4,9-diazaspiro[5.5]undecane-9-carboxylate | 2C | 3.67 | 313 |
| 3E | 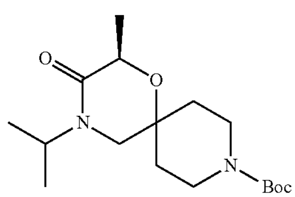 [SMILES: CC(C)N1CC2(CCN(C(=O)OC(C)(C)C)CC2)O[C@H](C)C1=O] | (R)-tert-butyl 4-isopropyl-2-methyl-3-oxo-1-oxa-4,9-diazaspiro[5.5]undecane-9-carboxylate | 2D | 3.94 | 327 |
| 3F | 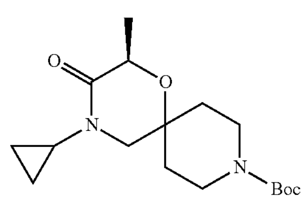 [SMILES: C[C@H]1OC2(CCN(C(=O)OC(C)(C)C)CC2)CN(C2CC2)C1=O] | (R)-tert-butyl 4-cyclopropyl-2-methyl-3-oxo-1-oxa-4,9-diazaspiro[5.5]undecane-9-carboxylate | 2E | 3.74 | 325 |

-continued

| INT | Structure | Chemical name | s.m. | Ret time (min) | MS (M + H) |
|---|---|---|---|---|---|
| 3G | 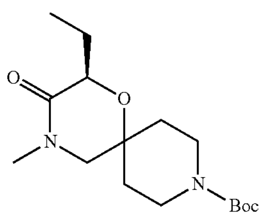 [SMILES: CC[C@H]1OC2(CCN(C(=O)OC(C)(C)C)CC2)CN(C)C1=O] | (R)-tert-butyl 2-ethyl-4-methyl-3-oxo-1-oxa-4,9-diazaspiro[5.5]undecane-9-carboxylate | 2B | 3.82 | 313 |
| 3H | 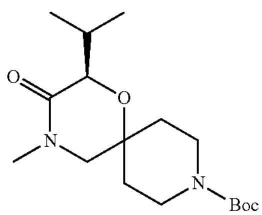 [SMILES: CC(C)[C@H]1OC2(CCN(C(=O)OC(C)(C)C)CC2)CN(C)C1=O] | (R)-tert-butyl 2-isopropyl-4-methyl-3-oxo-1-oxa-4,9-diazaspiro[5.5]undecane-9-carboxylate | 2B | 4.28 | 327 |
| 3I | 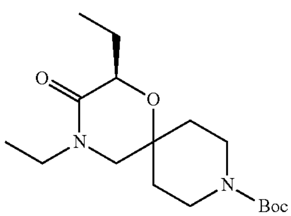 [SMILES: CC[C@H]1OC2(CCN(C(=O)OC(C)(C)C)CC2)CN(CC)C1=O] | (R)-tert-butyl 2,4-diethyl-3-oxo-1-oxa-4,9-diazaspiro[5.5]undecane-9-carboxylate | 2C | 3.96 | 327.2 |
| 3J | 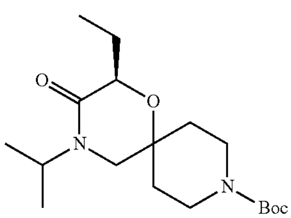 [SMILES: CC[C@H]1OC2(CCN(C(=O)OC(C)(C)C)CC2)CN(C(C)C)C1=O] | (R)-tert-butyl 2-ethyl-4-isopropyl-3-oxo-1-oxa-4,9-diazaspiro[5.5]undecane-9-carboxylate | 2D | 4.24 | 341.2 |
| 3K | 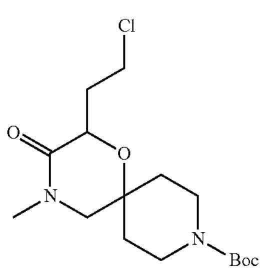 [SMILES: CN1CC2(CCN(C(=O)OC(C)(C)C)CC2)OC(CCCl)C1=O] | tert-butyl 2-(2-chloroethyl)-4-methyl-3-oxo-1-oxa-4,9-diazaspiro[5.5]undecane-9-carboxylate | 2B | 3.9 | 347.1 |
| 3L | 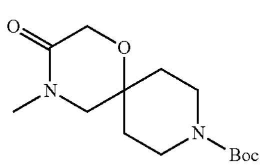 [SMILES: CN1CC2(CCN(C(=O)OC(C)(C)C)CC2)OCC1=O] | tert-butyl 4-methyl-3-oxo-1-oxa-4,9-diazaspiro[5.5]undecane-9-carboxylate (1*) | 2B | 2.95 | 285.1 |
| 3M | 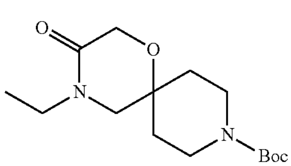 [SMILES: CCN1CC2(CCN(C(=O)OC(C)(C)C)CC2)OCC1=O] | tert-butyl 4-ethyl-3-oxo-1-oxa-4,9-diazaspiro[5.5]undecane-9-carboxylate (1*) | 2C | 3.28 (method B) | 299.1 |

| INT | Structure | Chemical name | s.m. | Ret time (min) | MS (M + H) |
|---|---|---|---|---|---|
| 3N | 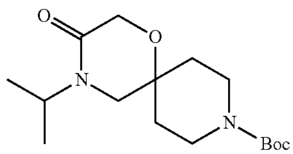 [SMILES: CC(C)N1CC2(CCN(C(=O)OC(C)(C)C)CC2)OCC1=O] | tert-butyl 4-isopropyl-3-oxo-1-oxa-4,9-diazaspiro[5.5]undecane-9-carboxylate (1*) | 2D | 3.51 | 313.2 |
| 3O | 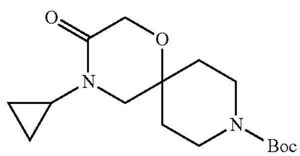 [SMILES: CC(C)(C)OC(=O)N1CCC2(CC1)CN(C1CC1)C(=O)CO2] | tert-butyl 4-cyclopropyl-3-oxo-1-oxa-4,9-diazaspiro[5.5]undecane-9-carboxylate (1*) | 2E | 3.35 (method B) | 311.1 |

(1*) In Step 2, after 15 min at –78° C., the reaction mixture was stirred at –30° C. for 2 h and then it was quenched and worked-up as usual.

Intermediate 4A: tert-butyl 12-ethyl-13-oxo-4-oxa-8,12-diazadispiro[2.1.5.3]tridecane-8-carboxylate Intermediate 4C: tert-butyl 12-(4-methoxybenzyl)-13-oxo-4-oxa-8,12-diazadispiro[2.1.5.3]tridecane-8-carboxylate

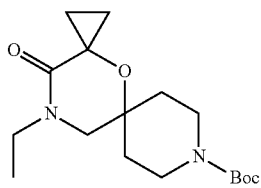

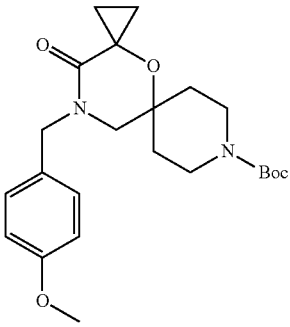 [SMILES: COc1ccc(CN2CC3(CCN(C(=O)OC(C)(C)C)CC3)OC3(CC3)C2=O)cc1]

A solution of intermediate 3B (2.77 g, 7.68 mmol) in THF (75 mL) was cooled to 0° C. After addition of LDA solution (11.5 mL, 2M in THF/n-heptane/ethylbenzene, 23.0 mmol), the reaction mixture was stirred at 0° C. for 3 h. NH$_4$Cl sat solution was then added, and the aqueous phase was extracted with dichloromethane. The organic phase was dried over MgSO$_4$, filtered and concentrated under vacuum. The residue was purified by flash chromatography, silica gel, gradient dichloromethane to methanol:dichloromethane (1:4) to give the title compound (1.53 g, 61% yield). HPLC retention time: 3.85 min; MS: 325 (M+H).

This method was used for the preparation of intermediate 4B using suitable starting materials:

Step 1. tert-butyl 4-((2-bromo-4-chloro-N-(4-methoxybenzyl)butanamido)methyl)-4-hydroxypiperidine-1-carboxylate: To a solution of intermediate 2F (9.94 g, 28.4 mmol) and triethylamine (9.5 mL, 68.1 mmol) in dichloromethane (500 mL), a solution of 2-bromo-4-chlorobutanoyl chloride (prepared as described in U.S. Pat. No. 6,114,541 A1 (2000) Ex1) (9.35 g, 20.2 mmol) in dichloromethane (200 mL) was added dropwise at 0° C. The reaction mixture was stirred at 0° C. for 3 h. Dichloromethane and NaHCO$_3$ aqueous sat. solution were added and the phases were separated. The aqueous phase was extracted with dichloromethane and the organic phases were combined, dried over MgSO$_4$, filtered and concentrated to dry-

| INT | Structure | Chemical name | s.m. | Ret time (min) | MS (M + H) |
|---|---|---|---|---|---|
| 4B | 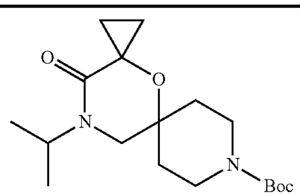 | tert-butyl 12-isopropyl-13-oxo-4-oxa-8,12-diazadispiro[2.1.5.3]tridecane-8-carboxylate | 3A | 4.08 | 339 |

Intermediate 4B has alternatively been obtained by the alkylation method described for the preparation of Intermediate 4F (using 2-bromopropane instead of iodomethane as the alkylating agent).

ness, to give the title compound (17.6 g, crude product). HPLC retention time: 4.82 min; MS: 435 (M+H−100).

Step 2. Title compound: A solution of the crude product obtained in step 1 (14.8 g, 27.7 mmol) in THF (185 mL) was cooled under nitrogen to 0° C. After addition of potassium tert-butoxide solution (111 mL, 1M in THF, 111 mmol), the reaction mixture was stirred at 0° C. for 2 h. NH₄Cl sat solution was then added, and the aqueous phase was extracted with ethyl acetate. The organic phases were combined, dried over MgSO₄, filtered and concentrated under vacuum. The residue was purified by flash chromatography, silica gel, gradient dichloromethane to methanol:dichloromethane (1:4) to give the title compound (5.51 g, 48% yield for the 2 steps). HPLC retention time: 4.46 min; MS: 417 (M+H).

Intermediate 4D: 8-phenethyl-4-oxa-8,12-diazadispiro[2.1.5.3]tridecan-13-one

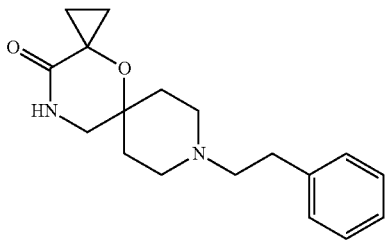 [SMILES: O=C1NCC2(CCN(CCc3ccccc3)CC2)OC12CC2]

Step 1. 12-(4-methoxybenzyl)-4-oxa-8,12-diazadispiro[2.1.5.3]tridecan-13-one trifluoroacetate. To a solution of intermediate 4C (1.50 g, 3.6 mmol) in dichloromethane (36 mL), trifluoroacetic acid (2.8 mL, 36.0 mmol) was added, and the reaction mixture was stirred at r.t. for 4 h. The solvent was evaporated to dryness to give the title compound as a crude product (2.30 g, 67 wt %, quant yield), that was used in the following step without further purification. HPLC retention time: 2.43 min; MS: 317 (M+H).

Step 2. 12-(4-methoxybenzyl)-8-phenethyl-4-oxa-8,12-diazadispiro[2.1.5.3]tridecan-13-one. A mixture of the crude product obtained in step 1 (2.30 g, 67 wt %, 3.6 mmol), (2-bromoethyl)benzene (0.802 g, 4.3 mmol) and K₂CO₃ (2.49 g, 18.1 mmol) in acetonitrile (36 mL) was heated at 80° C. in a sealed tube overnight. Water was added, and the reaction mixture was extracted with ethyl acetate. The organic phases were combined, dried over MgSO₄, filtered and concentrated to dryness. The residue was purified by flash chromatography, silica gel, gradient dichloromethane to methanol:dichloromethane (1:4) to give the title compound (1.17 g, 77% yield). HPLC retention time: 4.55 min; MS: 421 (M+H).

Step 3. Title compound: A mixture of the crude product obtained in step 2 (0.170 g, 0.404 mmol) and CAN (0.568 g, 1.21 mmol), acetonitrile (2.5 mL) and water (2.5 mL) was stirred at r.t. for 7 h. Na₂CO₃ sat solution was added to the reaction mixture and it was extracted with ethyl acetate. The organic phases were combined, washed with brine, dried over MgSO₄, filtered and concentrated to dryness. The residue was purified by eluting through an acidic ion exchange resin cartridge (SCX), to give the title compound (106 mg, 88% yield). HPLC retention time: 3.31 min; MS: 301 (M+H).

Intermediate 4E: tert-butyl 13-oxo-4-oxa-8,12-diazadispiro[2.1.5.3]tridecane-8-carboxylate

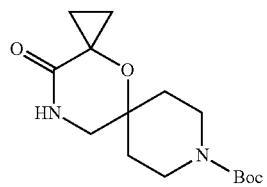 [SMILES: CC(C)(C)OC(=O)N1CCC2(CC1)CNC(=O)C1(CC1)O2]

Step 1. 4-oxa-8,12-diazadispiro[2.1.5.3]tridecan-13-one trifluoroacetate: A solution of intermediate 4C (1.78 g, 4.26 mmol) in TFA (20 mL) was stirred in a sealed tube at 80° C. for 4 days. The reaction mixture was concentrated to dryness and water was added to the residue. The acidic aqueous phase was washed with ethyl ether, which was discarded. The aqueous layer was evaporated to dryness to give the title compound (1.17 g). HPLC retention time: 0.33 min; MS: 197 (M+H).

Step 2. Title compound: A mixture of the crude product obtained in step 1, di-tert-butyl dicarbonate (1.40 g, 6.40 mmol), 1,4-dioxane (40 mL) and 1M NaOH aqueous solution (10 mL) was stirred at r.t. overnight. Water was added and the resulting mixture was extracted with ethyl acetate. The organic phases were combined, dried over MgSO₄, filtered and concentrated to dryness. The residue was purified by flash chromatography, silica gel, gradient dichloromethane to methanol:dichloromethane (1:4) to give the title compound (0.872 g, 69% yield for the 2 steps). HPLC retention time: 3.29 min; MS: 297 (M+H).

Intermediate 4F: tert-butyl 12-methyl-13-oxo-4-oxa-8,12-diazadispiro[2.1.5.3]tridecane-8-carboxylate

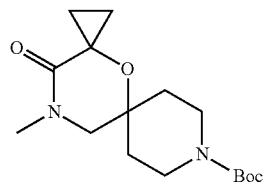 [SMILES: CN1CC2(CCN(C(=O)OC(C)(C)C)CC2)OC2(CC2)C1=O]

To a solution of intermediate 4E (0.190 g, 0.641 mmol) in dry DMF (5 mL), NaH (51 mg, 60 wt % in mineral oil, 1.28 mmol) was added at r.t. The reaction mixture was stirred at r.t. for 30 min, then iodomethane (0.040 mL, 0.641 mmol) was added and the resulting mixture was stirred at r.t. overnight. Water was added to the reaction mixture and it was extracted with ethyl acetate. The organic phases were combined, dried over MgSO₄, filtered and concentrated to dryness. The residue was purified by flash chromatography, silica gel, gradient dichloromethane to methanol:dichloromethane (1:4) to give the title compound (166 mg, 83% yield). HPLC retention time: 3.57 min; MS: 311 (M+H).

Intermediate 5A: tert-butyl 2,2-diethyl-4-methyl-3-oxo-1-oxa-4,9-diazaspiro[5.5]undecane-9-carboxylate

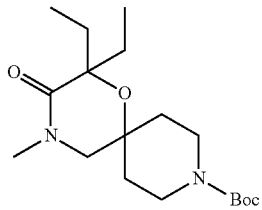 [SMILES: CCC1(CC)OC2(CCN(C(=O)OC(C)(C)C)CC2)CN(C)C1=O]

A solution of intermediate 3L (0.200 g, 0.70 mmol) in dry THF (1 mL) was cooled to 0° C. After slow addition of LDA solution (1.41 mL, 2M in THF/n-heptane/ethylbenzene, 2.81 mmol), the reaction mixture was stirred at 0° C. for 30 min. Iodoethane (0.28 mL, 3.52 mmol) was then added and the reaction mixture was stirred at 0-5° C. for further 90 min. NH$_4$Cl sat solution was then added, and the aqueous phase was extracted three times with ethyl acetate. The combined organic phases were dried over Na$_2$SO$_4$, filtered and concentrated under vacuum. The residue was purified by flash chromatography, silica gel, gradient dichloromethane to methanol:dichloromethane (1:4) to give the title compound (186 mg, 78% yield). HPLC retention time: 4.29 min; MS: 341 (M+H).

This method was used for the preparation of intermediates 5B-5D using suitable starting materials:

Intermediate 5E: tert-butyl 4-methyl-3-oxo-2-(prop-2-yn-1-yl)-1-oxa-4,9-diazaspiro[5.5]undecane-9-carboxylate

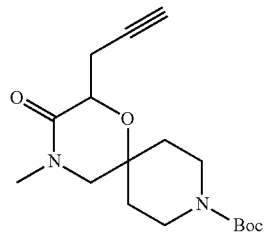

A solution of intermediate 3L (0.500 g, 1.76 mmol) in dry THF (2.5 mL) was cooled to 0° C. After slow addition of LDA solution (1.05 mL, 2M in THF/n-heptane/ethylbenzene, 2.11 mmol), the reaction mixture was stirred at 0° C. for 30 min. Propargyl bromide solution (0.24 mL, 80% wt in toluene, 2.11 mmol) was then added and the reaction mixture was stirred at 0-5° C. for further 2 h. NH$_4$Cl sat solution was added and the aqueous phase was extracted three times with dichloromethane. The combined organic phases were dried over MgSO$_4$, filtered and concentrated under vacuum. The residue was purified by flash chromatography, silica gel, gradient dichloromethane to methanol:dichloromethane (1:4) to give the title compound (327 mg, 58% yield). HPLC retention time: 3.45 min; MS: 323 (M+H).

| INT | Structure | Chemical name | s.m. | Ret time (min) | MS (M + H) |
|---|---|---|---|---|---|
| 5B | 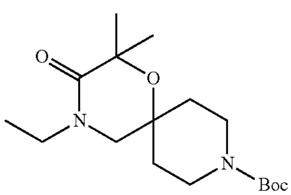 [SMILES: CCN1CC2(CCN(C(=O)OC(C)(C)C)CC2)OC(C)(C)C1=O] | tert-butyl 4-ethyl-2,2-dimethyl-3-oxo-1-oxa-4,9-diazaspiro[5.5]undecane-9-carboxylate | 3M | 3.93 (method B) | 327.2 |
| 5C | 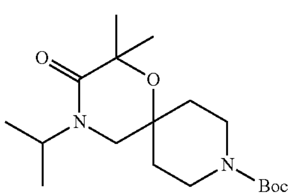 | tert-butyl 4-isopropyl-2,2-dimethyl-3-oxo-1-oxa-4,9-diazaspiro[5.5]undecane-9-carboxylate | 3N | 4.22 (method B) | 341.2 |
| 5D | 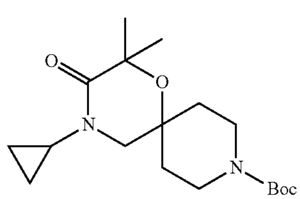 [SMILES: CC(C)(C)OC(=O)N1CCC2(CC1)CN(C1CC1)C(=O)C(C)(C)O2] | tert-butyl 4-cyclopropyl-2,2-dimethyl-3-oxo-1-oxa-4,9-diazaspiro[5.5]undecane-9-carboxylate | 3O | 4.01 (method B) | 339.2 |

Intermediate 5F: tert-butyl 14-methyl-15-oxo-6-oxa-10,14-diazadispiro[4.1.5.3]pentadecane-10-carboxylate

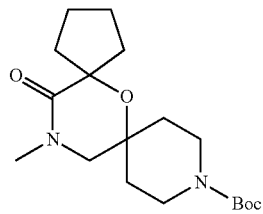 [SMILES: CN1CC2(CCN(C(=O)OC(C)(C)C)CC2)OC2(CCCC2)C1=O]

Step 1. tert-butyl 2-(4-bromobutyl)-4-methyl-3-oxo-1-oxa-4,9-diazaspiro[5.5]undecane-9-carboxylate: A solution of intermediate 3L (0.400 g, 1.41 mmol) in dry THF (20 mL) was cooled to −50° C. After slow addition of LDA solution (2.11 mL, 2M in THF/n-heptane/ethylbenzene, 4.22 mmol), the reaction mixture was stirred at −50° C. for 30 min. 1,4-Dibromobutane (0.25 mL, 2.11 mmol) was then added and the reaction mixture was stirred at −50° C. for further 90 min and then it was allowed to reach room temperature and stirred for an additional hour. NH₄Cl sat solution was added and the aqueous phase was extracted three times with ethyl acetate. The combined organic phases were dried over MgSO₄, filtered and concentrated under vacuum to give the title compound as a crude product, that was used as such without further purification. HPLC retention time: 4.39 min; MS: 421 (M+H).

Step 2. Title compound: A solution of the product obtained in Step 1 (1.41 mmol) in dry THF (30 mL) was cooled to −50° C. After slow addition of LDA solution (2.11 mL, 2M in THF/n-heptane/ethylbenzene, 4.22 mmol), the reaction mixture was stirred at 0° C. for 1 h and then it was further stirred at room temperature for 1 h. NH₄Cl sat solution was added and the aqueous phase was extracted with ethyl acetate. The organic phase was dried over MgSO₄, filtered and concentrated under vacuum. The residue was purified by flash chromatography, silica gel, gradient dichloromethane to methanol:dichloromethane (1:4) to give the title compound (199 mg, 42% yield for the two steps). HPLC retention time: 4.09 min; MS: 339 (M+H).

Intermediate 6: tert-butyl 2-(2-hydroxyethyl)-4-methyl-3-oxo-1-oxa-4,9-diazaspiro[5.5]undecane-9-carboxylate

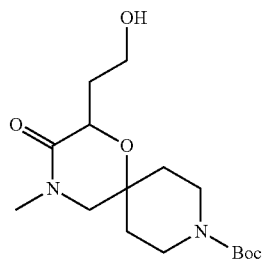 [SMILES: CN1CC2(CCN(C(=O)OC(C)(C)C)CC2)OC(CCO)C1=O]

A solution of intermediate 3K (0.200 g, 0.58 mmol) in THF (1 mL) and 1M NaOH solution (1 mL) was heated to reflux in a sealed tube overnight. It was then concentrated to dryness and water and ethyl acetate were added to the residue. The phases were separated and the aqueous phase was extracted three times with ethyl acetate. The combined organic phases were dried over MgSO₄, filtered and concentrated under vacuum to give the title compound (66 mg, 35% yield). HPLC retention time: 2.96 min; MS: 329 (M+H).

Synthesis of Examples

Example 1: 12-ethyl-8-{2-[3-(trifluoromethyl)pyridin-2-yl]ethyl}-4-oxa-8,12-diazadispiro[2.1.5.3]tridecan-13-one hydrochloride

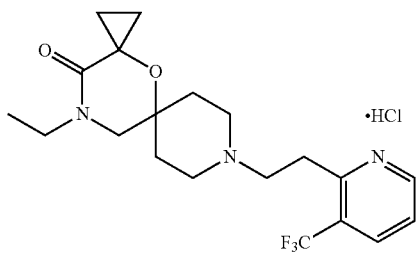 [SMILES: CCN1CC2(CCN(CCc3ncccc3C(F)(F)F)CC2)OC2(CC2)C1=O ; Cl]

Step 1. 12-ethyl-4-oxa-8,12-diazadispiro[2.1.5.3]tridecan-13-one trifluoroacetate. To a solution of intermediate 4A (1.50 g, 4.65 mmol) in dichloromethane (46 mL), trifluoroacetic acid (3.6 mL, 46.5 mmol) was added, and the reaction mixture was stirred at r.t. for 3 h. The solvent was evaporated to dryness to give the title compound as a crude product (3.02 g, 52 wt %, quant yield), that was used in the following step without further purification. HPLC retention time: 0.83 min; MS: 225 (M+H).

Step 2. 12-ethyl-4-oxa-8,12-diazadispiro[2.1.5.3]tridecan-13-one. The crude product obtained in step 1 (208 mg, 52 wt %, 0.331 mmol) was dissolved in dichloromethane and washed twice with 1M NaOH aqueous solution. The combined aqueous phases were extracted with dichloromethane and the organic phases were combined, washed with water, dried over MgSO₄, filtered and concentrated under vacuum to give the title compound as a crude product (0.056 g, 78%). HPLC retention time: 0.75 min; MS: 225 (M+H).

Step 3. 12-ethyl-8-{2-[3-(trifluoromethyl)pyridin-2-yl]ethyl}-4-oxa-8,12-diazadispiro [2.1.5.3]tridecan-13-one: A solution of the crude product obtained in step 2 (0.056 g, 0.249 mmol) and 3-trifluoromethyl-2-vinylpyridine (prepared similarly as described in *Angew. Chem. Int. Ed.*, 2013, 52, 9755) (0.068 g, 0.393 mmol) in 2-methoxyethanol (0.6 mL) was heated at 120° C. in a sealed tube under argon for 1 day. The reaction mixture was allowed to cool to r.t. and the solvent was evaporated. The residue was purified by flash chromatography, silica gel, gradient dichloromethane to methanol:dichloromethane (1:4) to give the title compound as its free base (45 mg, 45% yield). HPLC retention time: 3.49 min; MS: 398.0 (M+H).

Step 4. Title compound: To a solution of the free base obtained in Step 3 (45 mg, 0.113 mmol) in anhydrous diethyl ether (2 mL), HCl (2M solution in diethyl ether, 0.056 mL, 0.113 mmol) was added, and the mixture was stirred at r.t. for 1 h. The solvent was evaporated under vacuum to give the corresponding HCl salt (45 mg, 92% yield). HPLC retention time: 3.62 min; MS: 398.0 (M+H).

This method was used for the preparation of examples 2-6 using suitable starting materials:

| EX | Structure | Chemical name | Ret time (min) | MS (M + H) |
|---|---|---|---|---|
| 2 | 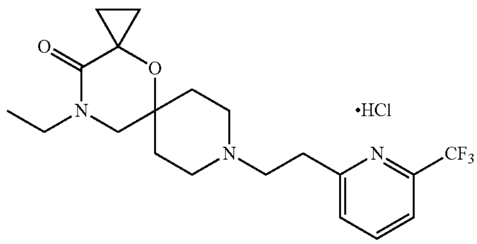 [SMILES: CCN1CC2(CCN(CCc3cccc(C(F)(F)F)n3)CC2)OC2(CC2)C1=O ; Cl] | 12-ethyl-8-{2-[6-(trifluoromethyl)pyridin-2-yl]ethyl}-4-oxa-8,12-diazadispiro[2.1.5.3]tridecan-13-one hydrochloride | 3.76 | 398.0 |
| 3 | 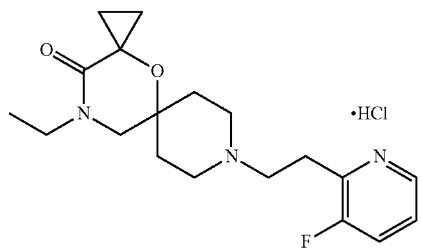 [SMILES: CCN1CC2(CCN(CCc3ncccc3F)CC2)OC2(CC2)C1=O ; Cl] | 12-ethyl-8-[2-(3-fluoropyridin-2-yl)ethyl]-4-oxa-8,12-diazadispiro[2.1.5.3]tridecan-13-one hydrochloride | 3.05 | 348.1 |
| 4 | 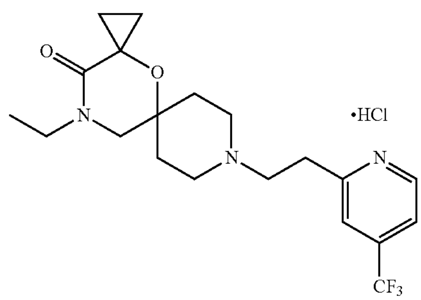 [SMILES: CCN1CC2(CCN(CCc3cc(C(F)(F)F)ccn3)CC2)OC2(CC2)C1=O ; Cl] | 12-ethyl-8-{2-[4-(trifluoromethyl)pyridin-2-yl]ethyl}-4-oxa-8,12-diazadispiro[2.1.5.3]tridecan-13-one hydrochloride | 3.65 | 398.2 |
| 5 | 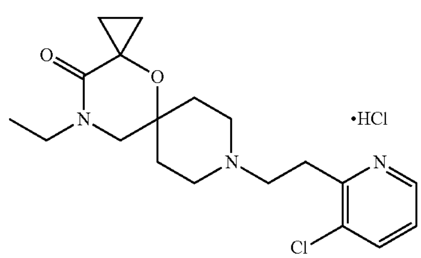 [SMILES: CCN1CC2(CCN(CCc3ncccc3Cl)CC2)OC2(CC2)C1=O ; Cl] | 8-[2-(3-chloropyridin-2-yl)ethyl]-12-ethyl-4-oxa-8,12-diazadispiro[2.1.5.3]tridecan-13-one hydrochloride | 3.29 | 364.1 |
| 6 | 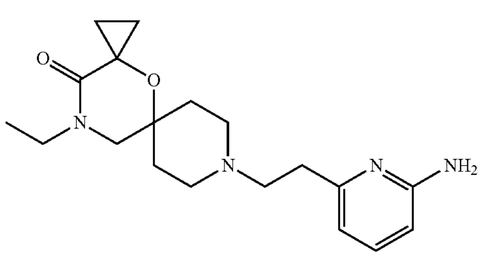 [SMILES: CCN1CC2(CCN(CCc3cccc(N)n3)CC2)OC2(CC2)C1=O] | 8-[2-(6-aminopyridin-2-yl)ethyl]-12-ethyl-4-oxa-8,12-diazadispiro[2.1.5.3]tridecan-13-one | 2.73 | 345.2 |

Where indicated, the hydrochloride salts were prepared as described in example 1

Example 7: 12-ethyl-8-phenethyl-4-oxa-8,12-diaz-adispiro[2.1.5.3]tridecan-13-one hydrochloride

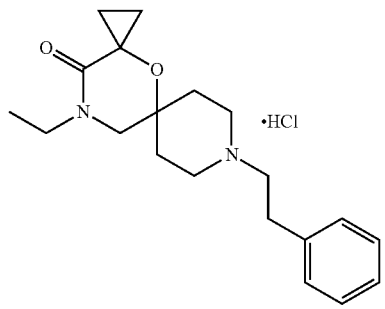 [SMILES: CCN1CC2(CCN(CCc3ccccc3)CC2)OC2(CC2)C1=O ; Cl]

A mixture of the crude product obtained in step 1 of example 1 (0.044 g, 0.129 mmol), (2-bromoethyl)benzene (0.021 mL, 0.155 mmol), sodium iodide (0.012 g, 0.078 mmol) and $K_2CO_3$ (0.143 g, 1.04 mmol) in acetonitrile (2 mL) was heated at 80° C. in a sealed tube overnight. Water was added, and the reaction mixture was extracted with ethyl acetate. The organic phases were combined, washed with brine, dried over $MgSO_4$, filtered and concentrated to dryness. The residue was purified by flash chromatography, silica gel, gradient dichloromethane to methanol:dichloromethane (1:4) to give the title compound as its free base (12 mg, 28% yield).

The previous compound was converted to its hydrochloride salt as described in example 1. HPLC retention time: 3.74 min; MS: 329.1 (M+H).

This method was used for the preparation of examples 8-53 using suitable starting materials:

| EX | Structure | Chemical name | Ret time (min) | MS (M + H) |
|---|---|---|---|---|
| 8 | 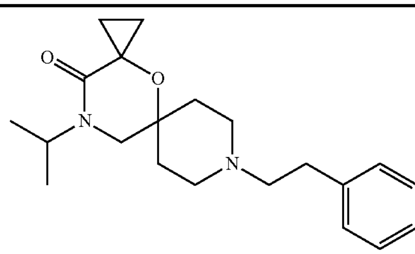 | 12-isopropyl-8-phenethyl-4-oxa-8,12-diazadispiro[2.1.5.3]tridecan-13-one | 4.10 | 343.2 |
| 9 | 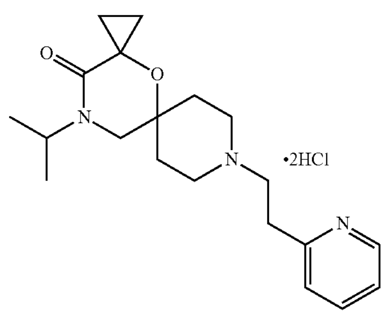 [SMILES: CC(C)N1CC2(CCN(CCc3ccccn3)CC2)OC2(CC2)C1=O] | 12-isopropyl-8-[2-(pyridin-2-yl)ethyl]-4-oxa-8,12-diazadispiro[2.1.5.3]tridecan-13-one dihydrochloride | 3.00 | 344.2 |
| 10 | 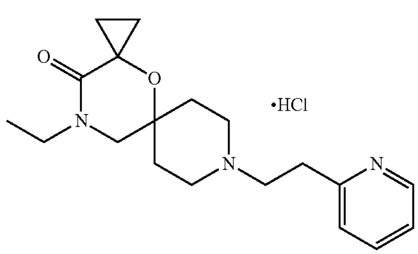 [SMILES: CCN1CC2(CCN(CCc3ccccn3)CC2)OC2(CC2)C1=O ; Cl] | 12-ethyl-8-[2-(pyridin-2-yl)ethyl]-4-oxa-8,12-diazadispiro[2.1.5.3]tridecan-13-one hydrochloride | 2.76 | 330 |
| 11 | 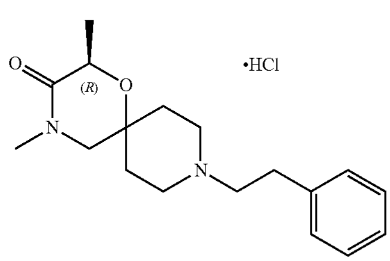 | (R)-2,4-dimethyl-9-phenethyl-1-oxa-4,9-diazaspiro[5.5]undecan-3-one hydrochloride (*1) | 3.35 | 303.2 |

-continued

| EX | Structure | Chemical name | Ret time (min) | MS (M + H) |
|---|---|---|---|---|
| 12 | 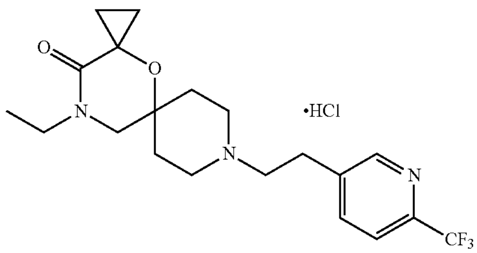 [SMILES: CCN1CC2(CCN(CCc3ccc(C(F)(F)F)nc3)CC2)OC2(CC2)C1=O ; Cl] | 12-ethyl-8-{2-[6-(trifluoromethyl)pyridin-3-yl]ethyl}-4-oxa-8,12-diazadispiro[2.1.5.3]tridecan-13-one hydrochloride | 3.71 | 398 |
| 13 | 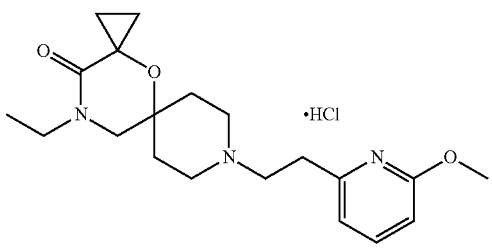 [SMILES: CCN1CC2(CCN(CCc3cccc(OC)n3)CC2)OC2(CC2)C1=O ; Cl] | 12-ethyl-8-[2-(6-methoxypyridin-2-yl)ethyl]-4-oxa-8,12-diazadispiro[2.1.5.3]tridecan-13-one hydrochloride | 3.43 | 360.1 |
| 14 | 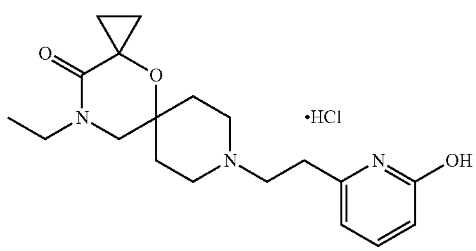 [SMILES: CCN1CC2(CCN(CCc3cccc(O)n3)CC2)OC2(CC2)C1=O ; Cl] | 12-ethyl-8-[2-(6-hydroxypyridin-2-yl)ethyl]-4-oxa-8,12-diazadispiro[2.1.5.3]tridecan-13-one hydrochloride (4*) | 2.54 | 346 |
| 15 | 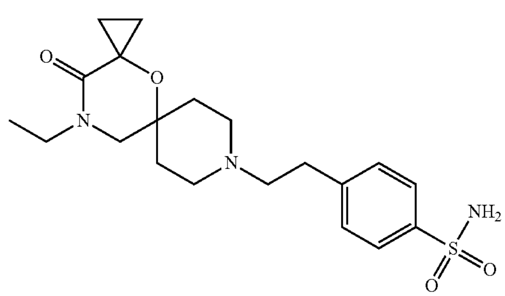 [SMILES: CCN1CC2(CCN(CCc3ccc(S(N)(=O)=O)cc3)CC2)OC2(CC2)C1=O] | 4-(2-{12-ethyl-13-oxo-4-oxa-8,12-diazadispiro[2.1.5.3]tridecan-8-yl}ethyl)benzene-1-sulfonamide | 2.80 | 408 |
| 16 | 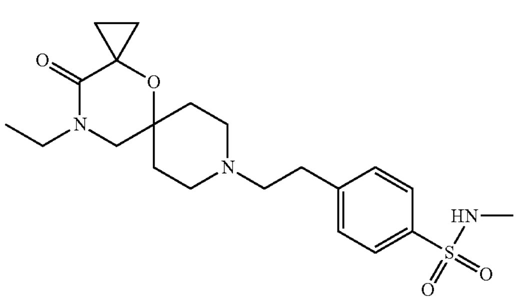 [SMILES: CCN1CC2(CCN(CCc3ccc(S(=O)(=O)NC)cc3)CC2)OC2(CC2)C1=O] | 4-(2-{12-ethyl-13-oxo-4-oxa-8,12-diazadispiro[2.1.5.3]tridecan-8-yl}ethyl)-N-methylbenzene-1-sulfonamide | 3.13 | 422 |

-continued

| EX | Structure | Chemical name | Ret time (min) | MS (M + H) |
|---|---|---|---|---|
| 17 | 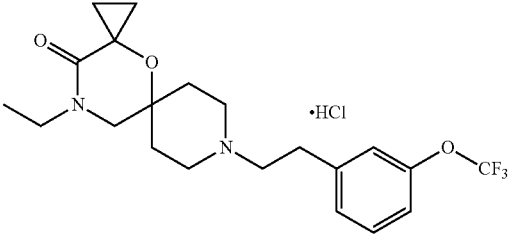 [SMILES: CCN1CC2(CCN(CCc3cccc(OC(F)(F)F)c3)CC2)OC2(CC2)C1=O ; Cl] | 12-ethyl-8-{2-[3-(trifluoromethoxy)phenyl]ethyl}-4-oxa-8,12-diazadispiro[2.1.5.3]tridecan-13-one hydrochloride | 4.59 | 413 |
| 18 | 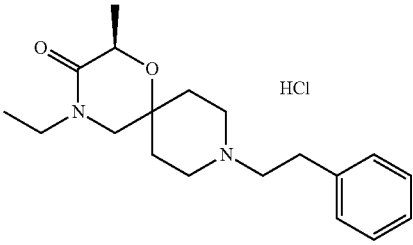 [SMILES: CCN1CC2(CCN(CCc3ccccc3)CC2)O[C@H](C)C1=O ; Cl] | (R)-4-ethyl-2-methyl-9-phenethyl-1-oxa-4,9-diazaspiro[5.5]undecan-3-one hydrochloride (2*) | 3.56 | 317 |
| 19 | 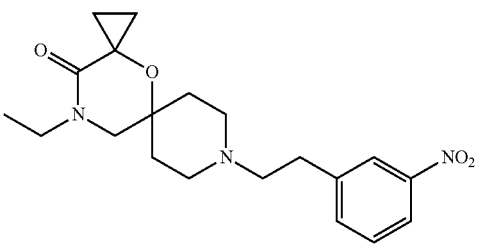 | 12-ethyl-8-(3-nitrophenethyl)-4-oxa-8,12-diazadispiro[2.1.5.3]tridecan-13-one | 3.61 | 374 |
| 20 | 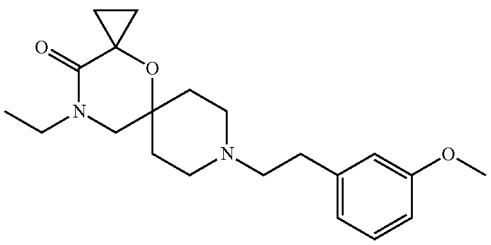 [SMILES: CCN1CC2(CCN(CCc3cccc(OC)c3)CC2)OC2(CC2)C1=O] | 12-ethyl-8-(3-methoxyphenethyl)-4-oxa-8,12-diazadispiro[2.1.5.3]tridecan-13-one | 3.66 | 359.1 |
| 21 | 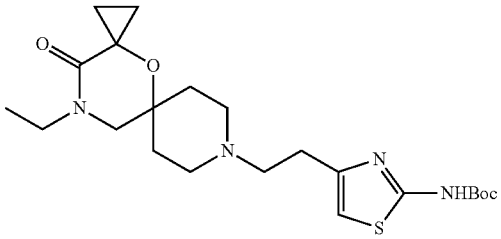 [SMILES: CCN1CC2(CCN(CCc3csc(NC(=O)OC(C)(C)C)n3)CC2)OC2(CC2)C1=O] | tert-butyl (4-(2-(12-ethyl-13-oxo-4-oxa-8,12-diazadispiro[2.1.5.3]tridecan-8-yl)ethyl)thiazol-2-yl)carbamate | 3.80 | 451.1 |
| 22 | 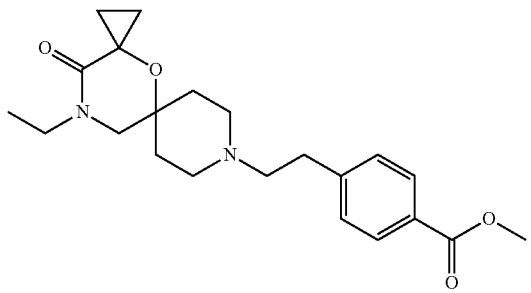 [SMILES: CCN1CC2(CCN(CCc3ccc(C(=O)OC)cc3)CC2)OC2(CC2)C1=O] | methyl 4-(2-{12-ethyl-13-oxo-4-oxa-8,12-diazadispiro[2.1.5.3]tridecan-8-yl}ethyl)benzoate | 3.73 | 387.1 |

-continued

| EX | Structure | Chemical name | Ret time (min) | MS (M + H) |
|---|---|---|---|---|
| 23 | 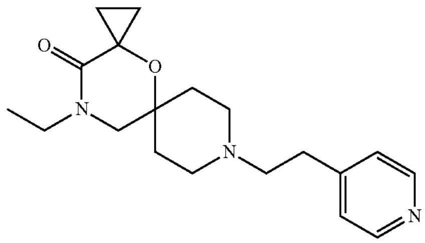 [SMILES: CCN1CC2(CCN(CCc3ccncc3)CC2)OC2(CC2)C1=O] | 12-ethyl-8-[2-(pyridin-4-yl)ethyl]-4-oxa-8,12-diazadispiro[2.1.5.3]tridecan-13-one | 2.74 | 330.2 |
| 24 | 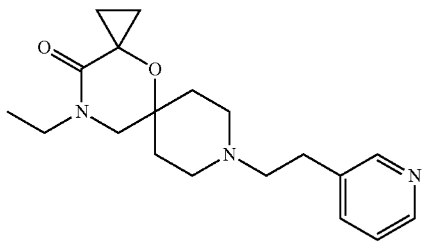 [SMILES: CCN1CC2(CCN(CCc3cccnc3)CC2)OC2(CC2)C1=O] | 12-ethyl-8-[2-(pyridin-3-yl)ethyl]-4-oxa-8,12-diazadispiro[2.1.5.3]tridecan-13-one | 2.77 | 330.2 |
| 25 | 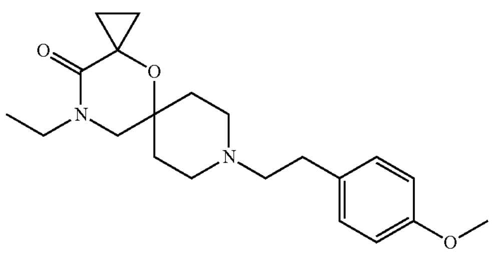 [SMILES: CCN1CC2(CCN(CCc3ccc(OC)cc3)CC2)OC2(CC2)C1=O] | 12-ethyl-8-(4-methoxyphenethyl)-4-oxa-8,12-diazadispiro[2.1.5.3]tridecan-13-one | 3.69 | 359.2 |
| 26 | 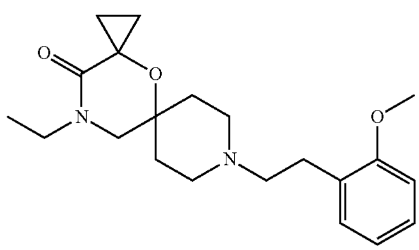 [SMILES: CCN1CC2(CCN(CCc3ccccc3OC)CC2)OC2(CC2)C1=O] | 12-ethyl-8-(2-methoxyphenethyl)-4-oxa-8,12-diazadispiro[2.1.5.3]tridecan-13-one | 3.83 | 359.2 |
| 27 | 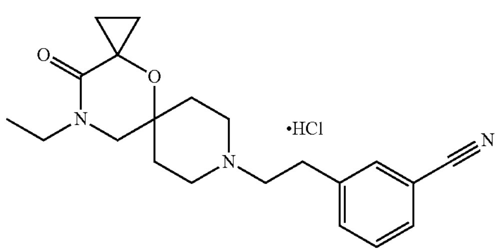 [SMILES: CCN1CC2(CCN(CCc3cccc(C#N)c3)CC2)OC2(CC2)C1=O ; Cl] | 3-(2-{12-ethyl-13-oxo-4-oxa-8,12-diazadispiro[2.1.5.3]tridecan-8-yl}ethyl)benzonitrile hydrochloride | 3.50 | 354.2 |
| 28 | 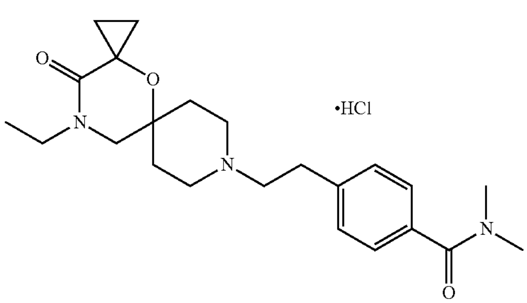 [SMILES: CCN1CC2(CCN(CCc3ccc(C(=O)N(C)C)cc3)CC2)OC2(CC2)C1=O ; Cl] | 4-(2-{12-ethyl-13-oxo-4-oxa-8,12-diazadispiro[2.1.5.3]tridecan-8-yl}ethyl)-N,N-dimethylbenzamide hydrochloride | 3.06 | 400.2 |

| EX | Structure | Chemical name | Ret time (min) | MS (M + H) |
|---|---|---|---|---|
| 29 | 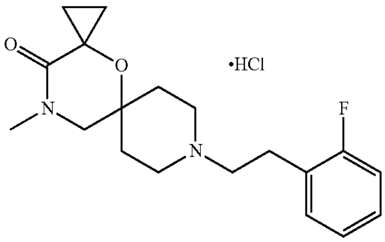 [SMILES: CN1CC2(CCN(CCc3ccccc3F)CC2)OC2(CC2)C1=O ; Cl] | 8-[2-fluorophenethyl]-12-methyl-4-oxa-8,12-diazadispiro[2.1.5.3]tridecan-13-one hydrochloride | 3.72 | 333.1 |
| 30 | 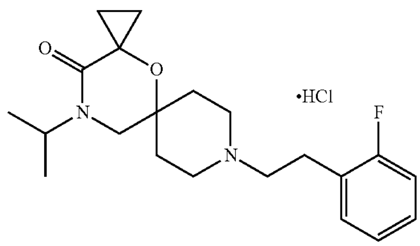 [SMILES: CC(C)N1CC2(CCN(CCc3ccccc3F)CC2)OC2(CC2)C1=O ; Cl] | 8-[2-fluorophenethyl]-12-isopropyl-4-oxa-8,12-diazadispiro[2.1.5.3]tridecan-13-one hydrochloride | 4.22 | 361.2 |
| 31 | 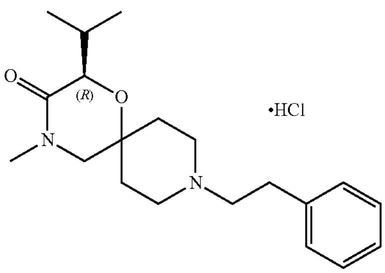 | (R)-2-isopropyl-4-methyl-9-phenethyl-1-oxa-4,9-diazaspiro[5.5]undecan-3-one hydrochloride | 4.20 | 331.2 |
| 32 | 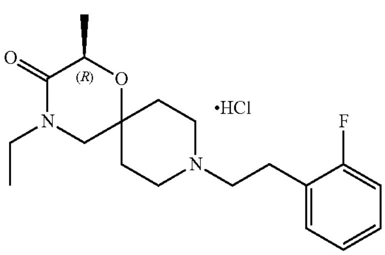 | (R)-4-ethyl-9-(2-fluorophenethyl)-2-methyl-1-oxa-4,9-diazaspiro[5.5]undecan-3-one hydrochloride | 3.78 | 335.2 |
| 33 | 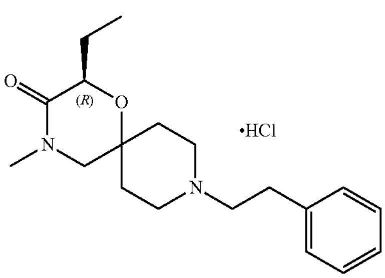 | (R)-2-ethyl-4-methyl-9-phenethyl-1-oxa-4,9-diazaspiro[5.5]undecan-3-one hydrochloride | 3.77 | 317.2 |
| 34 | 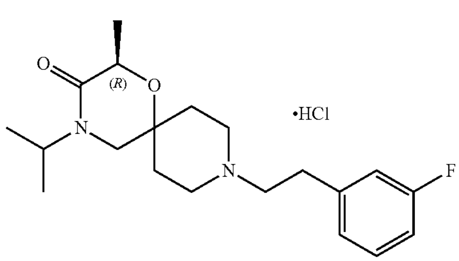 | (R)-9-(3-fluorophenethyl)-4-isopropyl-2-methyl-1-oxa-4,9-diazaspiro[5.5]undecan-3-one hydrochloride | 3.99 | 349.2 |

-continued

| EX | Structure | Chemical name | Ret time (min) | MS (M + H) |
|---|---|---|---|---|
| 35 | 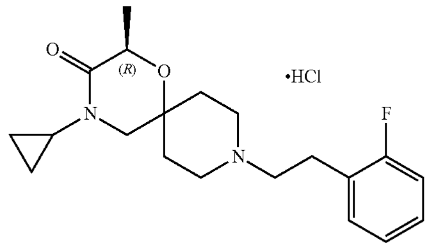 | (R)-4-cyclopropyl-9-(2-fluorophenethyl)-2-methyl-1-oxa-4,9-diazaspiro[5.5]undecan-3-one hydrochloride | 3.81 | 347.2 |
| 36 | 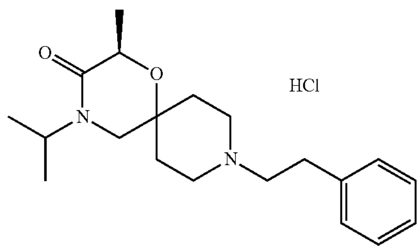 [SMILES: CC(C)N1CC2(CCN(CCc3ccccc3)CC2)O[C@H](C)C1=O ; Cl] | (R)-4-isopropyl-2-methyl-9-phenethyl-1-oxa-4,9-diazaspiro[5.5]undecan-3-one hydrochloride (3*) | 3.86 | 331 |
| 37 | 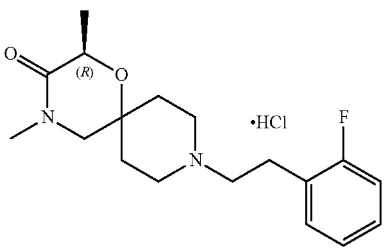 | (R)-9-(2-fluorophenethyl)-2,4-dimethyl-1-oxa-4,9-diazaspiro[5.5]undecan-3-one hydrochloride | 3.53 | 321.1 |
| 38 | 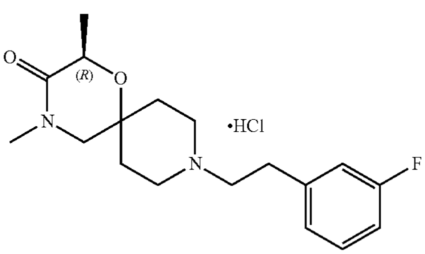 | (R)-9-(3-fluorophenethyl)-2,4-dimethyl-1-oxa-4,9-diazaspiro[5.5]undecan-3-one hydrochloride | 3.54 | 321.1 |
| 39 | 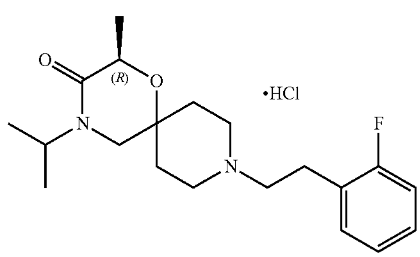 | (R)-9-(2-fluorophenethyl)-4-isopropyl-2-methyl-1-oxa-4,9-diazaspiro[5.5]undecan-3-one hydrochloride | 4.03 | 349.2 |
| 40 | 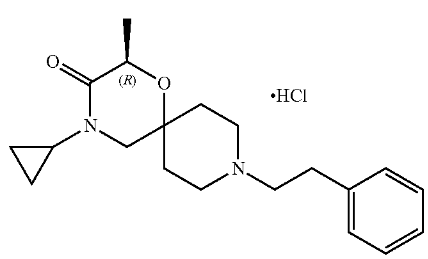 | (R)-4-cyclopropyl-2-methyl-9-phenethyl-1-oxa-4,9-diazaspiro[5.5]undecan-3-one hydrochloride | 3.70 | 329.2 |

-continued

| EX | Structure | Chemical name | Ret time (min) | MS (M + H) |
|---|---|---|---|---|
| 41 | 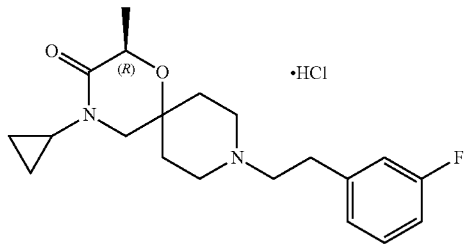 | (R)-4-cyclopropyl-9-(3-fluorophenethyl)-2-methyl-1-oxa-4,9-diazaspiro[5.5]undecan-3-one hydrochloride | 3.85 | 347.2 |
| 42 | 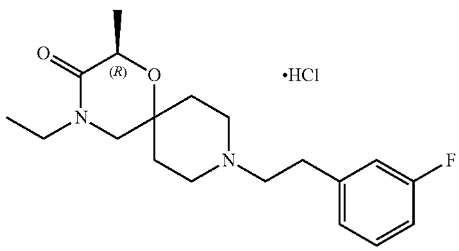 | (R)-4-ethyl-9-(3-fluorophenethyl)-2-methyl-1-oxa-4,9-diazaspiro[5.5]undecan-3-one hydrochloride | 3.80 | 335.2 |
| 43 | 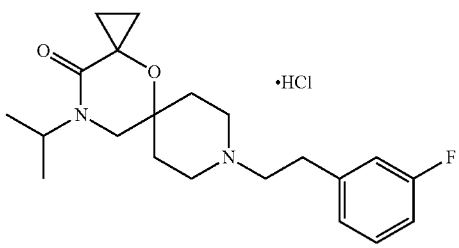 [SMILES: CC(C)N1CC2(CCN(CCc3cccc(F)c3)CC2)OC2(CC2)C1=O ; Cl] | 8-(3-fluorophenethyl)-12-isopropyl-4-oxa-8,12-diazadispiro[2.1.5.3]tridecan-13-one hydrochloride | 4.25 | 361.2 |
| 44 | 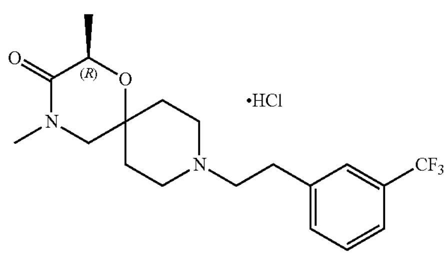 | (R)-2,4-dimethyl-9-(3-(trifluoromethyl)phenethyl)-1-oxa-4,9-diazaspiro[5.5]undecan-3-one hydrochloride | 3.98 | 371.2 |
| 45 | 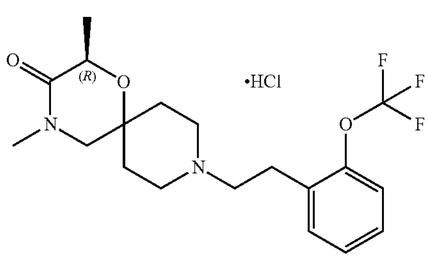 | (R)-2,4-dimethyl-9-(2-(trifluoromethoxy)phenethyl)-1-oxa-4,9-diazaspiro[5.5]undecan-3-one hydrochloride | 4.15 | 387.1 |
| 46 | 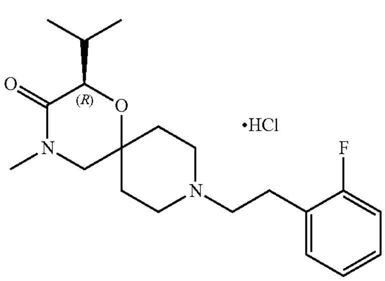 | (R)-9-(2-fluorophenethyl)-2-isopropyl-4-methyl-1-oxa-4,9-diazaspiro[5.5]undecan-3-one hydrochloride | 4.25 | 349.2 |

-continued

| EX | Structure | Chemical name | Ret time (min) | MS (M + H) |
|---|---|---|---|---|
| 47 | 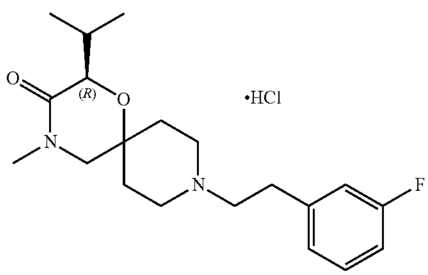 | (R)-9-(3-fluorophenethyl)-2-isopropyl-4-methyl-1-oxa-4,9-diazaspiro[5.5]undecan-3-one hydrochloride | 4.25 | 349.2 |
| 48 | 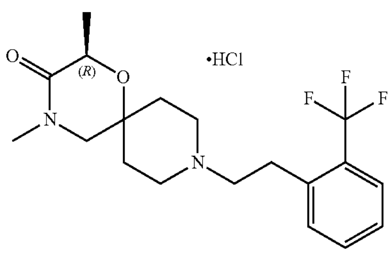 | (R)-2,4-dimethyl-9-(2-(trifluoromethyl)phenethyl)-1-oxa-4,9-diazaspiro[5.5]undecan-3-one hydrochloride | 3.93 | 371.2 |
| 49 | 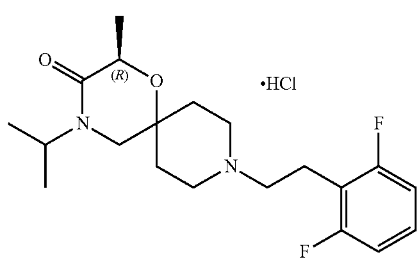 | (R)-9-(2,6-difluorophenethyl)-4-isopropyl-2-methyl-1-oxa-4,9-diazaspiro[5.5]undecan-3-one hydrochloride | 4.06 | 367.2 |
| 50 | 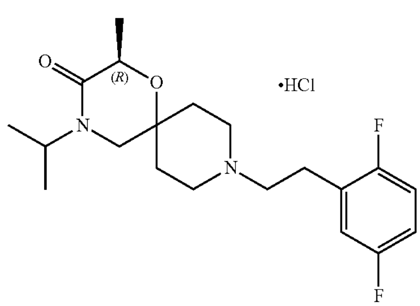 | (R)-9-(2,5-difluorophenethyl)-4-isopropyl-2-methyl-1-oxa-4,9-diazaspiro[5.5]undecan-3-one hydrochloride | 4.02 | 367.2 |
| 51 | 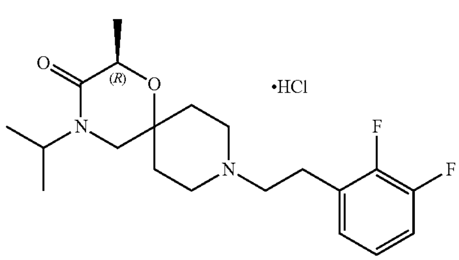 | (R)-9-(2,3-difluorophenethyl)-4-isopropyl-2-methyl-1-oxa-4,9-diazaspiro[5.5]undecan-3-one hydrochloride | 4.03 | 367.2 |

| EX | Structure | Chemical name | Ret time (min) | MS (M + H) |
|----|-----------|---------------|----------------|------------|
| 52 | 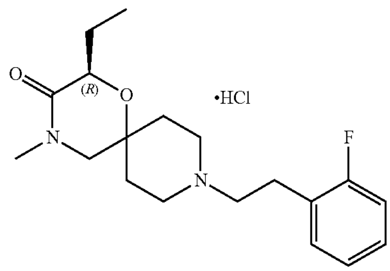 | (R)-2-ethyl-9-(2-fluorophenethyl)-4-methyl-1-oxa-4,9-diazaspiro[5.5]undecan-3-one hydrochloride | 3.75 | 335.2 |
| 53 | 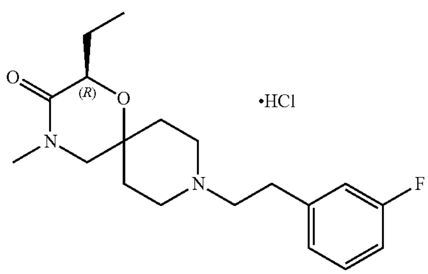 | (R)-2-ethyl-9-(3-fluorophenethyl)-4-methyl-1-oxa-4,9-diazaspiro[5.5]undecan-3-one hydrochloride | 3.75 | 335.2 |

Where indicated, the hydrochloride salts were prepared as described in example 1
1*. Alternatively prepared by chiral preparative HPLC separation of the racemic compound. Conditions: Column: OJ; Temperature: ambient; Flow: 0.8 mL/min; Mobile phase: n-Heptane/IPA 95/5 v/v
2*. Alternatively prepared by chiral preparative HPLC separation of the racemic compound. Conditions: Column: OJ; Temperature: ambient; Flow: 0.8 mL/min; Mobile phase: n-Heptane/EtOH 95/5 v/v
3*. Alternatively prepared by chiral preparative HPLC separation of the racemic compound. Conditions: Column: Chiralpak IA; Temperature: ambient; Flow: 0.4 mL/min; Mobile phase: n-Heptane/EtOH 98/2 v/v
4*. Compound obtained as by-product of previous example

Alternative Method for the Synthesis of Example 11

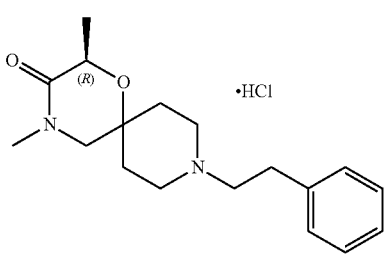

Step 1. ((S)-2-chloro-N-((4-hydroxy-1-phenethylpiperidin-4-yl)methyl)-N-methylpropanamide. To a solution of intermediate 2G (0.500 g, 79 wt %, 1.59 mmol) in ethyl acetate (8 mL), a solution of $K_2CO_3$ (0.779 g, 5.64 mmol) in water (7 mL) was added. After cooling to 0° C., a solution of (S)-2-chloropropanoyl chloride (0.31 g, 2.42 mmol) in ethyl acetate (1 mL) was added dropwise and the reaction mixture was stirred at 0° C. for 30 min. $NaHCO_3$ sat solution was then added, the layers were separated and the aqueous phase was extracted with ethyl acetate. The organic phases were combined, dried over $MgSO_4$, filtered and concentrated to dryness to give the title compound (0.500 g, 91% yield). HPLC retention time: 3.13 min; MS: 339 (M+H).

Step 2. Title compound: A solution of the crude product obtained in step 1 in THF (15 mL) was cooled to −78° C. using a dry ice/acetone bath. After addition of potassium tert-butoxide solution (1.62 mL, 1M in THF, 1.62 mmol), the reaction mixture was stirred at −78° C. for 30 min. $NH_4Cl$ sat solution was then added and the aqueous phase was extracted with ethyl acetate. The organic phases were combined, dried over $MgSO_4$, filtered and concentrated under vacuum to give the title compound (0.400 g, 90% yield). HPLC retention time: 3.30 min; MS: 303 (M+H). Optical purity: 93.5% ee, determined by chiral HPLC: Column: OJ 250×4.6 mm, 10µ; temperature: 25° C.; flow: 0.5 mL/min; eluent: heptane/ethanol 90:10.

The previous compound was converted to its hydrochloride salt as described in example 1.

This method was used for the preparation of example 54 using suitable starting materials:

| EX | Structure | Chemical name | Ret time (min) | MS (M + H) |
|---|---|---|---|---|
| 54 | 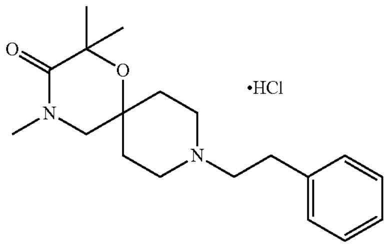 [SMILES: CN1CC2(CCN(CCc3ccccc3)CC2)OC(C)(C)C1=O ; Cl] | 2,2,4-trimethyl-9-phenethyl-1-oxa-4,9-diazaspiro[5.5]undecan-3-one hydrochloride | 3.48 | 317.2 |

Example 55: 12-methyl-8-phenethyl-4-oxa-8,12-diazadispiro[2.1.5.3]tridecan-13-one hydrochloride

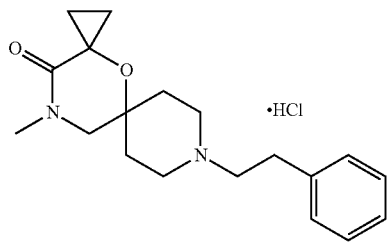 [SMILES: CN1CC2(CCN(CCc3ccccc3)CC2)OC2(CC2)C1=O ; Cl]

To a solution of intermediate 4D (0.106 g, 0.353 mmol) in dry DMF (3.5 mL), NaH (16 mg, 60 wt % in mineral oil, 0.233 mmol) was added. The reaction mixture was stirred at r.t. for 30 min, then iodomethane (0.024 mL, 0.388 mmol) was added and the resulting mixture was stirred at r.t. overnight. Water was added to the reaction mixture and it was extracted with dichloromethane. The organic phases were combined, washed with brine, dried over MgSO$_4$, filtered and concentrated to dryness. The residue was purified by flash chromatography, silica gel, gradient dichloromethane to methanol:dichloromethane (1:4) to give the title compound as its free base (25 mg, 23% yield).

The previous compound was converted to its hydrochloride salt as described in example 1.

HPLC retention time: 3.53 min; MS: 315.1 (M+H).

Example 56: 8-(3-aminophenethyl)-12-ethyl-4-oxa-8,12-diazadispiro[2.1.5.3]tridecan-13-one

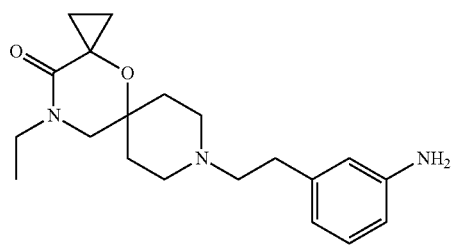 [SMILES: CCN1CC2(CCN(CCc3cccc(N)c3)CC2)OC2(CC2)C1=O]

A mixture of example 19 (0.139 g, 0.372 mmol) and palladium (14 mg, 10% wt on charcoal) in methanol (3 mL) was stirred at r.t. under 4 bars of H$_2$ overnight. Then, the solids were filtered off, and the solvent was removed under vacuum to give the title compound (0.129 g, quant. yield). HPLC retention time: 2.98 min; MS: 344.1 (M+H).

Example 57: N-[3-(2-{12-ethyl-13-oxo-4-oxa-8,12-diazadispiro[2.1.5.3]tridecan-8-yl}ethyl)phenyl]acetamide

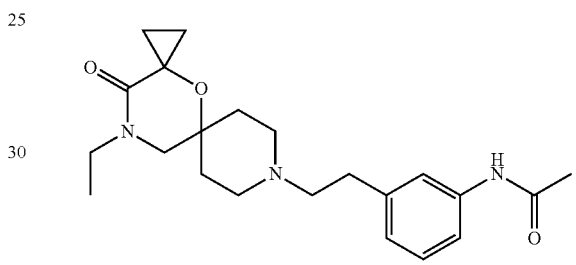

To a solution of example 56 (0.060 g, 0.175 mmol) and triethylamine (0.036 mL, 0.262 mmol) in dichloromethane (1.8 mL), acetyl chloride (0.014 mL, 0.192 mmol) was added dropwise at 0° C. The reaction mixture was stirred at r.t. overnight. Water was added and the aqueous phase was washed with dichloromethane, basified with 1M NaOH aqueous solution and extracted with dichloromethane. The organic phases were combined, dried over MgSO$_4$, filtered and concentrated to dryness. The residue was purified by eluting through an acidic ion exchange resin cartridge (SCX), to give the title compound (0.048 g, 72% yield). HPLC retention time: 3.00 min; MS: 386.1 (M+H).

Example 58: [3-(2-{12-ethyl-13-oxo-4-oxa-8,12-diazadispiro[2.1.5.3]tridecan-8-yl}ethyl)phenyl]urea

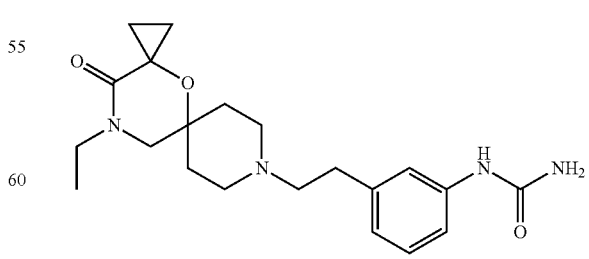

To a solution of example 56 (0.060 g, 0.175 mmol) in a mixture of acetic acid:water 1:1.5 (1 mL), potassium cyanate (0.021 g, 0.262 mmol) was added, and the reaction mixture was stirred at r.t. overnight. NaHCO₃ aqueous sat solution was added, and the aqueous phase was washed with dichloromethane, basified with 1M NaOH aqueous solution and extracted with dichloromethane. The organic phases were combined, dried over MgSO₄, filtered and concentrated under vacuum. The residue was purified by eluting through an acidic ion exchange resin cartridge (SCX) to give the title compound (0.031 g, 46% yield). HPLC retention time: 2.79 min; MS: 387.1 (M+H).

Example 59: 4-(2-{12-ethyl-13-oxo-4-oxa-8,12-diazadispiro[2.1.5.3]tridecan-8-yl}ethyl)-N-methyl-benzamide hydrochloride

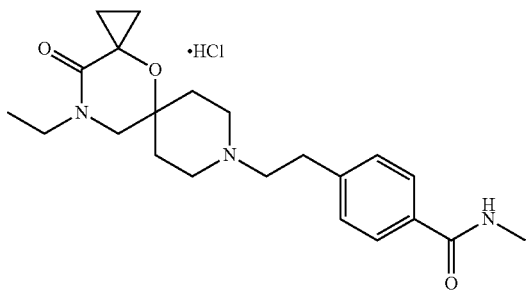 [SMILES: CCN1CC2(CCN(CCc3ccc(C(=O)NC)cc3)CC2)OC2(CC2)C1=O ; Cl]

A mixture of example 22 (0.054 g, 0.140 mmol) and methylamine solution (1 mL, 33% in ethanol, 8.1 mmol) was heated at 100° C. in a sealed tube overnight. It was then concentrated to dryness and the residue was purified by flash chromatography, silica gel, gradient dichloromethane to methanol:dichloromethane (1:4) to give the title compound as its free base (0.021 g, 39% yield).

The previous compound was converted to its hydrochloride salt as described in example 1.
HPLC retention time: 2.81 min; MS: 386.2 (M+H).

Example 60: 12-ethyl-8-(2-hydroxyphenethyl)-4-oxa-8,12-diazadispiro[2.1.5.3]tridecan-13-one

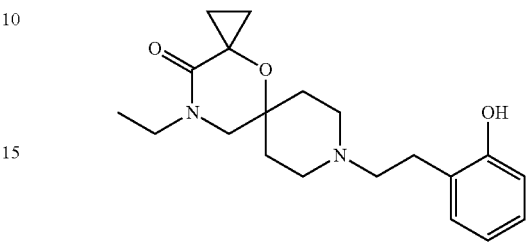

To a solution of example 26 (0.078 g, 0.217 mmol) in dichloromethane (2 mL), boron tribromide solution (0.65 mL, 1M in dichloromethane, 0.65 mmol) was added dropwise at −78° C. The reaction mixture was allowed to warm to r.t. over a period of 2 h. Then, 1M NaOH aqueous solution was added until pH 8-9 and it was extracted with dichloromethane. The organic phases were combined, washed with brine, dried over MgSO₄, filtered and concentrated to dryness. The residue was purified by flash chromatography, silica gel, gradient dichloromethane to methanol:dichloromethane (1:4) to give the title compound (0.032 g, 43% yield). HPLC retention time: 3.71 min; MS: 345.2 (M+H).

This method was used for the preparation of examples 61-62 starting from the corresponding examples described above:

| EX | Structure | Chemical name | Ret time (min) | MS (M + H) |
|---|---|---|---|---|
| 61 | 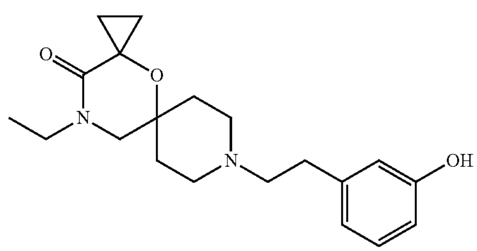 [SMILES: CCN1CC2(CCN(CCc3cccc(O)c3)CC2)OC2(CC2)C1=O] | 12-ethyl-8-(3-hydroxyphenethyl)-4-oxa-8,12-diazadispiro[2.1.5.3]tridecan-13-one | 3.05 | 345.1 |
| 62 | 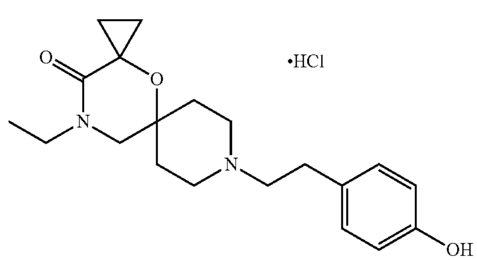 [SMILES: CCN1CC2(CCN(CCc3ccc(O)cc3)CC2)OC2(CC2)C1=O ; Cl] | 12-ethyl-8-(4-hydroxyphenethyl)-4-oxa-8,12-diazadispiro[2.1.5.3]tridecan-13-one hydrochloride | 2.92 | 345.2 |

Where indicated, the hydrochloride salts were prepared as described in example 1.

Example 63: 8-[2-(2-aminothiazol-4-yl)ethyl]-12-ethyl-4-oxa-8,12-diazadispiro [2.1.5.3]tridecan-13-one

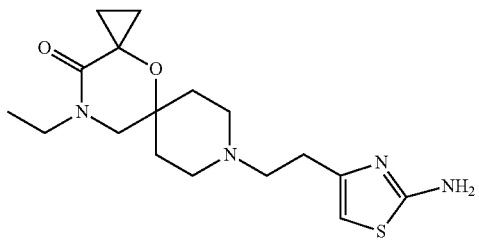 [SMILES: CCN1CC2(CCN(CCc3csc(N)n3)CC2)OC2(CC2)C1=O]

To a solution of example 21 (0.070 g, 0.155 mmol) in dichloromethane (2.2 mL), trifluoroacetic acid (0.60 mL, 7.78 mmol) was added. The reaction mixture was stirred at r.t. overnight. Then, NaHCO$_3$ sat solution was added. The organic phase was separated and it was washed with water. The combined aqueous phases were back extracted with dichloromethane. The organic phases were combined, dried over MgSO$_4$, filtered and concentrated to dryness. The residue was purified by flash chromatography, C$_{18}$, gradient aqueous NH$_4$HCO$_3$ (pH 8) to acetonitrile to give the title compound (0.015 g, 28% yield). HPLC retention time: 2.60 min; MS: 351.2 (M+H).

Examples 64 to 94 were prepared according to the procedure described in Example 7, using suitable starting materials:

| EX | Structure | Chemical name | Ret time (min) | MS (M + H) |
|---|---|---|---|---|
| 64 | 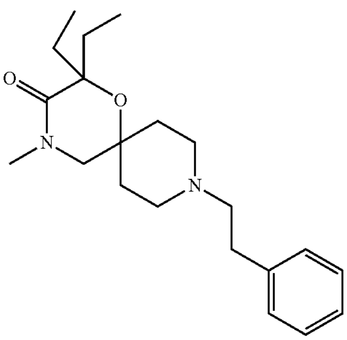 [SMILES: CCC1(CC)OC2(CCN(CCc3ccccc3)CC2)CN(C)C1=O] | 2,2-diethyl-4-methyl-9-phenethyl-1-oxa-4,9-diazaspiro[5.5]undecan-3-one | 4.19 | 345.2 |
| 65 | 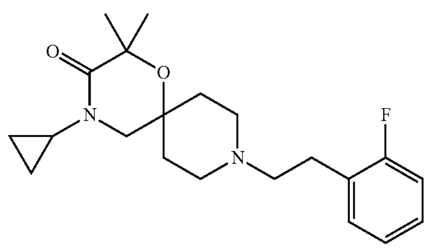 [SMILES: CC1(C)OC2(CCN(CCc3ccccc3F)CC2)CN(C2CC2)C1=O] | 4-cyclopropyl-9-(2-fluorophenethyl)-2,2-dimethyl-1-oxa-4,9-diazaspiro[5.5]undecan-3-one | 4.06 (method B) | 361.2 |
| 66 | 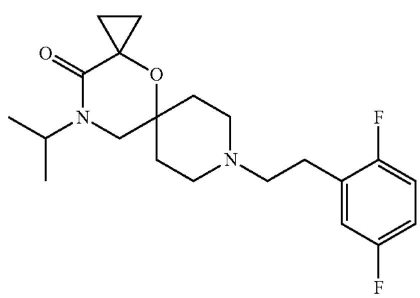 [SMILES: CC(C)N1CC2(CCN(CCc3cc(F)ccc3F)CC2)OC2(CC2)C1=O] | 8-(2,5-difluorophenethyl)-12-isopropyl-4-oxa-8,12-diazadispiro[2.1.5.3]tridecan-13-one | 4.28 | 379.2 |
| 67 | 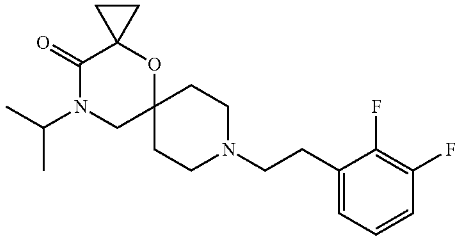 [SMILES: CC(C)N1CC2(CCN(CCc3cccc(F)c3F)CC2)OC2(CC2)C1=O] | 8-(2,3-difluorophenethyl)-12-isopropyl-4-oxa-8,12-diazadispiro[2.1.5.3]tridecan-13-one | 4.26 | 379.2 |

-continued

| EX | Structure | Chemical name | Ret time (min) | MS (M + H) |
|----|-----------|---------------|----------------|------------|
| 68 | 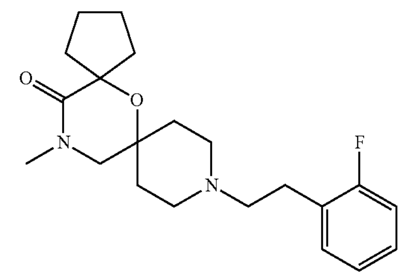 [SMILES: CN1CC2(CCN(CCc3ccccc3F)CC2)OC2(CCCC2)C1=O] | 10-(2-fluorophenethyl)-14-methyl-6-oxa-10,14-diazadispiro[4.1.5.3]pentadecan-15-one | 4.19 | 361.2 |
| 69 | 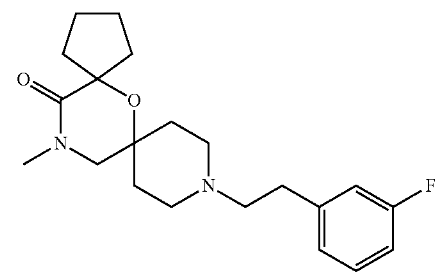 [SMILES: CN1CC2(CCN(CCc3cccc(F)c3)CC2)OC2(CCCC2)C1=O] | 10-(3-fluorophenethyl)-14-methyl-6-oxa-10,14-diazadispiro[4.1.5.3]pentadecan-15-one | 4.18 | 361.2 |
| 70 | 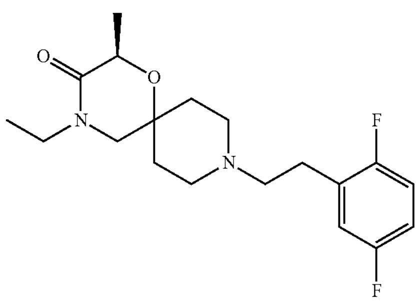 [SMILES: CCN1CC2(CCN(CCc3cc(F)ccc3F)CC2)O[C@H](C)C1=O] | (R)-9-(2,5-difluorophenethyl)-4-ethyl-2-methyl-1-oxa-4,9-diazaspiro[5.5]undecan-3-one | 3.77 | 353.1 |
| 71 | 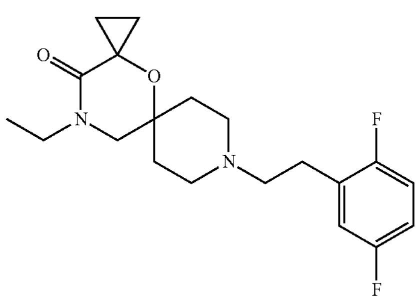 [SMILES: CCN1CC2(CCN(CCc3cc(F)ccc3F)CC2)OC2(CC2)C1=O] | 8-(2,5-difluorophenethyl)-12-ethyl-4-oxa-8,12-diazadispiro[2.1.5.3]tridecan-13-one | 4 | 365.2 |
| 72 | 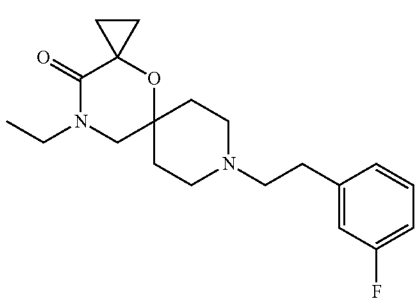 [SMILES: CCN1CC2(CCN(CCc3cccc(F)c3)CC2)OC2(CC2)C1=O] | 12-ethyl-8-(3-fluorophenethyl)-4-oxa-8,12-diazadispiro[2.1.5.3]tridecan-13-one | 3.87 | 347.2 |

| EX | Structure | Chemical name | Ret time (min) | MS (M + H) |
|---|---|---|---|---|
| 73 | 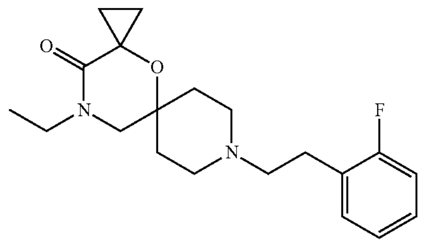 [SMILES: CCN1CC2(CCN(CCc3ccccc3F)CC2)OC2(CC2)C1=O] | 12-ethyl-8-(2-fluorophenethyl)-4-oxa-8,12-diazadispiro[2.1.5.3]tridecan-13-one | 3.88 | 347.2 |
| 74 | 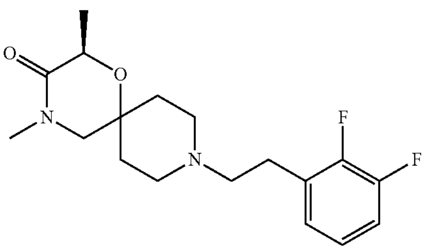 [SMILES: C[C@H]1OC2(CCN(CCc3cccc(F)c3F)CC2)CN(C)C1=O] | (R)-9-(2,3-difluorophenethyl)-2,4-dimethyl-1-oxa-4,9-diazaspiro[5.5]undecan-3-one | 3.56 | 339.1 |
| 75 | 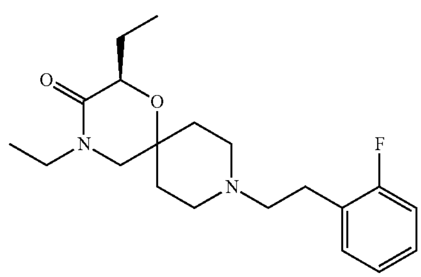 [SMILES: CC[C@H]1OC2(CCN(CCc3ccccc3F)CC2)CN(CC)C1=O] | (R)-2,4-diethyl-9-(2-fluorophenethyl)-1-oxa-4,9-diazaspiro[5.5]undecan-3-one | 4.07 | 349.2 |
| 76 | 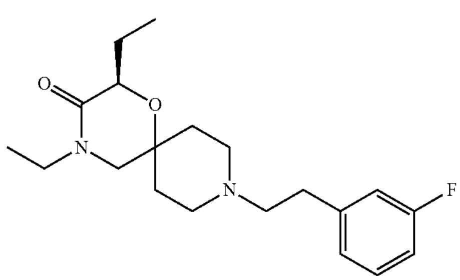 [SMILES: CC[C@H]1OC2(CCN(CCc3cccc(F)c3)CC2)CN(CC)C1=O] | (R)-2,4-diethyl-9-(3-fluorophenethyl)-1-oxa-4,9-diazaspiro[5.5]undecan-3-one | 4.07 | 349.2 |
| 77 | 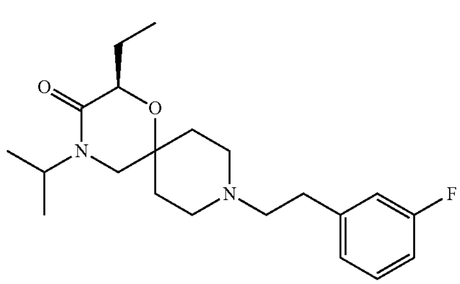 [SMILES: CC[C@H]1OC2(CCN(CCc3cccc(F)c3)CC2)CN(C(C)C)C1=O] | (R)-2-ethyl-9-(3-fluorophenethyl)-4-isopropyl-1-oxa-4,9-diazaspiro[5.5]undecan-3-one | 4.31 | 363.2 |

| EX | Structure | Chemical name | Ret time (min) | MS (M + H) |
|---|---|---|---|---|
| 78 | 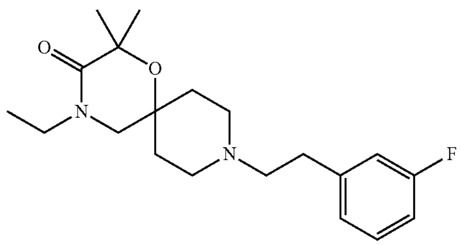 [SMILES: CCN1CC2(CCN(CCc3cccc(F)c3)CC2)OC(C)(C)C1=O] | 4-ethyl-9-(3-fluorophenethyl)-2,2-dimethyl-1-oxa-4,9-diazaspiro[5.5]undecan-3-one | 3.9 | 349.2 |
| 79 | 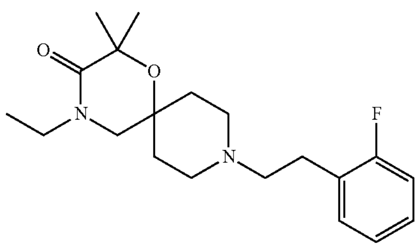 [SMILES: CCN1CC2(CCN(CCc3ccccc3F)CC2)OC(C)(C)C1=O] | 4-ethyl-9-(2-fluorophenethyl)-2,2-dimethyl-1-oxa-4,9-diazaspiro[5.5]undecan-3-one | 3.91 | 349.2 |
| 80 | 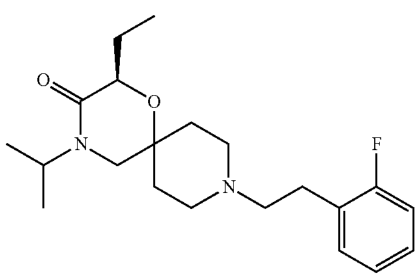 [SMILES: CC[C@H]1OC2(CCN(CCc3ccccc3F)CC2)CN(C(C)C)C1=O] | (R)-2-ethyl-9-(2-fluorophenethyl)-4-isopropyl-1-oxa-4,9-diazaspiro[5.5]undecan-3-one | 4.2 | 363.2 |
| 81 | 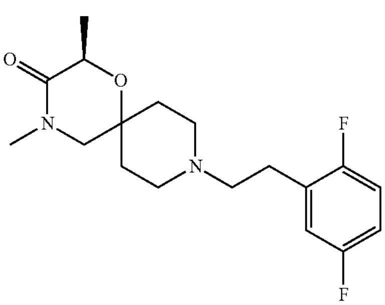 [SMILES: C[C@H]1OC2(CCN(CCc3cc(F)ccc3F)CC2)CN(C)C1=O] | (R)-9-(2,5-difluorophenethyl)-2,4-dimethyl-1-oxa-4,9-diazaspiro[5.5]undecan-3-one | 3.46 | 339.1 |
| 82 | 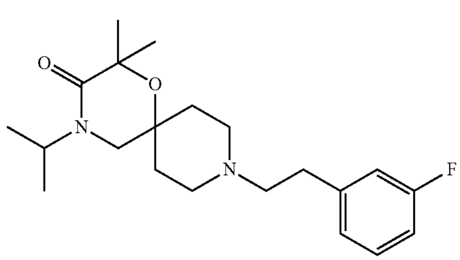 [SMILES: CC(C)N1CC2(CCN(CCc3cccc(F)c3)CC2)OC(C)(C)C1=O] | 9-(3-fluorophenethyl)-4-isopropyl-2,2-dimethyl-1-oxa-4,9-diazaspiro[5.5]undecan-3-one | 4.09 | 407.2 |

| EX | Structure | Chemical name | Ret time (min) | MS (M + H) |
|---|---|---|---|---|
| 83 | 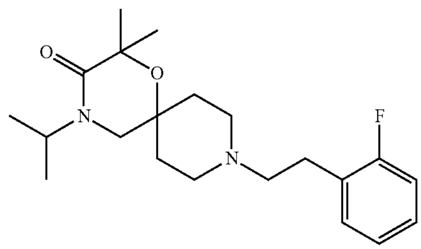 [SMILES: CC(C)N1CC2(CCN(CCc3ccccc3F)CC2)OC(C)(C)C1=O] | 9-(2-fluorophenethyl)-4-isopropyl-2,2-dimethyl-1-oxa-4,9-diazaspiro[5.5]undecan-3-one | 4.1 | 363.2 |
| 84 | 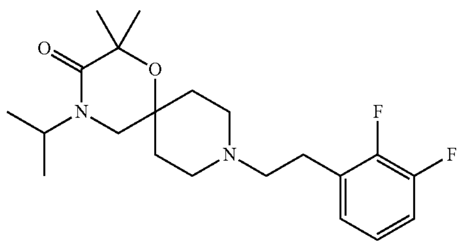 [SMILES: CC(C)N1CC2(CCN(CCc3cccc(F)c3F)CC2)OC(C)(C)C1=O] | 9-(2,3-difluorophenethyl)-4-isopropyl-2,2-dimethyl-1-oxa-4,9-diazaspiro[5.5]undecan-3-one | 4.42 (method B) | 381.2 |
| 85 | 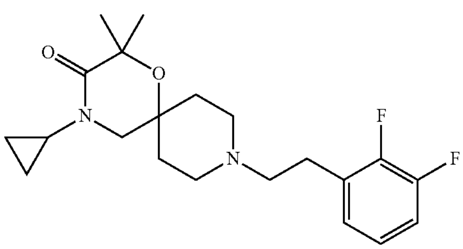 [SMILES: CC1(C)OC2(CCN(CCc3cccc(F)c3F)CC2)CN(C2CC2)C1=O] | 4-cyclopropyl-9-(2,3-difluorophenethyl)-2,2-dimethyl-1-oxa-4,9-diazaspiro[5.5]undecan-3-one | 4.19 (method B) | 379.2 |
| 86 | 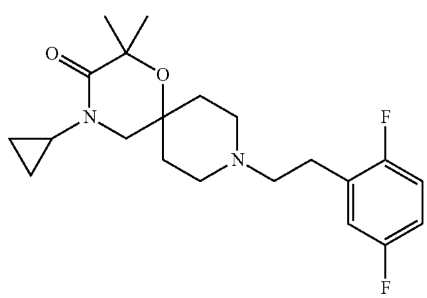 [SMILES: CC1(C)OC2(CCN(CCc3cc(F)ccc3F)CC2)CN(C2CC2)C1=O] | 4-cyclopropyl-9-(2,5-difluorophenethyl)-2,2-dimethyl-1-oxa-4,9-diazaspiro[5.5]undecan-3-one | 4.20 (method B) | 379.2 |
| 87 | 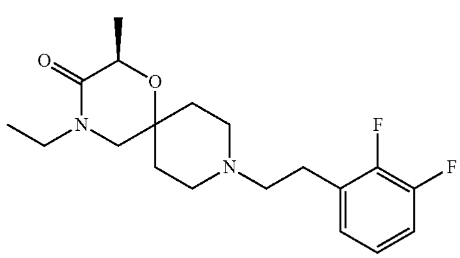 [SMILES: CCN1CC2(CCN(CCc3cccc(F)c3F)CC2)O[C@H](C)C1=O] | (R)-9-(2,3-difluorophenethyl)-4-ethyl-2-methyl-1-oxa-4,9-diazaspiro[5.5]undecan-3-one | 3.83 (method B) | 353.2 |

-continued

| EX | Structure | Chemical name | Ret time (min) | MS (M + H) |
|---|---|---|---|---|
| 88 | 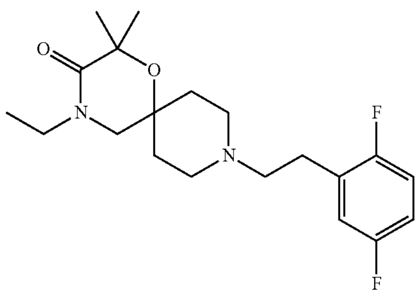 [SMILES: CCN1CC2(CCN(CCc3cc(F)ccc3F)CC2)OC(C)(C)C1=O] | 9-(2,5-difluorophenethyl)-4-ethyl-2,2-dimethyl-1-oxa-4,9-diazaspiro[5.5]undecan-3-one | 4.12 (method B) | 367.2 |
| 89 | 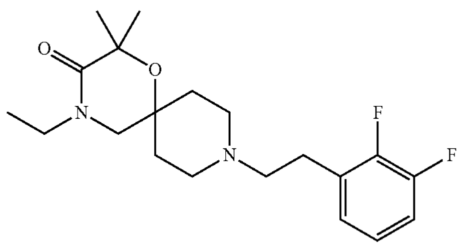 [SMILES: CCN1CC2(CCN(CCc3cccc(F)c3F)CC2)OC(C)(C)C1=O] | 9-(2,3-difluorophenethyl)-4-ethyl-2,2-dimethyl-1-oxa-4,9-diazaspiro[5.5]undecan-3-one | 4.13 (method B) | 367.2 |
| 90 | 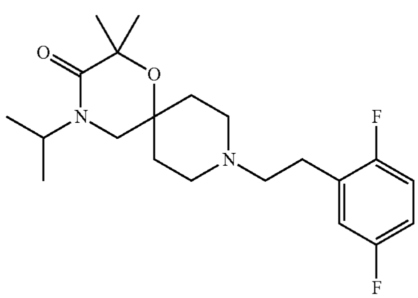 [SMILES: CC(C)N1CC2(CCN(CCc3cc(F)ccc3F)CC2)OC(C)(C)C1=O] | 9-(2,5-difluorophenethyl)-4-isopropyl-2,2-dimethyl-1-oxa-4,9-diazaspiro[5.5]undecan-3-one | 4.39 (method B) | 381.2 |
| 91 | 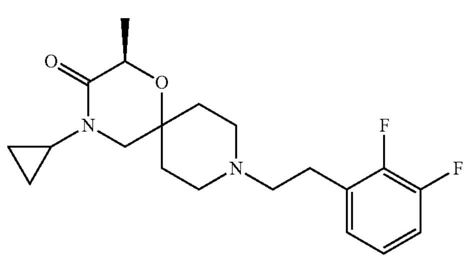 [SMILES: C[C@H]1OC2(CCN(CCc3cccc(F)c3F)CC2)CN(C2CC2)C1=O] | (R)-4-cyclopropyl-9-(2,3-difluorophenethyl)-2-methyl-1-oxa-4,9-diazaspiro[5.5]undecan-3-one | 3.90 (method B) | 365.1 |
| 92 | 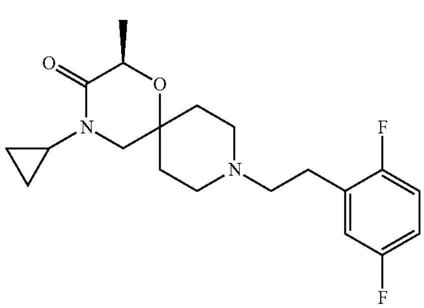 [SMILES: C[C@H]1OC2(CCN(CCc3cc(F)ccc3F)CC2)CN(C2CC2)C1=O] | (R)-4-cyclopropyl-9-(2,5-difluorophenethyl)-2-methyl-1-oxa-4,9-diazaspiro[5.5]undecan-3-one | 3.89 (method B) | 365.2 |

| EX | Structure | Chemical name | Ret time (min) | MS (M + H) |
|---|---|---|---|---|
| 93 | 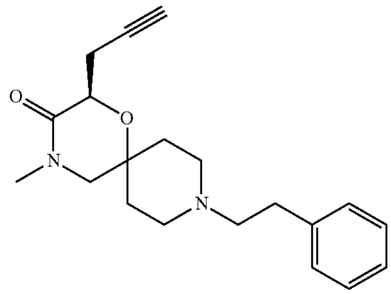 [SMILES: C#CC[C@H]1OC2(CCN(CCc3ccccc3)CC2)CN(C)C1=O] | (R)-4-methyl-9-phenethyl-2-(prop-2-yn-1-yl)-1-oxa-4,9-diazaspiro[5.5]undecan-3-one (1*) | 3.47 | 327.2 |
| 94 | 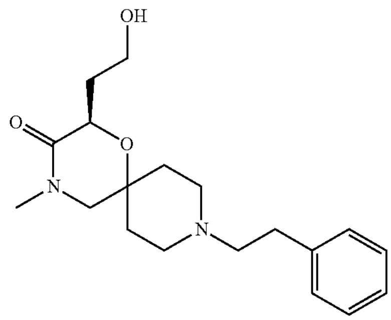 [SMILES: CN1CC2(CCN(CCc3ccccc3)CC2)O[C@H](CCO)C1=O] | (R)-2-(2-hydroxyethyl)-4-methyl-9-phenethyl-1-oxa-4,9-diazaspiro[5.5]undecan-3-one (2*) | 2.74 | 333.2 |

1*. Obtained by chiral preparative HPLC resolution of the racemic compound. Conditions: Column: AS-H; Temperature: ambient; Flow: 15 mL/min; Mobile phase: n-Heptane/(EtOH + 0.33% DEA) 85/15 v/v
2*. Obtained by chiral preparative HPLC resolution of the racemic compound. Conditions: Column: AS-H; Temperature: ambient; Flow: 10 mL/min; Mobile phase: n-Heptane/(IPA + 0.33% DEA) 70/30 v/v Example 95: (R)-2-benzyl-4-methyl-9-phenethyl-1-oxa-4,9-diazaspiro[5.5]undecan-3-one

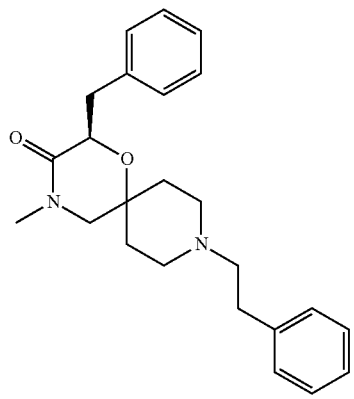 [SMILES: CN1CC2(CCN(CCc3ccccc3)CC2)O[C@H](Cc2ccccc2)C1=O]

The alternative method described for the synthesis of Example 11 was applied with some minor modifications to prepare the racemic precursor. In Step 1, cinnamoyl chloride was used as acylating agent, and in Step 2 the reaction mixture was heated to 80° C. instead of being kept at −78° C. to achieve cyclization. The title compound was obtained after chiral preparative HPLC separation. Conditions: Column: OJ; Temperature: ambient; Flow: 15 mL/min; Mobile phase: n-Heptane/(EtOH+0.33% DEA) 70/30 v/v HPLC retention time: 4.36 min; MS: 379.2 (M+H).
Table of Examples with Binding to the μ-Opioid Receptor and the $\sigma_1$-Receptor:

Biological Activity
Pharmacological Study
Human $\sigma_1$ Receptor Radioligand Assay To investigate binding properties of test compounds to human $\sigma_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human μ-Opioid Receptor Radioligand Assay To investigate binding properties of test compounds to human μ-opioid receptor, transfected CHO-K1 cell membranes and [$^3$H]-DAMGO (Perkin Elmer, ES-542-C), as the radioligand, were used. The assay was carried out with 20 μg of membrane suspension, 1 nM of [$^3$H]-DAMGO in either absence or presence of either buffer or 10 μM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the µ-opioid receptor it is a very preferred embodiment in which the compounds are selected which act as dual ligands of the $\sigma_1$ receptor and the µ-opioid receptor and especially compounds which have a binding expressed as $K_i$ which is preferably <1000 nM for both receptors, more preferably <500 nM, even more preferably <100 nM.

The following scale as been adopted for representing the binding to the $\sigma_1$ receptor and the µ-opioid receptor expressed as $K_i$:

+ Both $K_i$-µ and $K_i$-$\sigma_1$ >=500 nM
++ One $K_i$<500 nM while the other $K_i$ is >=500 nM
+++ Both $K_i$-µ and $K_i$-$\sigma_1$ <500 nM
++++ Both $K_i$-µ and $K_i$-$\sigma_1$ <100 nM All compounds prepared in the present application exhibit binding to the $\sigma_1$ receptor and the µ-opioid receptor, in particular the following binding results are shown:

| Ex | µ and $\sigma_1$ dual binding |
|---|---|
| 1 | + |
| 2 | + |
| 3 | ++ |
| 4 | ++ |
| 5 | ++ |
| 6 | ++ |
| 7 | ++++ |
| 8 | ++++ |
| 9 | + |
| 10 | + |
| 11 | +++ |
| 12 | + |
| 13 | + |
| 14 | + |
| 15 | + |
| 16 | + |
| 17 | +++ |
| 18 | ++++ |
| 19 | + |
| 20 | + |
| 21 | + |
| 22 | + |
| 23 | ++ |
| 24 | + |
| 25 | + |
| 26 | + |
| 27 | ++ |
| 28 | + |
| 29 | ++ |
| 30 | ++++ |
| 31 | +++ |
| 32 | ++++ |
| 33 | +++ |
| 34 | ++++ |
| 35 | ++++ |
| 36 | ++++ |
| 37 | +++ |
| 38 | +++ |
| 39 | ++++ |
| 40 | ++++ |
| 41 | ++++ |
| 42 | ++++ |
| 43 | +++ |
| 44 | +++ |
| 45 | ++ |
| 46 | +++ |
| 47 | +++ |
| 48 | ++ |
| 49 | ++ |
| 50 | +++ |
| 51 | +++ |
| 52 | +++ |
| 53 | +++ |
| 54 | ++ |
| 55 | +++ |
| 56 | + |
| 57 | ++ |
| 58 | ++ |
| 59 | ++ |
| 60 | ++ |
| 61 | +++ |
| 62 | ++ |
| 63 | + |
| 64 | +++ |
| 65 | ++++ |
| 66 | +++ |
| 67 | ++++ |
| 68 | +++ |
| 69 | +++ |
| 70 | ++++ |
| 71 | +++ |
| 72 | +++ |
| 73 | +++ |
| 74 | ++ |
| 75 | ++++ |
| 76 | ++++ |
| 77 | ++++ |
| 78 | +++ |
| 79 | ++++ |
| 80 | ++++ |
| 81 | ++ |
| 82 | ++++ |
| 83 | ++++ |
| 84 | ++++ |
| 85 | ++ |
| 86 | ++++ |
| 87 | ++ |
| 88 | +++ |
| 89 | ++ |
| 90 | ++++ |
| 91 | ++ |
| 92 | +++ |
| 93 | + |
| 94 | ++ |
| 95 | ++ |

The invention claimed is:

1. A compound of Formula I

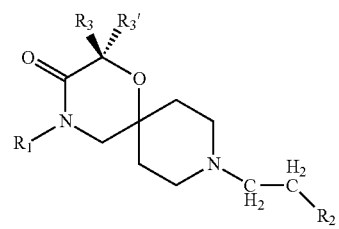

wherein $R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, wherein the cycloalkyl in $R_1$, if substituted, also in alkylcycloalkyl, is substituted with substituents selected from the group consisting of —R$_{4'''}$, halogen, —SR$_{4'''}$, —CN, haloalkyl, and —NR$_{4'''}$R$_{4'''}$,
wherein the alkyl, alkenyl and alkynyl in R$_1$, if substituted, are substituted with substituents selected from the group consisting of halogen, —CN, and haloalkyl;

R$_2$ is substituted or unsubstituted monocyclic aryl or substituted or unsubstituted monocyclic heterocyclyl,
wherein the aryl or heterocyclyl in R$_2$, if substituted, is substituted with substituents selected from the group consisting of —R$_4$, —OR$_4$, halogen, =O, —OCH$_2$CH$_2$OH, —SR$_4$, —S(O)R$_4$, —S(O)$_2$R$_4$, —CN, haloalkyl, -haloalkoxy, —NR$_4$R$_{4'''}$, —NO$_2$, —NR$_4$C(O)R$_{4'}$, —NR$_4$SO$_2$R$_{4'}$, —C(O)OR$_4$, —C(O)NR$_4$R$_{4'}$, —NR$_4$C(O)NR$_4$R$_{4''}$, —S(O)$_2$NR$_4$R$_{4'}$, and —NR$_4$S(O)$_2$NR$_4$R$_{4''}$, R$_3$ is substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{4-7}$ alkylcycloalkyl, substituted or unsubstituted C$_{4-7}$ alkylaryl, substituted or unsubstituted C$_{3-6}$ aryl, substituted or unsubstituted C$_{3-6}$ heterocyclyl or substituted or unsubstituted C$_{4-7}$ alkylheterocyclyl,
wherein the aryl, heterocyclyl or cycloalkyl in R$_3$, if substituted, also in alkylaryl, alkylcycloalkyl or alkylheterocyclyl, is substituted with substituents selected from the group consisting of —R$_4$, —OR$_4$, halogen, =O, —OCH2CH2OH, —SR$_4$, —S(O)R$_4$, —S(O)$_2$R$_4$, —CN, haloalkyl, -haloalkoxy, —NR$_4$R$_{4'''}$, —NO$_2$, —NR$_4$C(O)R$_{4'}$, —NR$_4$S(O)$_2$R$_{4'}$, —C(O)OR$_4$, —C(O)NR$_4$R$_{4'}$, —NR$_4$C(O)NR$_4$R$_{4''}$, —S(O)$_2$NR$_4$R$_{4'}$, and —NR$_4$S(O)$_2$NR$_4$R$_{4'''}$
and wherein the alkyl, alkenyl and alkynyl as defined in R$_3$, if substituted, are substituted with substituents selected from —OR$_4$, halogen, —CN, and haloalkyl, R$_{3'}$ is hydrogen, unsubstituted C$_{1-6}$ alkyl, unsubstituted C$_{2-6}$ alkenyl or unsubstituted C$_{2-6}$ alkynyl,
alternatively R$_3$ and R$_{3'}$ taken together with the connecting C-atom form an substituted or unsubstituted C$_{3-6}$ cycloalkyl,
wherein the cycloalkyl formed by R$_3$ and R$_{3'}$ taken together with the connecting C-atom, if substituted, is substituted with substituents selected from the group consisting of —R$_4$, —OR$_4$, halogen, =O, —OCH$_2$CH$_2$OH, —SR$_4$, —S(O)R$_4$, —S(O)$_2$R$_4$, —CN, haloalkyl, -haloalkoxy, —NR$_4$R$_{4'''}$, —NO$_2$, —NR$_4$C(O)R$_{4'}$, —NR$_4$S(O)$_2$R$_{4'}$, —C(O)OR$_4$, —C(O)NR$_4$R$_{4'}$, —NR$_4$C(O)NR$_4$R$_{4''}$, —S(O)$_2$NR$_4$R$_{4'}$, and —NR$_4$S(O)$_2$NR$_4$R$_{4''}$;

R$_4$, R$_{4'}$ and R$_{4''}$ are independently selected from the group consisting of hydrogen, substituted or unsubstituted C$_{1-6}$ alkyl, substituted or unsubstituted C$_{2-6}$ alkenyl or substituted or unsubstituted C$_{2-6}$ alkynyl, substituted or unsubstituted C$_{3-6}$ cycloalkyl,
wherein the cycloalkyl in R$_4$, R$_{4'}$ or R$_{4''}$, if substituted, is substituted with substituents selected from the group consisting of —R$_{4'''}$, halogen, —SR$_{4'''}$, —CN, haloalkyl, and —NR$_{4'''}$R$_{4'''}$,
wherein the alkyl, alkenyl and alkynyl in R$_4$, R$_{4'}$ or R$_{4''}$, if substituted, are substituted with substituents selected from the group consisting of halogen, —CN, and haloalkyl;

R$_{4'''}$ is hydrogen, unsubstituted C$_{1-6}$ alkyl, unsubstituted C$_{2-6}$ alkenyl, unsubstituted C$_{2-6}$ alkynyl or -Boc;

optionally as a stereoisomer, a racemate or in form of a mixture of at least two stereoisomers, in any mixing ratio, or a corresponding salt thereof, or a corresponding solvate thereof.

2. The compound according to claim 1, wherein
R$_1$ is unsubstituted C$_{1-6}$ alkyl, unsubstituted C$_{2-6}$ alkenyl, unsubstituted C$_{2-6}$ alkynyl, unsubstituted C$_{3-6}$ cycloalkyl, unsubstituted C$_{4-7}$ alkylcycloalkyl;

R$_2$ is substituted or unsubstituted monocyclic aryl or substituted or unsubstituted monocyclic heterocyclyl,
wherein the aryl or heterocyclyl, if substituted, is substituted with substituents selected from the group consisting of —R$_4$, —OR$_4$, halogen, =O, —OCH$_2$CH$_2$OH, —SR$_4$, —S(O)R$_4$, —S(O)$_2$R$_4$, —CN, haloalkyl -haloalkoxy, —NR$_4$R$_{4'''}$, —NO$_2$, —NR$_4$C(O)R$_{4'}$, —NR$_4$S(O)$_2$R$_{4'}$, —C(O)OR$_4$, —C(O)NR$_4$R$_{4'}$, —NR$_4$C(O)NR$_4$R$_{4''}$, —S(O)$_2$NR$_4$R$_{4'}$, and —NR$_4$S(O)$_2$NR$_4$R$_{4''}$;

R$_3$ is unsubstituted C$_{1-6}$ alkyl, unsubstituted C$_{2-5}$ alkenyl, unsubstituted C$_{2-6}$ alkynyl, unsubstituted C$_{3-6}$ cycloalkyl, unsubstituted C$_{4-7}$ alkylcycloalkyl, unsubstituted C$_{4-7}$ alkylaryl, unsubstituted C$_{3-6}$ aryl, unsubstituted C$_{3-6}$ heterocyclyl or unsubstituted C$_{4-7}$ alkylheterocyclyl;

R$_{3'}$ is hydrogen or unsubstituted C$_{1-6}$ alkyl, unsubstituted C$_{2-6}$ alkenyl or unsubstituted C$_{2-6}$ alkynyl,
alternatively R$_3$ and R$_{3'}$ taken together with the connecting C-atom form an unsubstituted C$_{3-6}$ cycloalkyl;

R$_4$, R$_{4'}$ and R$_{4''}$ are independently selected from the group consisting of hydrogen, unsubstituted C$_{1-6}$ alkyl, unsubstituted C$_{2-6}$ alkenyl, unsubstituted C$_{2-6}$ alkynyl, and unsubstituted C$_{3-6}$ cycloalkyl;

R$_{4'''}$ is hydrogen, unsubstituted C$_{1-6}$ alkyl, unsubstituted C$_{2-6}$ alkenyl, unsubstituted C$_{2-6}$ alkynyl or -Boc;

optionally as a stereoisomer, a racemate or in form of a mixture of at least two stereoisomers, in any mixing ratio, or a corresponding salt thereof, or a corresponding solvate thereof.

3. The compound according to claim 1, wherein the compound of formula I is a compound of formula I'

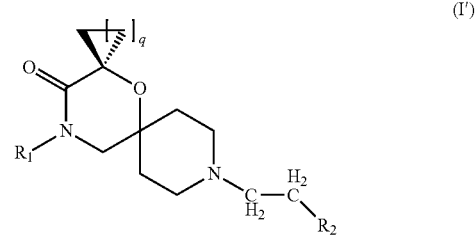

wherein q is 1, 2, 3 or 4,
optionally as a stereoisomer, a racemate or in form of a mixture of at least two stereoisomers, in any mixing ratio, or a corresponding salt thereof, or a corresponding solvate thereof.

4. The compound according to claim 3, wherein q is 1, optionally as a stereoisomer, a racemate or in form of a mixture of at least two stereoisomers, in any mixing ratio, or a corresponding salt thereof, or a corresponding solvate thereof.

5. The Compound according to claim 1, wherein the compound of formula I is a compound of formula I"

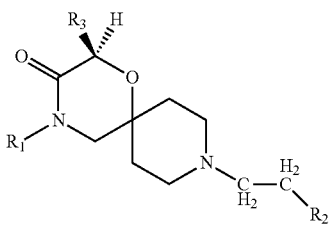

(I″)

optionally as a stereoisomer, a racemate or in form of a mixture of at least two stereoisomers, in any mixing ratio, or a corresponding salt thereof, or a corresponding solvate thereof.

6. The compound according to claim 1, wherein
$R_1$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl:
$R_2$ is substituted or unsubstituted monocyclic aryl or substituted or unsubstituted monocyclic heterocyclyl, wherein
the monocyclic aryl is substituted or unsubstituted phenyl; and
the monocyclic heterocyclyl is a heterocyclic ring system of one saturated or unsaturated ring which contains one or more heteroatoms from the group consisting of nitrogen, oxygen and/or sulfur;
$R_3$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{4-7}$ alkylcycloalkyl, substituted or unsubstituted $C_{4-7}$ alkylaryl, substituted or unsubstituted $C_{3-6}$ aryl, substituted or unsubstituted $C_{3-6}$ heterocyclyl or substituted or unsubstituted $C_{4-7}$ alkylheterocyclyl; wherein
the aryl is phenyl, and
the heterocyclyl is a heterocyclic ring system of one or more saturated or unsaturated rings of which at least one ring contains one or more heteroatoms selected from the group consisting of nitrogen, oxygen and/or sulfur;
$R_{3'}$ is hydrogen, unsubstituted $C_{1-6}$ alkyl, unsubstituted $C_{2-6}$ alkenyl or unsubstituted $C_{2-6}$ alkynyl,
or $R_3$ and $R_{3'}$ taken together with the connecting C-atom form an substituted or unsubstituted $C_{3-6}$ cycloalkyl;
$R_4$, $R_{4'}$ and $R_{4''}$ are independently selected from the group consisting of hydrogen, substituted or unsubstituted $C_{1-6}$ alkyl, substituted or unsubstituted $C_{2-6}$ alkenyl or substituted or unsubstituted $C_{2-6}$ alkynyl, and substituted or unsubstituted $C_{3-6}$ cycloalkyl;
$R_{4'''}$ is hydrogen, unsubstituted $C_{1-6}$ alkyl, unsubstituted $C_{2-6}$ alkenyl, unsubstituted $C_{2-6}$ alkynyl or -Boc;
optionally as a stereoisomer, a racemate or in form of a mixture of at least two stereoisomers, in any mixing ratio, or a corresponding salt thereof, or a corresponding solvate thereof.

7. The compound according to claim 6, wherein
$R_1$ is selected from the group consisting of substituted or unsubstituted methyl, ethyl, isopropyl; substituted or unsubstituted ethenyl, propenyl, butenyl, pentenyl, or hexenyl; substituted or unsubstituted ethyne, propyne, butyne, pentyne or hexyne; and substituted or unsubstituted cyclopropyl;

$R_2$ is selected from the group consisting of substituted or unsubstituted phenyl and substituted or unsubstituted imidazole, oxadiazole, tetrazole, pyridine, pyrimidine, piperidine, piperazine, thiazole, tetrahydropyran, morpholine, furan, triazole, isoxazole, pyrazole, thiophene, pyrrole, pyrazine, oxopyrrolidine, or pyrimidine;
$R_3$ is selected from the group consisting of substituted or unsubstituted methyl, ethyl, or isopropyl; substituted or unsubstituted ethenyl, propenyl, butenyl, pentenyl, or hexenyl; substituted or unsubstituted propyne; substituted or unsubstituted phenyl; substituted or unsubstituted imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole or quinazoline; and substituted or unsubstituted cyclopropyl, cyclobutyl, cyclopentyl or cyclohexyl;
$R_{3'}$ is selected from the group consisting of hydrogen, methyl, ethyl, ethenyl, propenyl, butenyl, pentenyl, hexenyl, ethyne, propyne, butyne, pentyne, and hexyne; or
$R_3$ and $R_{3'}$ taken together with the connecting C-atom form an substituted or unsubstituted cyclopropyl ring;
$R_4$, $R_{4'}$ and $R_{4''}$ are independently selected from the group consisting of hydrogen; substituted or unsubstituted methyl; substituted or unsubstituted ethenyl, propenyl, butenyl, pentenyl, or hexenyl; substituted or unsubstituted ethyne, propyne, butyne, pentyne or hexyne; and substituted or unsubstituted cyclopropyl, cyclobutyl, cyclopentyl or cyclohexyl;
$R_{4'''}$ is hydrogen or -Boc.

8. The compound according to claim 6, wherein
$R_1$ is unsubstituted methyl, unsubstituted ethyl, unsubstituted isopropyl or unsubstituted cyclopropyl;
$R_2$ is substituted or unsubstituted phenyl, substituted or unsubstituted pyridine, or substituted or unsubstituted thiazole;
$R_3$ is substituted or unsubstituted methyl, substituted or unsubstituted ethyl, substituted or unsubstituted isopropyl, substituted or unsubstituted propyne, substituted or unsubstituted benzyl, or —$CH_2CH_2OH$;
$R_{3'}$ is hydrogen, methyl, or ethyl;
$R_4$, $R_{4'}$ and $R_{4''}$ are independently selected from the group consisting of hydrogen and substituted or unsubstituted methyl;
$R_{4'''}$ is hydrogen or -Boc.

9. The compound according to claim 1, wherein
$R_1$ is unsubstituted $C_{1-6}$ alkyl, unsubstituted $C_{2-6}$ alkenyl, unsubstituted $C_{2-6}$ alkynyl, unsubstituted $C_{3-6}$ cycloalkyl, unsubstituted $C_{4-7}$ alkylcycloalkyl;
$R_2$ is substituted or unsubstituted monocyclic aryl or substituted or unsubstituted monocyclic heterocyclyl, wherein
the aryl is phenyl and
the heterocyclyl is a heterocyclic ring system of one saturated or unsaturated ring which contains one or more heteroatoms from the group consisting of nitrogen, oxygen and/or sulfur;
$R_3$ is unsubstituted $C_{1-6}$ alkyl, unsubstituted $C_{2-6}$ alkenyl, unsubstituted $C_{2-6}$ alkynyl, unsubstituted $C_{3-6}$ cycloalkyl, unsubstituted $C_{4-7}$ alkylcycloalkyl, unsubstituted $C_{4-7}$ alkylaryl, unsubstituted $C_{3-6}$ aryl, unsubstituted $C_{3-6}$ heterocyclyl or unsubstituted $C_{4-7}$ alkylheterocyclyl, wherein the aryl is phenyl;

the heterocyclyl is a heterocyclic ring system of one or more saturated or unsaturated rings of which at least one ring contains one or more heteroatoms from the group consisting of nitrogen, oxygen and/or sulfur;

$R_{3'}$ is hydrogen or unsubstituted $C_{1-6}$ alkyl, unsubstituted $C_{2-6}$ alkenyl or unsubstituted $C_{2-6}$ alkynyl;

or $R_3$ and $R_{3'}$ taken together with the connecting C-atom form an unsubstituted $C_{3-6}$ cycloalkyl;

$R_4$, $R_{4'}$ and $R_{4''}$ are independently selected from hydrogen, unsubstituted $C_{1-6}$ alkyl, unsubstituted $C_{2-6}$ alkenyl, unsubstituted $C_{2-6}$ alkynyl, and unsubstituted $C_{3-6}$ cycloalkyl;

$R_{4'''}$ is hydrogen, unsubstituted $C_{1-6}$ alkyl, unsubstituted $C_{2-6}$ alkenyl, unsubstituted $C_{2-6}$ alkynyl or -Boc;

optionally as a stereoisomer, a racemate or in form of a mixture of at least two stereoisomers, in any mixing ratio, or a corresponding salt thereof, or a corresponding solvate thereof.

10. The compound according to claim 9, wherein $R_1$ is methyl, ethyl, isopropyl, ethenyl, propenyl, butenyl, pentenyl, hexenyl, ethyne, propyne, butyne, pentyne, hexyne, or cyclopropyl;

$R_2$ is selected from the group consisting of substituted or unsubstituted phenyl and substituted or unsubstituted imidazole, oxadiazole, tetrazole, pyridine, pyrimidine, piperidine, piperazine, thiazole, tetrahydropyran, morpholine, furan, triazole, isoxazole, pyrazole, thiophene, pyrrole, pyrazine, oxopyrrolidine, or pyrimidine;

$R_3$ is methyl, ethyl, isopropyl, ethenyl, propenyl, butenyl, pentenyl, hexenyl, propyne, phenyl; imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole, or cyclopropyl;

$R_{3'}$ is hydrogen, methyl, ethyl, isopropyl ethenyl, propenyl, butenyl, pentenyl, hexenyl, ethyne, propyne, butyne, pentyne, or hexyne; or $R_3$ and $R_{3'}$ taken together with the connecting C-atom form a cyclopropyl or cyclopentyl ring;

$R_4$, $R_{4'}$ and $R_{4'''}$ are independently selected from the group consisting of hydrogen, methyl; ethenyl, propenyl, butenyl, pentenyl, hexenyl, ethyne, propyne, butyne, pentyne, hexyne, cyclopropyl, cyclobutyl, cyclopentyl, and cyclohexyl;

$R_{4'''}$ is hydrogen or -Boc.

11. The compound according to claim 9, wherein $R_1$ is methyl, ethyl, isopropyl, or cyclopropyl;

$R_2$ is substituted or unsubstituted phenyl, substituted or unsubstituted pyridine, or substituted or unsubstituted thiazole;

$R_3$ is methyl, ethyl, isopropyl, propyne, benzyl, or —$CH_2CH_2OH$;

$R_{3'}$ is hydrogen, methyl, or ethyl;

$R_4$, $R_{4'}$ and $R_{4'''}$ are independently selected from the group consisting of hydrogen and methyl;

$R_{4'''}$ is hydrogen or -Boc.

12. The compound according to claim 1, wherein the compound is selected from the group consisting of:

12-ethyl-8-{2-[3-(trifluoromethyl)pyridin-2-yl]ethyl}-4-oxa-8,12-diazadispiro[2.1.5.3]tridecan-13-one 12-ethyl-8-{2-[6-(trifluoromethyl)pyridin-2-yl]ethyl}-4-oxa-8,12-diazadispiro[2.1.5.3]tridecan-13-one 12-ethyl-8-[2-(3-fluoropyridin-2-yl)ethyl]-4-oxa-8,12-diazadispiro[2.1.5.3]tridecan-13-one 12-ethyl-8-{2-[4-(trifluoromethyl)pyridin-2-yl]ethyl}-4-oxa-8,12-diazadispiro[2.1.5.3]tridecan-13-one 8-[2-(3-chloropyridin-2-yl)ethyl]-12-ethyl-4-oxa-8,12-diazadispiro[2.1.5.3]tridecan-13-one 8-[2-(6-aminopyridin-2-yl)ethyl]-12-ethyl-4-oxa-8,12-diazadispiro[2.1.5.3]tridecan-13-one 12-ethyl-8-phenethyl-4-oxa-8,12-diazadispiro[2.1.5.3]tridecan-13-one 12-isopropyl-8-phenethyl-4-oxa-8,12-diazadispiro[2.1.5.3]tridecan-13-one 12-isopropyl-8-[2-(pyridin-2-yl)ethyl]-4-oxa-8,12-diazadispiro[2.1.5.3]tridecan-13-one dihydrochloride 12-ethyl-8-[2-(pyridin-2-yl)ethyl]-4-oxa-8,12-diazadispiro[2.1.5.3]tridecan-13-one (R)-2,4-dimethyl-9-phenethyl-1-oxa-4,9-diazaspiro[5.5]undecan-3-one 12-ethyl-8-{2-[6-(trifluoromethyl)pyridin-3-yl]ethyl}-4-oxa-8,12-diazadispiro[2.1.5.3]tridecan-13-one 12-ethyl-8-[2-(6-methoxypyridin-2-yl)ethyl]-4-oxa-8,12-diazadispiro[2.1.5.3]tridecan-13-one 12-ethyl-8-[2-(6-hydroxypyridin-2-yl)ethyl]-4-oxa-8,12-diazadispiro[2.1.5.3]tridecan-13-one 4-(2-{12-ethyl-13-oxo-4-oxa-8,12-diazadispiro[2.1.5.3]tridecan-8-yl}ethyl)benzene-1-sulfonamide 4-(2-{12-ethyl-13-oxo-4-oxa-8,12-diazadispiro[2.1.5.3]tridecan-8-yl}ethyl)-N-methylbenzene-1-sulfonamide 12-ethyl-8-{2-[3-(trifluoromethoxy)phenyl]ethyl}-4-oxa-8,12-diazadispiro[2.1.5.3]tridecan-13-one (R)-4-ethyl-2-methyl-9-phenethyl-1-oxa-4,9-diazaspiro[5.5]undecan-3-one 12-ethyl-8-(3-nitrophenethyl)-4-oxa-8,12-diazadispiro[2.1.5.3]tridecan-13-one 12-ethyl-8-(3-methoxyphenethyl)-4-oxa-8,12-diazadispiro[2.1.5.3]tridecan-13-one tert-butyl (4-(2-(12-ethyl-13-oxo-4-oxa-8,12-diazadispiro[2.1.5.3]tridecan-8-yl)ethyl)thiazol-2-yl)carbamate methyl 4-(2-{12-ethyl-13-oxo-4-oxa-8,12-diazadispiro[2.1.5.3]tridecan-8-yl}ethyl)benzoate 12-ethyl-8-[2-(pyridin-4-yl)ethyl]-4-oxa-8,12-diazadispiro[2.1.5.3]tridecan-13-one 12-ethyl-8-[2-(pyridin-3-yl)ethyl]-4-oxa-8,12-diazadispiro[2.1.5.3]tridecan-13-one 12-ethyl-8-(4-methoxyphenethyl)-4-oxa-8,12-diazadispiro[2.1.5.3]tridecan-13-one 12-ethyl-8-(2-methoxyphenethyl)-4-oxa-8,12-diazadispiro[2.1.5.3]tridecan-13-one 3-(2-{12-ethyl-13-oxo-4-oxa-8,12-diazadispiro[2.1.5.3]tridecan-8-yl}ethyl)benzonitrile 4-(2-{12-ethyl-13-oxo-4-oxa-8,12-diazadispiro[2.1.5.3]tridecan-8-yl}ethyl)-N,N-dimethylbenzamide 8-[2-fluorophenethyl]-12-methyl-4-oxa-8,12-diazadispiro[2.1.5.3]tridecan-13-one 8-[2-fluorophenethyl]-12-isopropyl-4-oxa-8,12-diazadispiro[2.1.5.3]tridecan-13-one (R)-2-isopropyl-4-methyl-9-phenethyl-1-oxa-4,9-diazaspiro[5.5]undecan-3-one (R)-4-ethyl-9-(2-fluorophenethyl)-2-methyl-1-oxa-4,9-diazaspiro[5.5]undecan-3-one (R)-2-ethyl-4-methyl-9-phenethyl-1-oxa-4,9-diazaspiro [5.5]undecan-3-one
(R)-9-(3-fluorophenethyl)-4-isopropyl-2-methyl-oxa-4,9-diazaspiro[5.5]undecan-3-one
(R)-4-cyclopropyl-9-(2-fluorophenethyl)-2-methyl-1-oxa-4,9-diazaspiro[5.5]undecan-3-one
(R)-4-isopropyl-2-methyl-9-phenethyl-1-oxa-4,9-diazaspiro[5.5]undecan-3-one
(R)-9-(2-fluorophenethyl)-2,4-dimethyl-1-oxa-4,9-diazaspiro[5.5]undecan-3-one
(R)-9-(3-fluorophenethyl)-2,4-dimethyl-1-oxa-4,9-diazaspiro[5.5]undecan-3-one
(R)-9-(2-fluorophenethyl)-4-isopropyl-2-methyl-1-oxa-4,9-diazaspiro[5.5]undecan-3-one
(R)-4-cyclopropyl-2-methyl-9-phenethyl-1-oxa-4,9-diazaspiro[5.5]undecan-3-one
(R)-4-cyclopropyl-9-(3-fluorophenethyl)-2-methyl-1-oxa-4,9-diazaspiro[5.5]undecan-3-one
(R)-4-ethyl-9-(3-fluorophenethyl)-2-methyl-1-oxa-4,9-diazaspiro[5.5]undecan-3-one
8-(3-fluorophenethyl)-12-isopropyl-4-oxa-8,12-diazadispiro[2.1.5.3]tridecan-13-one hydrochloride
(R)-2,4-dimethyl-9-(3-(trifluoromethyl)phenethyl)-1-oxa-4,9-diazaspiro[5.5]undecan-3-one
(R)-2,4-dimethyl-9-(2-(trifluoromethoxy)phenethyl)-1-oxa-4,9-diazaspiro[5.5]undecan-3-one
(R)-9-(2-fluorophenethyl)-2-isopropyl-4-methyl-1-oxa-4,9-diazaspiro[5.5]undecan-3-one
(R)-9-(3-fluorophenethyl)-2-isopropyl-4-methyl-1-oxa-4,9-diazaspiro[5.5]undecan-3-one
(R)-2,4-dimethyl-9-(2-(trifluoromethyl)phenethyl)-1-oxa-4,9-diazaspiro[5.5]undecan-3-one
(R)-9-(2,6-difluorophenethyl)-4-isopropyl-2-methyl-1-oxa-4,9-diazaspiro[5.5]undecan-3-one
(R)-9-(2,5-difluorophenethyl)-4-isopropyl-2-methyl-1-oxa-4,9-diazaspiro[5.5]undecan-3-one
(R)-9-(2,3-difluorophenethyl)-4-isopropyl-2-methyl-1-oxa-4,9-diazaspiro[5.5]undecan-3-one
(R)-2-ethyl-9-(2-fluorophenethyl)-4-methyl-1-oxa-4,9-diazaspiro[5.5]undecan-3-one
(R)-2-ethyl-9-(3-fluorophenethyl)-4-methyl-1-oxa-4,9-diazaspiro[5.5]undecan-3-one
2,2,4-trimethyl-9-phenethyl-1-oxa-4,9-diazaspiro[5.5]undecan-3-one
12-methyl-8-phenethyl-4-oxa-8,12-diazadispiro[2.1.5.3]tridecan-13-one
8-(3-aminophenethyl)-12-ethyl-4-oxa-8,12-diazadispiro[2.1.5.3]tridecan-13-one
N-[3-(2-{12-ethyl-13-oxo-4-oxa-8,12-diazadispiro[2.1.5.3]tridecan-8-yl}ethyl)phenyl]acetamide
[3-(2-{12-ethyl-13-oxo-4-oxa-8,12-diazadispiro[2.1.5.3]tridecan-8-yl}ethyl)phenyl]urea
4-(2-{12-ethyl-13-oxo-4-oxa-8,12-diazadispiro[2.1.5.3]tridecan-8-yl}ethyl)-N-methylbenzamide
12-ethyl-8-(2-hydroxyphenethyl)-4-oxa-8,12-diazadispiro[2.1.5.3]tridecan-13-one
12-ethyl-8-(3-hydroxyphenethyl)-4-oxa-8,12-diazadispiro[2.1.5.3]tridecan-13-one
12-ethyl-8-(4-hydroxyphenethyl)-4-oxa-8,12-diazadispiro[2.1.5.3] tridecan-13-one hydrochloride
8-[2-(2-aminothiazol-4-yl)ethyl]-12-ethyl-4-oxa-8,12-diazadispiro[2.1.5.3]tridecan-13-one
2,2-diethyl-4-methyl-9-phenethyl-1-oxa-4,9-diazaspiro[5.5]undecan-3-one
4-cyclopropyl-9-(2-fluorophenethyl)-2,2-dimethyl-1-oxa-4,9-diazaspiro[5.5]undecan-3-one
8-(2,5-difluorophenethyl)-12-isopropyl-4-oxa-8,12-diazadispiro[2.1.5.3]tridecan-13-one
8-(2,3-difluorophenethyl)-12-isopropyl-4-oxa-8,12-diazadispiro[2.1.5.3]tridecan-13-One
10-(2-fluorophenethyl)-14-methyl-6-oxa-10,14-diazadispiro[4.1.5.3]pentadecan-15-one
10-(3-fluorophenethyl)-14-methyl-6-oxa-10,14-diazadispiro[4.1.5.3]pentadecan-15-one
(R)-9-(2,5-difluorophenethyl)-4-ethyl-2-methyl-1-oxa-4,9-diazaspiro[5.5]undecan-3-one
8-(2,5-difluorophenethyl)-12-ethyl-4-oxa-8,12-diazadispiro[2.1.5.3]tridecan-13-one
12-ethyl-8-(3-fluorophenethyl)-4-oxa-8,12-diazadispiro[2.1.5.3]tridecan-13-one
12-ethyl-8-(2-fluorophenethyl)-4-oxa-8,12-diazadispiro[2.1.5.3]tridecan-13-one
(R)-9-(2,3-difluorophenethyl)-2,4-dimethyl-1-oxa-4,9-diazaspiro[5.5]undecan-3-one
(R)-2,4-diethyl-9-(2-fluorophenethyl)-1-oxa-4,9-diazaspiro[5.5]undecan-3-one
(R)-2,4-diethyl-9-(3-fluorophenethyl)-1-oxa-4,9-diazaspiro[5.5]undecan-3-one
(R)-2-ethyl-9-(3-fluorophenethyl)-4-isopropyl-1-oxa-4,9-diazaspiro[5.5]undecan-3-one
4-ethyl-9-(3-fluorophenethyl)-2,2-dimethyl-1-oxa-4,9-diazaspiro[5.5]undecan-3-one
4-ethyl-9-(2-fluorophenethyl)-2,2-dimethyl-1-oxa-4,9-diazaspiro[5.5]undecan-3-one
(R)-2-ethyl-9-(2-fluorophenethyl)-4-isopropyl-1-oxa-4,9-diazaspiro[5.5]undecan-3-one
(R)-9-(2,5-difluorophenethyl)-2,4-dimethyl-1-oxa-4,9-diazaspiro[5.5]undecan-3-one
9-(3-fluorophenethyl)-4-isopropyl-2,2-dimethyl-1-oxa-4,9-diazaspiro[5.5]undecan-3-one
9-(2-fluorophenethyl)-4-isopropyl-2,2-dimethyl-1-oxa-4,9-diazaspiro[5.5]undecan-3-one
9-(2,3-difluorophenethyl)-4-isopropyl-2,2-dimethyl-1-oxa-4,9-diazaspiro[5.5]undecan-3-one
4-cyclopropyl-9-(2,3-difluorophenethyl)-2,2-dimethyl-1-oxa-4,9-diazaspiro[5.5]undecan-3-one
4-cyclopropyl-9-(2,5-difluorophenethyl)-22-dimethyl-1-oxa-4,9-diazaspiro[5.5]undecan-3-one
(R)-9-(2,3-difluorophenethyl)-4-ethyl-2-methyl-1-oxa-4,9-diazaspiro[5.5]undecan-3-one
9-(2,5-difluorophenethyl)-4-ethyl-2,2-dimethyl-1-oxa-4,9-diazaspiro[5.5]undecan-3-one
9-(2,3-difluorophenethyl)-4-ethyl-2,2-dimethyl-1-oxa-4,9-diazaspiro[5.5]undecan-3-one
9-(2,5-difluorophenethyl)-4-isopropyl-2,2-dimethyl-1-oxa-4,9-diazaspiro[5.5]undecan-3-one
(R)-4-cyclopropyl-9-(2,3-difluorophenethyl)-2-methyl-1-oxa-4,9-diazaspiro[5.5]undecan-3-one
(R)-4-cyclopropyl-9-(2,5-difluorophenethyl)-2-methyl-1-oxa-4,9-diazaspiro[5.5]undecan-3-one
(R)-4-methyl-9-phenethyl-2-(prop-2-yn-1-yl)-1-oxa-4,9-diazaspiro[5.5]undecan-3-one
(R)-2-(2-hydroxyethyl)-4-methyl-9-phenethyl-1-oxa-4,9-diazaspiro[5.5]undecan-3-one, and
(R)-2-benzyl-4-methyl-9-phenethyl-1-oxa-4,9-diazaspiro[5.5]undecan-3-one;
optionally in form of one of the stereoisomers, a racemate or in form of a mixture of at least two of the stereoisomers, in any mixing ratio, or a corresponding salt thereof.

13. The compound according to claim 1, wherein the compound is in the form of an enantiomer or diastereomer.

14. The compound according to claim 1, wherein the compound is in the form of a mixture of at least two enantiomers and/or diastereomers.

15. The compound according to claim 12, wherein the compound is in the form of an enantiomer or diastereomer.

16. The compound according to claim 12, wherein the compound is in the form of a mixture of at least two enantiomers and/or diastereomers.

17. A pharmaceutical composition which comprises the compound according to claim 1, or a pharmaceutically acceptable salt thereof, and a pharmaceutically acceptable carrier, adjuvant or vehicle.

18. A method of treating pain in a subject in need thereof, comprising administration of an effective amount of the compound according to claim 1.

19. The method according to claim 18, wherein the pain is selected from the group consisting of medium to severe pain, visceral pain, chronic pain, cancer pain, migraine, inflammatory pain, acute pain, neuropathic pain, allodynia, and hyperalgesia.

20. A process for the preparation of a compound of formula (I) according to claim 1,

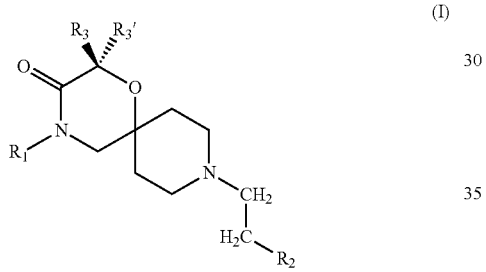
(I)

which comprises the steps of
(a) reacting a compound of formula V

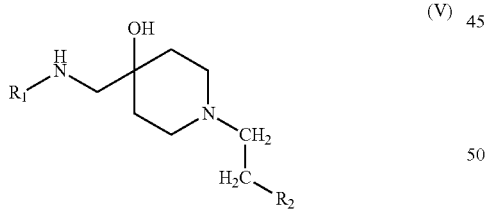
(V)

with a compound of formula VI

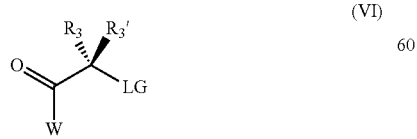
(VI)

wherein W and LG are leaving groups, to obtain a compound of formula VII

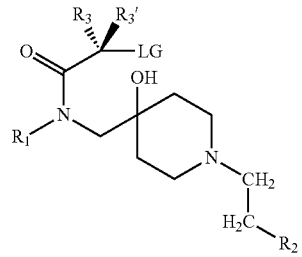
(VII)

(b) Carrying out a cyclisation of the resulting compound in a suitable solvent, in the presence of a strong base and at a temperature comprised between −78° C. and the reflux temperature.

21. A process for the preparation of a compound of general formula (I') according to claim 3:

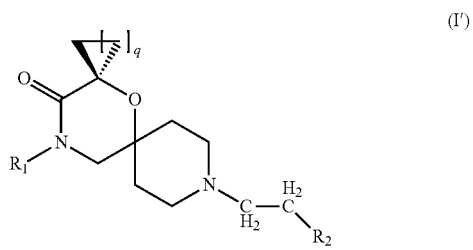
(I')

which comprises the steps of
(a) reacting a compound of formula V

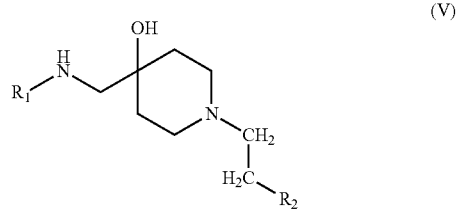
(V)

with a compound of formula XX

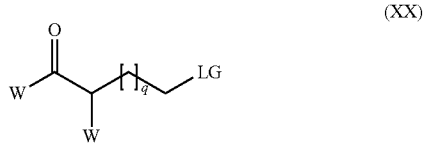
(XX)

wherein W and LG are leaving groups, q is as defined in the preceeding claims;

to obtain a compound of formula XXI

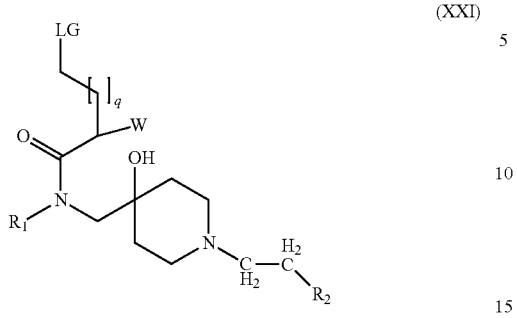

(XXI)

wherein W and LG are leaving groups,
(b) carrying out a cyclisation of the resulting compound in a suitable solvent, in the presence of a strong base and at a temperature comprised between −78° C. and the reflux temperature; leading to a compound of formula XXII,

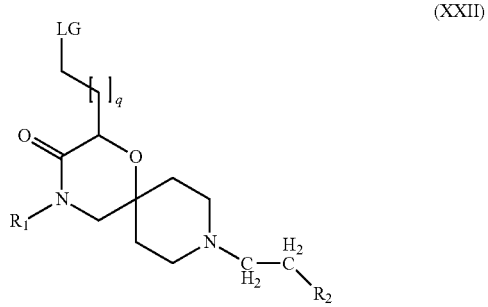

(XXII)

(c) and treating with a strong base, in an aprotic solvent, at a suitable temperature.

* * * * *

UNITED STATES PATENT AND TRADEMARK OFFICE
CERTIFICATE OF CORRECTION

PATENT NO. : 10,246,465 B2
APPLICATION NO. : 15/315486
DATED : April 2, 2019
INVENTOR(S) : Marina Virgili-Bernado et al.

It is certified that error appears in the above-identified patent and that said Letters Patent is hereby corrected as shown below:

On the Title Page

Column 2, (56), under FOREIGN PATENT DOCUMENTS: "DE 102005030061" should read -- DE 102005030051 --.

In the Claims

Column 108, Line 20: "$C_{2-5}$" should read -- $C_{2-6}$ --.

Column 111, Line 51: "$R_4'''$" should read -- $R_{4''}$ --.
Line 65: "$R_4'''$" should read -- $R_{4''}$ --.

Column 114, Line 42: "22" should read -- 2,2 --.

Signed and Sealed this
Twenty-first Day of May, 2019

Andrei Iancu
*Director of the United States Patent and Trademark Office*